United States Patent
Burkart et al.

(10) Patent No.: US 11,274,324 B2
(45) Date of Patent: Mar. 15, 2022

(54) ENGINEERING POLYKETIDE SYNTHASE IN CYANOBACTERIA

(71) Applicant: The Regents of the University of California, Oakland, CA (US)

(72) Inventors: Michael D. Burkart, San Diego, CA (US); Jeffrey Mindrebo, San Diego, CA (US); James Golden, San Diego, CA (US); Arnaud Taton, San Diego, CA (US); Julia Roulet, Rosario (AR); Hugo Gramajo, Rosario (AR); Ana Arabolaza, Rosario (AR)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/833,249

(22) Filed: Mar. 27, 2020

(65) Prior Publication Data

US 2020/0332324 A1    Oct. 22, 2020

Related U.S. Application Data

(60) Provisional application No. 62/824,534, filed on Mar. 27, 2019.

(51) Int. Cl.
| | | |
|---|---|---|
| C12P 17/16 | (2006.01) | |
| C12N 9/00 | (2006.01) | |
| C12N 9/90 | (2006.01) | |

(52) U.S. Cl.
CPC ............... *C12P 17/16* (2013.01); *C12N 9/90* (2013.01); *C12N 9/93* (2013.01); *C12Y 504/99002* (2013.01); *C12Y 604/01002* (2013.01)

(58) Field of Classification Search
None
See application file for complete search history.

(56) References Cited

U.S. PATENT DOCUMENTS

| | | | | |
|---|---|---|---|---|
| 2004/0005672 A1* | 1/2004 | Santi | ...................... | C12N 15/52 435/76 |
| 2016/0053271 A1* | 2/2016 | Gramajo | .................. | C12N 9/93 435/252.3 |

OTHER PUBLICATIONS

Yang et al., "Cyanobacterial Sfp-type phosphopantetheinyl transferases functionalize carrier proteins of diverse biosynthetic pathways", Scientific Reports, 2017, 7:11888. DOI:10.1038/s41598-017-12244-3.*

Wang et al., "A Genetic Toolbox for Modulating the Expression of Heterologous Genes in the Cyanobacterium *Synechocystis* sp. PCC 6803", ACS Synthetic Biology, 2018, vol. 7, No. 1, pp. 276-286. doi.org/10.1021/acssynbio.7b00297.*

Begemann, M.B. et al. (Oct. 1, 2013). "An organic acid based counter selection system for cyanobacteria," *PLoS One* 8(10):e76594.

Chen, Y. et al. (Dec. 2016, e-published Oct. 14, 2016). "Self-replicating shuttle vectors based on pANS, a small endogenous plasmid of the unicellular cyanobacterium *Synechococcus elongatus* PCC 7942," Microbiology 162(12):2029-2041.

Dubendorf, J.W. et al. (May 5, 1991). "Controlling basal expression in an inducible T7 expression system by blocking the target T7 promoter with lac repressor," *J Mol Biol* 219(1):45-59.

Ducat, D.C. et al. (Feb. 2011, e-published Jan. 5, 2011). "Engineering cyanobacteria to generate high-value products," *Trends Biotechnol* 29(2):95-103.

Hughes, A.J. et al. (Feb. 25, 2011). "Enzymatic extender unit generation for in vitro polyketide synthase reactions: structural and functional showcasing of Streptomyces coelicolor MatB," *Chem Biol* 18(2):165-176.

Ishikawa, F. et al. (Jan. 2012, e-published Dec. 29, 2011). "Dehydratase-specific probes for fatty acid and polyketide synthases," *J Am Chem Soc* 134(2):769-772.

Khosla, C. et al. (1999). "Tolerance and specificity of polyketide synthases," *Annu Rev Biochem* 68:219-253.

Ma, A.T. et al. (Nov. 2014, e-published Aug. 22, 2014). "Regulation of gene expression in diverse cyanobacterial species by using theophylline-responsive riboswitches," *Appl Environ Microbiol* 80(21):6704-6713.

Mathur, M. et al. (Sep. 25, 1992). "Molecular cloning and sequencing of the gene for mycocerosic acid synthase, a novel fatty acid elongating multifunctional enzyme, from *Mycobacterium tuberculosis* var. *bovis* Bacillus Calmette-Guerin," *The Journal of Biological Chemistry* 267(27):19388-19395.

Menendez-Bravo, S. et al. (Jul. 2014, e-published May 14, 2014). "Expanding the chemical diversity of natural esters by engineering a polyketide-derived pathway into *Escherichia coli,*" *Metab Eng* 24: 97-106.

Murli, S. et al. (Aug. 2003, e-published Jul. 26, 2003). "Metabolic engineering of *Escherichia coli* for improved 6-deoxyerythronolide B production," *J Ind Microbiol Biotechnol* 30(8):500-509.

Oliver, J.W.K. et al. (Jan. 22, 2013, e-published Jan. 7, 2013). "Cyanobacterial conversion of carbon dioxide to 2,3-butanediol," *PNAS USA* 110(4):1249-1254.

Onwueme, K.C. et al. (Mar. 30, 2004, e-published Mar. 18, 2004). "Mycobacterial polyketide-associated proteins are acyltransferases: proof of principle with *Mycobacterium tuberculosis* PapA5," *PNAS USA* 101 (13):4608-4613.

Pfeifer, B.A. et al. (Mar. 2001). "Biosynthesis of polyketides in heterologous hosts," *Microbiol Mol Biol Rev* 65(1):106-118.

Quadri, L.E. et al. (Feb. 10, 1998). "Characterization of Sfp, a Bacillus subtilis phosphopantetheinyl transferase for peptidyl carrier protein domains in peptide synthetases," *Biochemistry* 37(6):1585-1595.

Taton A. et al. (2014, e-published Jul. 29, 2014). "Broad-host-range vector system for synthetic biology and biotechnology in cyanobacteria," *Nucleic Acids Res* 42(17):e136.

* cited by examiner

*Primary Examiner* — Suzanne M Noakes
(74) *Attorney, Agent, or Firm* — Mintz, Levin, Cohn, Ferris, Glovsky and Popeo, P.C.

(57) ABSTRACT

Provided herein, inter alia, is a modular-functional technology for the expression of a functional heterologous polyketide synthases (PKS) system in a photosynthetic cyanobacteria.

19 Claims, 16 Drawing Sheets

Specification includes a Sequence Listing.

ENGINEERING POLYKETIDE SYNTHASE IN CYANOBACTERIA

CROSS-REFERENCE TO RELATED APPLICATIONS

This application claims priority to U.S. Application No. 62/824,534 filed Mar. 27, 2019, the disclosure of which is incorporated by reference herein in its entirety.

REFERENCE TO A "SEQUENCE LISTING," A TABLE, OR A COMPUTER PROGRAM LISTING APPENDIX SUBMITTED AS AN ASCII FILE

The Sequence Listing written in file 048537-604001US_SEQUENCELISTING.TXT, created on Jul. 6, 2020, 20,480 bytes, machine format IBM-PC, MS-Windows operating system, is hereby incorporated by reference.

BACKGROUND

Human society has always depended on biomass-derived carbon and energy for nutrition and survival. In recent history, we have also become dependent on petroleum derived carbon and energy for commodity chemicals and fuels. However, the nonrenewable nature of petroleum stands in stark contrast to the renewable carbon and energy present in biomass, where biomass is essentially a temporary storage unit for atmospheric carbon and sunlight-derived energy (Ingram et al. 2010). At present, many bioindustrial processes rely on the fermentation of heterotrophic bacteria to produce various fine chemicals such as vitamins, enzymes, and amino acids. Nevertheless, the economic viability of these production schemes is limited by the cost of carbon substrates used in the fermentation processes.

Polyketide synthases (PKSs) are large multienzyme systems that are responsible for the stepwise biosynthesis of extraordinarily complex natural products from simple 2-, 3-, and 4-carbon building blocks such as acetyl-CoA, propionyl-CoA, butyryl-CoA, and their activated derivatives, malonyl-, methylmalonyl-, and ethylmalonyl-CoA. These polyketide natural products are known to possess a wealth of pharmacologically important activities, comprising antimicrobial, antifungal, antiparasitic, antitumor, and immunosuppressive properties (Khosla et al. 1999). Moreover, reduced polyketides are also a good source of hydrocarbons that can be used as biofuels or biolubricant-like molecules, as was recently shown in our laboratory (Menendez-Bravo et al. 2014). A potential barrier for the production of many important polyketides in large-scale manufacturing is the lack of tractable fermentation hosts. Native polyketide producers can have characteristics that limit their utility for large-scale polyketide production: they sometimes grow slowly and are often difficult to manipulate genetically (Murli et al. 2003).

Provided herein, inter alia, are solutions to these and other problems in the art.

BRIEF SUMMARY

Provided herein are recombinant cyanobacterium comprising an exogenous gene capable of expressing a polyketide synthase. In aspects, the cyanobacterium is of the genus *Synechococcus*, such as *Synechococcus elongatus*.

Provided herein are recombinant cyanobacterium comprising an exogenous gene capable of expressing an exogenous Sfp-type phosphopantetheinyl transferase (PPTase).

Provided herein are processes for producing polyketides by adding polyketide precursors to recombinant cyanobacterium that comprise an exogenous gene capable of expressing a polyketide synthase.

These and other embodiments and aspects of the disclosure are provided in detail herein.

BRIEF DESCRIPTION OF THE DRAWINGS

FIG. 4A shows radio-TLC analysis of total lipid fraction from *S. elongatus* recombinant strains MatB F pfm: lanes 1-6; MatB F (without module III): lane 7; and from *E. coli* RQ1 MBE producer strain (Menendez-Bravo et al. 2014): lane 8. The lipid fractions on lanes 1, 2, and 3, were extracted from 3 cultures grown from 3 independent clones as biological replicates. The cultures used for lanes 4, 5 and 6 were grown from the same clone as for lane 1 but with different supply of n-octanol and methylmalonate as indicated below each lane. FIG. 4B shows radio-TLC analysis of total lipid fraction from *S. elongatus* recombinant strain MatB B6 pfm: lanes 1-6; MatB B6 (without module III): line 7; AMC2302 WT: lane 8 and from *E. coli* RQ1MBE producer strain (Menendez-Bravo et al. 2014): lane 9. The lipid fractions on lanes: 1, 2, and 3, were extracted from 3 cultures grown from 3 independent clones as biological replicates. The cultures used for lanes 4, 5 and 6 were grown from the same clone as for lane 1 but with differing addition of n-octanol and methylmalonate, as indicated below each lane. Modules used in each strain (see FIG. 1) are indicated to the left of each gel.

FIG. 6A shows radio-TLC analysis of total lipid fraction from *S. elongatus* recombinant strain MatB F pfm plus methylmalonate 10 mM, n-octanol 0.25 mM and theophylline 0, 0.5, 1, 2, 4, 8 mM respectively; last lane: MBE standard, obtained from the *E. coli* MBE producer strain. FIG. 6B shows radio-TLC analysis of total lipid fraction from *S. elongatus* recombinant strain MatB B6 pfm plus methylmalonate 10 mM, n-octanol 0.25 mM and theophylline 0, 0.5, 1, 2, 4, 8 mM respectively; wt: wild type *S. elongatus* strain cultivated after theophylline induction, with n-octanol and methylmalonate; *E. coli*: total lipid extract, as MBE standard, obtained from the *E. coli* MBE producer strain.

FIG. 7A shows design and schematic of the extender unit production module and the polyketide production module. FIG. 7B shows design and schematic of the regulation and post-translation modification module.

FIG. 8A is an image of an immunoblot of soluble protein extracts from three independent clones of the *S. elongatus* AMC2302 recombinant strains: JR101 (lanes 1, 2, 3) and JR105 (lanes 4, 5, 6), and the wild-type strain (lane 7). FIG. 8B is an image of an immunoblot of soluble protein extracts from three independent clones of *S. elongatus* AMC2302 recombinant strains: JR102 (lanes 1, 2, 3), JR106 (lanes 4, 5, 6) and JR104 (lane 7), and the wild-type strain (lane 8). The MatB, epimerase, and MutA proteins were tagged with FLAG-tag and detected with anti-FLAG antibodies.

FIG. 10A is an image of an immunoblot of soluble protein extracts from three independent clones of the *S. elongatus* AMC2302 recombinant strains: JR101 (lanes 1, 2, 3), JR105 (lanes 4, 5, 6), JR107 (lanes 7, 8, 9), and JR103 (without module III) (lane 10), and the wild-type strain (lane 11). FIG. 10B is an image of an immunoblot of soluble protein extracts from three independent clones of the *S. elongatus* AMC2302 recombinant strains: JR102 (lanes 1, 2, 3), JR106 (lanes 4, 5, 6), JR108 (lanes 7, 8, 9), and JR104 (without module III) (lane 10), and the wild-type strain (lane 11). Mas, FadD28, and PapA5 proteins were His-tagged and detected with 943 anti-His antibodies.

FIG. 12A is an image showing cell growth after addition of substrate. Methylmalonate (me-malonate) and propionate were added to *S. elongatus* AMC2302 wild type at different concentrations: 0, 1, 5, 10, 15, and 20 mM. Each column is a duplicate of the experiment. FIG. 12B is an image showing cell growth after addition of substrate. n-octanol was added to *S. elongatus* AMC2302 wild type at different concentrations: 0.125, 0.25, 0.5, 1, 2, and 0 mM. Each column is a duplicate (FIG. 12A), or triplicate of the experiment (FIG. 12B).

DETAILED DESCRIPTION

Definitions

Figure 1:
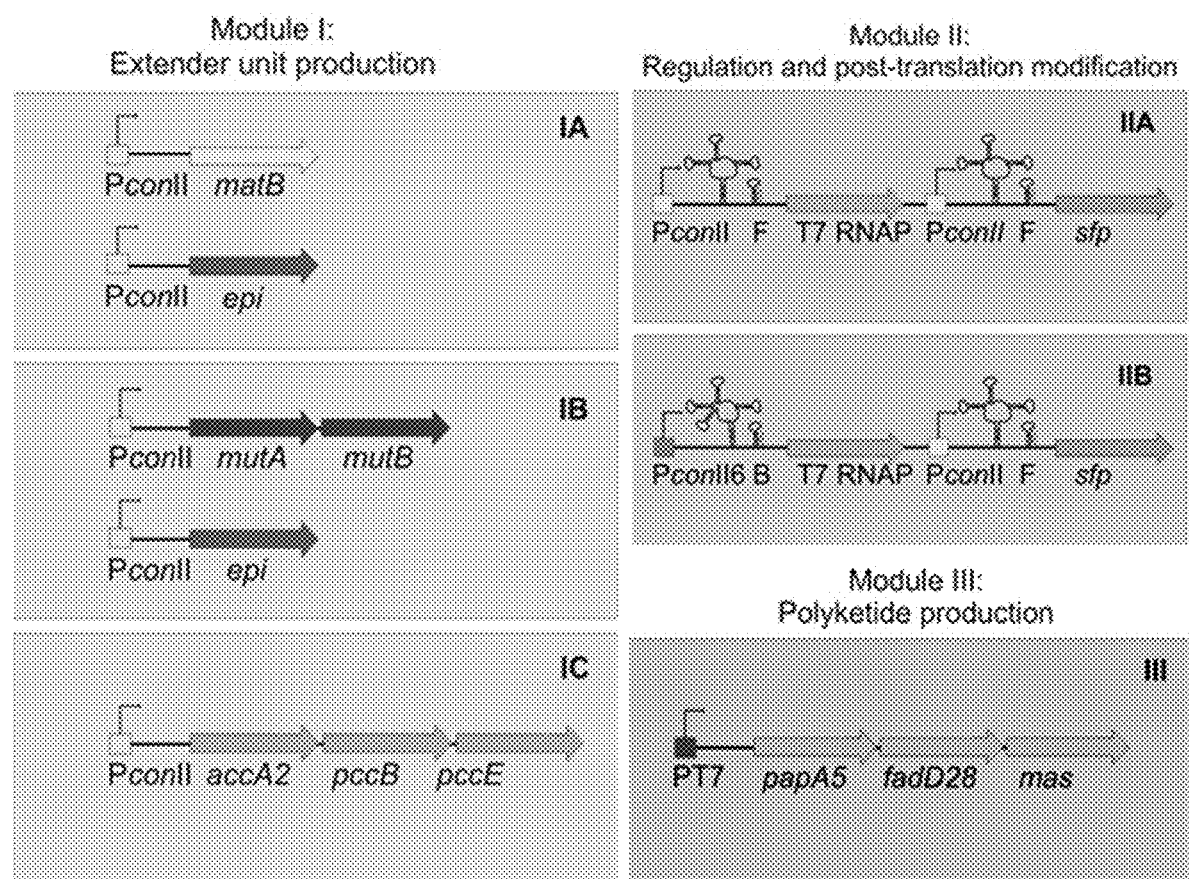
FIG. 1 shows modular-design of essential components for the production of PKS-derived compounds in *S. elongatus*. Module I: for biosynthesis of the carboxyacyl-CoA precursors using three different routes: module IA contains matB and epimerase genes; module IB contains mutA, mutB and epimerase genes; module IC contains accA2, pccB and pccE genes. Module II: designed for the post-translational modification of the PKS and the controlled orthogonal expression of it using two variants of the T7 RNA polymerase expression devices. In module IIA, the T7RNApol is expressed from the PconII with riboswitch F; in module IIB the T7 RNA polymerase is expressed from a mutated PconII with riboswitch B. In both modules the sfp is expressed from the PconII with riboswitch F. Module III: harbors the genes for the biosynthesis of the PKS derived products, in this case the mycobacterial PKS Mas pathway that comprises papA5, fadD28 and mas genes. These genes were engineered in a single operon expressed from PT7.

The abbreviations used herein have their conventional meaning within the chemical and biological arts. The chemical structures and formulae set forth herein are constructed according to the standard rules of chemical valency known in the chemical arts.

The term "polyketide synthase" or "PKS" as used herein refers to the family of multi-modular enzymes, multi-domain enzymes, or enzyme complexes that produce polyketide intermediate products or polyketides. Substrates of polyketide synthases may comprise acetyl-CoA or analogs or derivatives thereof. In embodiments, the acetyl-CoA derivative is propionyl-CoA, malonyl Co-A or methylmalonyl-CoA. PKSs may rely on protein-protein interactions within and/or between modules to function. PKS may produce one or more intermediate products between successive modules. In embodiments, the PKS is Mycocerosic acid synthase (MAS).

A "malonyl-CoA synthetase", "malonyl-CoA synthetase protein" or "MatB protein" as referred to herein, also known as acyl-CoA synthetase, comprises any of the recombinant or naturally-occurring forms of the malonyl-CoA synthetase enzyme or variants or homologs thereof that maintain malonyl-CoA synthetase enzyme activity (e.g. within at least 50%, 80%, 90%, 95%, 96%, 97%, 98%, 99% or 100% activity compared to malonyl-CoA synthetase). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring malonyl-CoA synthetase protein. In embodiments, the malonyl-CoA synthetase protein is substantially identical to the protein identified by the Accession number CAB86109 or a variant or homolog having substantial identity thereto.

An "acyl-CoA carboxylase complex A", "acyl-CoA carboxylase complex A protein" as referred to herein comprises any of the recombinant or naturally-occurring forms of the acyl-CoA carboxylase complex A protein, also known as acyl-CoA carboxylase complex A subunit, acyl-coenzyme A carboxylase (ACCase) complex accA2, ACCase complex accA2, acyl-CoA carboxylase subunit accA2, acyl-CoA carboxylase a subunit or variants or homologs thereof that maintain acyl-CoA carboxylase complex A activity (e.g. within at least 50%, 80%, 90%, 95%, 96%, 97%, 98%, 99% or 100% activity compared to acyl-CoA carboxylase complex A). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring acyl-CoA carboxylase complex A protein. In embodiments, the acyl-CoA carboxylase complex A protein is substantially identical to the protein identified by the Accession number Q9EWV4 or a variant or homolog having substantial identity thereto.

An "acyl-CoA carboxylase complex pccE", "acyl-CoA carboxylase complex pccE protein" or "acyl-CoA carboxylase pccE" as referred to herein comprises any of the recombinant or naturally-occurring forms of the acyl-CoA carboxylase complex pccE, also known as acyl-CoA carboxylase complex pccE subunit, acyl-coenzyme A carboxylase (ACCase) complex pccE, ACCase complex pccE, acyl-CoA carboxylase pccE subunit or variants or homologs thereof that maintain acyl-CoA carboxylase complex pccE activity (e.g. within at least 50%, 80%, 90%, 95%, 96%, 97%, 98%, 99% or 100% activity compared to acyl-CoA carboxylase complex pccE). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring acyl-CoA carboxylase complex pccE protein. In embodiments, the acyl-CoA carboxylase complex pccE protein is substantially identical to the protein identified by the Accession number Q9EWV8 or a variant or homolog having substantial identity thereto.

An "acyl-CoA carboxylase complex pccB", "acyl-CoA carboxylase complex pccB protein" or "acyl-CoA carboxylase pccB" as referred to herein comprises any of the recombinant or naturally-occurring forms of the acyl-CoA carboxylase complex pccB, also known as acyl-CoA carboxylase complex subunit pccB, acyl-coenzyme A carboxylase (ACCase) complex pccB, ACCase complex pccB, acyl-CoA carboxylase pccB subunit or variants or homologs thereof that maintain acyl-CoA carboxylase complex activity (e.g. within at least 50%, 80%, 90%, 95%, 96%, 97%, 98%, 99% or 100% activity compared to acyl-CoA carboxylase complex pccB). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring acyl-CoA carboxylase complex pccB protein. In embodiments, the acyl-CoA carboxylase complex pccB protein is substantially identical to the protein identified by the Accession number Q9X4K7 or a variant or homolog having substantial identity thereto.

A "polyketide synthase associated protein PapA5", "polyketide synthase associated protein PapA5 protein" or "PapA5" as referred to herein comprises any of the recombinant or naturally-occurring forms of the polyketide synthase associated protein PapA5 protein or variants or homologs thereof that maintain polyketide synthase associated protein PapA5 activity (e.g. within at least 50%, 80%, 90%, 95%, 96%, 97%, 98%, 99% or 100% activity compared to polyketide synthase associated protein PapA5). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring polyketide synthase associated protein PapA5 protein. In embodiments, the polyketide synthase associated protein PapA5 protein is substantially identical to the protein identified by the Accession number I6YAN2 or a variant or homolog having substantial identity thereto.

A "long-chain-fatty-acid AMP ligase FadD28", "long-chain-fatty-acid AMP ligase FadD28 protein" or "FadD28" as referred to herein, also known as FAAL or Acyl-AMP synthetase, comprises any of the recombinant or naturally-occurring forms of the FadD28 protein or variants or homologs thereof that maintain FadD28 activity (e.g. within at least 50%, 80%, 90%, 95%, 96%, 97%, 98%, 99% or 100% activity compared to FadD28). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring FadD28 protein. In embodiments, the FadD28 is substantially identical to the protein identified by the Accession number I6XFQ7 or a variant or homolog having substantial identity thereto.

A "mycocerosic acid synthase" "mycocerosic acid synthase protein" or "Mas" as referred to herein comprises any of the recombinant or naturally-occurring forms of the mycocerosic acid synthase protein or variants or homologs thereof that maintain mycocerosic acid synthase activity (e.g. within at least 50%, 80%, 90%, 95%, 96%, 97%, 98%, 99% or 100% activity compared to mycocerosic acid synthase). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring mycocerosic acid synthase protein. In embodiments, the mycocerosic acid synthase is substantially identical to the protein identified by the Accession number I6Y231 or a variant or homolog having substantial identity thereto.

An "acetyl-coenzyme A synthetase" or "acetyl-coenzyme A synthetase protein" or "AcsA" as referred to herein comprises any of the recombinant or naturally-occurring forms of the acetyl-coenzyme A synthetase protein or variants or homologs thereof that maintain acetyl-coenzyme A synthetase activity (e.g. within at least 50%, 80%, 90%, 95%, 96%, 97%, 98%, 99% or 100% activity compared to acetyl-coenzyme A synthetase). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring acetyl-coenzyme A synthetase. In embodiments, the acetyl-coenzyme A synthetase is substantially identical to the protein identified by the Accession number Q31NI7 or a variant or homolog having substantial identity thereto.

A "T7 RNA polymerase" "T7 RNA polymerase protein" or "T7RNAP" as referred to herein comprises any of the recombinant or naturally-occurring forms of the T7 RNA polymerase protein or variants or homologs thereof that maintain T7 RNA polymerase activity (e.g. within at least 50%, 80%, 90%, 95%, 96%, 97%, 98%, 99% or 100% activity compared to T7 RNA polymerase). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring T7 RNA polymerase protein. In embodiments, the T7 RNA polymerase is substantially identical to the protein identified by the Accession number C1KTT1 or a variant or homolog having substantial identity thereto.

A "4'-phosphopantetheinyl transferase Sfp", "4'-phosphopantetheinyl transferase Sfp protein" or "Sfp" as referred to herein, also known as Surfactin synthase-activating enzyme, Sfp-type phosphopantetheinyl transferase (PPTase) or PPTase, comprises any of the recombinant or naturally-occurring forms of the Sfp protein or variants or homologs thereof that maintain Sfp activity (e.g. within at least 50%, 80%, 90%, 95%, 96%, 97%, 98%, 99% or 100% activity compared to Sfp). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Sfp protein. In embodiments, the Sfp is substantially identical to the protein identified by the Accession number P39135 or a variant or homolog having substantial identity thereto.

The terms "epimerase gene", "epimerase", or the like, as used herein refer to the any of the recombinant or naturally-occurring forms of the epimerase gene or variants or homologs thereof that code for a epimerase polypeptide capable of maintaining the activity of the epimerase polypeptide (e.g., within at least 50%, 80%, 90%, 95%, 96%, 97%, 98%, 99% or 100% activity compared to epimerase polypeptide). In some aspects, the variants or homologs have at least 90%, 95%, 96%, 97%, 98%, 99% or 100% nucleic acid sequence identity across the whole sequence or a portion of the sequence (e.g., a 50, 100, 150 or 200 continuous nucleic acid portion) compared to a naturally occurring epimerase gene. In embodiments, the epimerase gene is substantially identical to the nucleic acid sequence corresponding to the nucleic acid sequence identified by Accession No. AY046899 or a variant or homolog having substantial identity thereto.

The terms "Mas gene", "Mas", or the like, as used herein refer to the any of the recombinant or naturally-occurring forms of the mycocerosic acid synthase gene or variants or homologs thereof that code for a mycocerosic acid synthase polypeptide capable of maintaining the activity of the mycocerosic acid synthase polypeptide (e.g., within at least 50%, 80%, 90%, 95%, 96%, 97%, 98%, 99% or 100% activity compared to mycocerosic acid synthase polypeptide). In some aspects, the variants or homologs have at least 90%, 95%, 96%, 97%, 98%, 99% or 100% nucleic acid sequence identity across the whole sequence or a portion of the sequence (e.g., a 50, 100, 150 or 200 continuous nucleic acid portion) compared to a naturally occurring mycocerosic acid synthase gene. In embodiments, the mycocerosic acid synthase gene is substantially identical to the nucleic acid sequence corresponding to position 3,276,380 to 3,282,715 of the nucleic acid sequence identified by Accession No. NC_000962.3 or a variant or homolog having substantial identity thereto.

The terms "FadD28 gene", "FadD28", or the like, as used herein refer to the any of the recombinant or naturally-occurring forms of the long-chain-fatty-acid AMP ligase FadD28 gene or variants or homologs thereof that code for a long-chain-fatty-acid AMP ligase FadD28 polypeptide capable of maintaining the activity of the long-chain-fatty-acid AMP ligase FadD28 polypeptide (e.g., within at least 50%, 80%, 90%, 95%, 96%, 97%, 98%, 99% or 100% activity compared to long-chain-fatty-acid AMP ligase FadD28 polypeptide). In some aspects, the variants or homologs have at least 90%, 95%, 96%, 97%, 98%, 99% or 100% nucleic acid sequence identity across the whole sequence or a portion of the sequence (e.g., a 50, 100, 150 or 200 continuous nucleic acid portion) compared to a naturally occurring long-chain-fatty-acid AMP ligase FadD28 synthase gene. In embodiments, the long-chain-fatty-acid AMP ligase FadD28 gene is substantially identical to the nucleic acid sequence corresponding to position 3,283,335 to 3,285,077 of the nucleic acid sequence identified by Accession No. NC_000962.3 or a variant or homolog having substantial identity thereto.

The terms "PapA5 gene", "PapA5", or the like, as used herein refer to the any of the recombinant or naturally-occurring forms of the polyketide synthase associated protein PapA5 gene or variants or homologs thereof that code for a polyketide synthase associated protein PapA5 polypeptide capable of maintaining the activity of the polyketide synthase associated protein PapA5 polypeptide (e.g., within at least 50%, 80%, 90%, 95%, 96%, 97%, 98%, 99% or 100% activity compared to polyketide synthase associated protein PapA5 polypeptide). In some aspects, the variants or homologs have at least 90%, 95%, 96%, 97%, 98%, 99% or 100% nucleic acid sequence identity across the whole sequence or a portion of the sequence (e.g., a 50, 100, 150 or 200 continuous nucleic acid portion) compared to a naturally occurring polyketide synthase associated protein PapA5 gene. In embodiments, the polyketide synthase associated protein PapA5 gene is substantially identical to the nucleic acid sequence corresponding to position 3,274,949 to 3,276,217 of the nucleic acid sequence identified by Accession No. NC_000962.3 or a variant or homolog having substantial identity thereto.

The terms "mutA gene", "mutA", "MutAB gene", "MutAB" or the like, as used herein refer to the any of the recombinant or naturally-occurring forms of the methylmalonyl-CoA mutase gene or variants or homologs thereof that code for a methylmalonyl-CoA mutase polypeptide capable of maintaining the activity of the methylmalonyl-CoA mutase polypeptide (e.g., within at least 50%, 80%, 90%, 95%, 96%, 97%, 98%, 99% or 100% activity compared to methylmalonyl-CoA mutase polypeptide). In some aspects, the variants or homologs have at least 90%, 95%, 96%, 97%, 98%, 99% or 100% nucleic acid sequence identity across the whole sequence or a portion of the sequence (e.g., a 50, 100, 150 or 200 continuous nucleic acid portion) compared to a naturally occurring methylmalonyl-CoA mutase gene. In embodiments, the methylmalonyl-CoA mutase gene is substantially identical to the nucleic acid sequence corresponding to the nucleic acid sequence identified by Accession No. X14965 or a variant or homolog having substantial identity thereto.

The terms "mutB gene", "mutB", "MutAB gene", "MutAB" or the like, as used herein refer to the any of the recombinant or naturally-occurring forms of the methylmalonyl-CoA mutase gene or variants or homologs thereof that code for a methylmalonyl-CoA mutase polypeptide capable of maintaining the activity of the methylmalonyl-CoA mutase polypeptide (e.g., within at least 50%, 80%, 90%, 95%, 96%, 97%, 98%, 99% or 100% activity compared to methylmalonyl-CoA mutase polypeptide). In some aspects, the variants or homologs have at least 90%, 95%, 96%, 97%, 98%, 99% or 100% nucleic acid sequence identity across the whole sequence or a portion of the sequence (e.g., a 50, 100, 150 or 200 continuous nucleic acid portion) compared to a naturally occurring methylmalonyl-CoA mutase gene. In embodiments, the methylmalonyl-CoA mutase gene is substantially identical to the nucleic acid sequence corresponding to the nucleic acid sequence identified by Accession No. X14965 or a variant or homolog having substantial identity thereto.

The terms "4'-phosphopantetheinyl transferase Sfp gene", "sfp gene", "sfp", or the like, as used herein refer to the any of the recombinant or naturally-occurring forms of the 4'-phosphopantetheinyl transferase Sfp gene or variants or homologs thereof that code for a 4'-phosphopantetheinyl transferase Sfp polypeptide capable of maintaining the activity of the 4'-phosphopantetheinyl transferase Sfp polypeptide (e.g., within at least 50%, 80%, 90%, 95%, 96%, 97%, 98%, 99% or 100% activity compared to 4'-phosphopantetheinyl transferase Sfp polypeptide). In some aspects, the variants or homologs have at least 90%, 95%, 96%, 97%, 98%, 99% or 100% nucleic acid sequence identity across the whole sequence or a portion of the sequence (e.g., a 50, 100, 150 or 200 continuous nucleic acid portion) compared to a naturally occurring 4'-phosphopantetheinyl transferase Sfp gene. In embodiments, the epimerase gene is substantially identical to the nucleic acid sequence corresponding to the nucleic acid sequence identified by Accession No. BG10176 or a variant or homolog having substantial identity thereto.

The terms "MatB gene", "MatB", or the like, as used herein refer to the any of the recombinant or naturally-occurring forms of the malonyl-CoA synthetase (MatB) gene or variants or homologs thereof that code for a malonyl-CoA synthetase polypeptide capable of maintaining the activity of the malonyl-CoA synthetase polypeptide (e.g., within at least 50%, 80%, 90%, 95%, 96%, 97%, 98%, 99% or 100% activity compared to malonyl-CoA synthetase polypeptide). In some aspects, the variants or homologs have at least 90%, 95%, 96%, 97%, 98%, 99% or 100% nucleic acid sequence identity across the whole sequence or a portion of the sequence (e.g., a 50, 100, 150 or 200 continuous nucleic acid portion) compared to a naturally occurring malonyl-CoA synthetase gene. In embodiments, the malonyl-CoA synthetase gene is substantially identical to the nucleic acid sequence corresponding to position 2,622,576 to 2,624,033 of the nucleic acid sequence identified by Accession No. NC_003888.3 or a variant or homolog having substantial identity thereto.

The terms "accA2 gene", "AccA2", or the like, as used herein refer to the any of the recombinant or naturally-occurring forms of the acyl-CoA carboxylase complex A subunit gene or variants or homologs thereof that code for an acyl-CoA carboxylase complex A subunit polypeptide capable of maintaining the activity of the acyl-CoA carboxylase complex A subunit polypeptide (e.g., within at least 50%, 80%, 90%, 95%, 96%, 97%, 98%, 99% or 100% activity compared to acyl-CoA carboxylase complex A subunit polypeptide). In some aspects, the variants or homologs have at least 90%, 95%, 96%, 97%, 98%, 99% or 100% nucleic acid sequence identity across the whole sequence or a portion of the sequence (e.g., a 50, 100, 150 or 200 continuous nucleic acid portion) compared to a naturally occurring acyl-CoA carboxylase complex A subunit gene. In embodiments, the acyl-CoA carboxylase complex A subunit gene is substantially identical to the nucleic acid sequence corresponding to position 6,897,089 to 6,898,861 of the nucleic acid sequence identified by Accession No. NC_003888.3 or a variant or homolog having substantial identity thereto.

The terms "pccB gene", "pccB", or the like, as used herein refer to the any of the recombinant or naturally-occurring forms of the acyl-CoA carboxylase pccB subunit gene or variants or homologs thereof that code for an acyl-CoA carboxylase pccB subunit polypeptide capable of maintaining the activity of the acyl-CoA carboxylase pccB subunit polypeptide (e.g., within at least 50%, 80%, 90%, 95%, 96%, 97%, 98%, 99% or 100% activity compared to acyl-CoA carboxylase pccB subunit polypeptide). In some aspects, the variants or homologs have at least 90%, 95%, 96%, 97%, 98%, 99% or 100% nucleic acid sequence identity across the whole sequence or a portion of the sequence (e.g., a 50, 100, 150 or 200 continuous nucleic acid portion) compared to a naturally occurring acyl-CoA carboxylase pccB subunit gene. In embodiments, the acyl-CoA carboxylase pccB subunit gene is substantially identical to the nucleic acid sequence corresponding to position 5359018 to 5360610 of the nucleic acid sequence identified by Accession No. NC_003888.3 or a variant or homolog having substantial identity thereto.

The terms "pccE gene", "pccE", or the like, as used herein refer to the any of the recombinant or naturally-occurring forms of the acyl-CoA carboxylase pccE subunit gene or variants or homologs thereof that code for an acyl-CoA carboxylase pccE subunit polypeptide capable of maintaining the activity of the acyl-CoA carboxylase pccE subunit polypeptide (e.g., within at least 50%, 80%, 90%, 95%, 96%, 97%, 98%, 99% or 100% activity compared to acyl-CoA carboxylase complex pccE polypeptide). In some aspects, the variants or homologs have at least 90%, 95%, 96%, 97%, 98%, 99% or 100% nucleic acid sequence identity across the whole sequence or a portion of the sequence (e.g., a 50, 100, 150 or 200 continuous nucleic acid portion) compared to a naturally occurring acyl-CoA carboxylase pccE subunit gene. In embodiments, the acyl-CoA carboxylase pccE subunit gene is substantially identical to the nucleic acid sequence corresponding to position 5358799 to 5359008 of the nucleic acid sequence identified by Accession No. NC_003888.3 or a variant or homolog having substantial identity thereto.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to comprise, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides comprise a gene, a gene fragment, an exon, an intron, intergenic DNA (comprising, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally comprise one or more non-standard nucleotide(s), nucleotide analog(s) and/or modified nucleotides.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another: (1) Alanine (A), Glycine (G); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); (6) Phenylalanine (F), Tyrosine (Y), Tryptophan (W); (7) Serine (S), Threonine (T); and (8) Cysteine (C), Methionine (M) (see, e.g., Creighton, Proteins (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., at least 60% identity or at least 65%, 70%, 75%, 80%, 85%, 90%, 91%, 92%, 93%, 94%, 95%, 96%, 97%, 98%, 99% identity over a specified region when compared and aligned for maximum correspondence over a comparison window or designated region) as measured using a BLAST or BLAST 2.0 sequence comparison algorithms with default parameters or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also comprises sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

The term "amino acid side chain" refers to the functional substituent contained on amino acids. For example, an amino acid side chain may be the side chain of a naturally occurring amino acid. Naturally occurring amino acids are those encoded by the genetic code (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine), as well as those amino acids that are later modified, e.g., hydroxyproline, γ-carboxyglutamate, and O-phosphoserine. In embodiments, the amino acid side chain may be a non-natural amino acid side chain. In embodiments, the amino acid side chain is H,

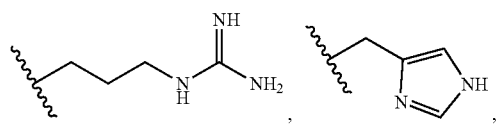

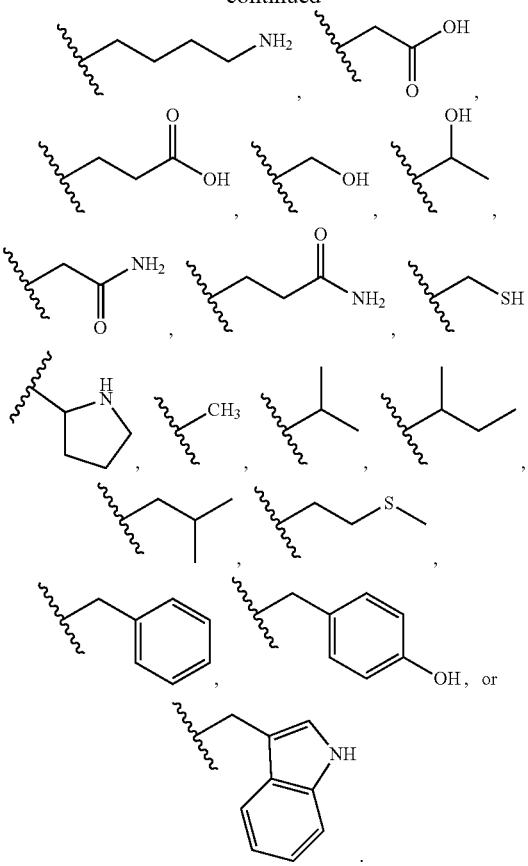

The term "non-natural amino acid side chain" refers to the functional substituent of compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium, allylalanine, 2-aminoisobutryric acid. Non-natural amino acids are non-proteinogenic amino acids that either occur naturally or are chemically synthesized. Such analogs have modified R groups (e.g., norleucine) or modified peptide backbones, but retain the same basic chemical structure as a naturally occurring amino acid. Non-limiting examples comprise exo-cis-3-aminobicyclo[2.2.1]hept-5-ene-2-carboxylic acid hydrochloride, cis-2-aminocycloheptanecarboxylic acid hydrochloride, cis-6-amino-3-cyclohexene-1-carboxylic acid hydrochloride, cis-2-amino-2-methylcyclohexanecarboxylic acid hydrochloride, cis-2-Amino-2-methylcyclopentanecarboxylic acid hydrochloride, 2-(Boc-aminomethyl)benzoic acid, 2-(Boc-amino)octanedioic acid, Boc-4,5-dehydro-Leu-OH (dicyclohexylammonium), Boc-4-(Fmoc-amino)-L-phenylalanine, Boc-β-Homopyr-OH, Boc-(2-indanyl)-Gly-OH, 4-Boc-3-morpholineacetic acid, 4-Boc-3-morpholineacetic acid, Boc-pentafluoro-D-phenylalanine, Boc-pentafluoro-L-phenylalanine, Boc-Phe(2-Br)—OH, Boc-Phe(4-Br)—OH, Boc-D-Phe(4-Br)—OH, Boc-D-Phe(3-Cl)—OH, Boc-Phe(4-NH2)-OH, Boc-Phe(3-NO2)-OH, Boc-Phe(3,5-F2)-OH, 2-(4-Boc-piperazino)-2-(3,4-dimethoxyphenyl)acetic acid purum, 2-(4-Boc-piperazino)-2-(2-fluorophenyl)acetic acid purum, 2-(4-Boc-piperazino)-2-(3-fluorophenyl)acetic acid purum, 2-(4-Boc-piperazino)-2-(4-fluorophenyl)acetic acid purum, 2-(4-Boc-piperazino)-2-(4-methoxyphenyl)acetic acid purum, 2-(4-Boc-piperazino)-2-phenylacetic acid purum, 2-(4-Boc-piperazino)-2-(3-pyridyl)acetic acid purum, 2-(4-Boc-piperazino)-2-[4-(trifluoromethyl)phenyl] acetic acid purum, Boc-β-(2-quinolyl)-Ala-OH, N—Boc-1, 2,3,6-tetrahydro-2-pyridinecarboxylic acid, Boc-3-(4-thiazolyl)-Ala-OH, Boc-3-(2-thienyl)-D-Ala-OH, Fmoc-N-(4-Boc-aminobutyl)-Gly-OH, Fmoc-N-(2-Boc-aminoethyl)-Gly-OH, Fmoc-N-(2,4-dimethoxybenzyl)-Gly-OH, Fmoc-(2-indanyl)-Gly-OH, Fmoc-pentafluoro-L-phenylalanine, Fmoc-Pen(Trt)-OH, Fmoc-Phe(2-Br)—OH, Fmoc-Phe(4-Br)—OH, Fmoc-Phe(3,5-F2)-OH, Fmoc-β-(4-thiazolyl)-Ala-OH, Fmoc-β-(2-thienyl)-Ala-OH, 4-(Hydroxymethyl)-D-phenylalanine.

"Nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a linear sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein comprise single and double stranded DNA, single and double stranded RNA, and hybrid molecules having mixtures of single and double stranded DNA and RNA. Examples of nucleic acid, e.g. polynucleotides contemplated herein comprise any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, comprising e.g., nucleic acids with a phosphothioate backbone, can comprise one or more reactive moieties. As used herein, the term reactive moiety comprises any group capable of reacting with another molecule, e.g., a nucleic acid or polypeptide through covalent, non-covalent or other interactions. By way of example, the nucleic acid can comprise an amino acid reactive moiety that reacts with an amio acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs comprise, comprise, without limitation, phosphodiester derivatives comprising, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids comprise those with positive backbones; non-ionic backbones, modified sugars, and non-ribose backbones (e.g. phosphorodiamidate morpholino oligos or locked nucleic acids (LNA) as known in the art), comprising those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also comprised within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can comprise nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanidine is cytosine. Thus, a complement may comprise a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences comprise coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

"Contacting" is used in accordance with its plain ordinary meaning and refers to the process of allowing at least two distinct species (e.g. chemical compounds comprising biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may comprise allowing two species to react, interact, or physically touch, wherein the two species may be a compound as described herein and a protein or enzyme. In some embodiments contacting comprises allowing a compound described herein to interact with a protein or enzyme that is involved in a signaling pathway.

As defined herein, the term "activation", "activate", "activating", "activator" and the like in reference to a protein-inhibitor interaction means positively affecting (e.g. increasing) the activity or function of the protein relative to the activity or function of the protein in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may comprise, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may comprise, at least in part, partially or totally increasing stimulation, increasing or enabling activation, or activating, sensitizing, or up-regulating signal transduction or enzymatic activity or the amount of a protein The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In aspects, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition comprises, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "expression" comprises any step involved in the production of the polypeptide comprising, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

An "exogenous gene," as used herein, refers to a nucleic acid within a cell that encodes a protein product, wherein the nucleic acid is not naturally present within the cell. Thus, an exogenous gene is a gene opriginating outside the cell of concern or study. For example, where an exogenous gene is within a cyanobacteria, the exogenous gene originated outside the cyanobacteria (i.e. is not naturally found in the cyanobacteria). Thus, the exogenous gene within a cyanobacteria enclosed a protein that originated outside the cyanobacteria (i.e. is not naturally foun in the cyanobacteria).

Recombinant Cyanobacterium

The present disclosure provides biosynthetic pathways for heterologous production of polyketides in bacterium host. Thus, in an aspect is provided a recombinant cyanobacterium comprising an exogenous gene capable of expressing a polyketide synthase. In embodiments, the cyanobacterium is of the genus *Synechococcus*. In embodiments, the cyanobacterium is *Synechococcus elongatus*. In embodiments, the recombinant cyanobacterium does not comprise: (i) an endogenous polyketide synthase gene, (ii) an endogenous non-ribosomal peptide synthetase gene, or (iii) an endogenous polyketide synthase gene and an endogenous non-ribosomal peptide synthetase gene.

The present disclosure provides a recombinant cyanobacterium comprising an exogenous gene capable of expressing an exogenous Sfp-type phosphopantetheinyl transferase (PPTase). In embodiments, the exogenous gene capable of expressing an exogenous Sfp-type PPTase is sfp. In embodiments, the recombinant cyanobacterium further comprises an exogenous gene capable of expressing an enzyme that catalyzes the formation of RNA from DNA in the 5'→3' direction. In embodiments, the exogenous gene capable of expressing an enzyme that catalyzes the formation of RNA from DNA in the 5'→3' direction is T7 gene 1.

In embodiments, the recombinant cyanobacterium further comprises an exogenous gene capable of expressing an exogenous carboxyacyl-CoA synthesis enzyme. In embodiments, the compound produced by the exogenous carboxyacyl-CoA synthesis enzyme is methylmalonyl-CoA, malonyl-CoA, ethylmalonyl-CoA, hydroxymalonyl-CoA, methoxymalonyl-CoA, propionyl-CoA, butyryl-CoA, isobutyryl-CoA, hexanoyl-CoA, 2-methylbutyryl-CoA, 4-aminobutanoyl-CoA, acetyl-CoA, aminomalonyl-CoA, hydroxymalonyl-CoA, benzoyl-CoA, chloroethylmalonyl-CoA, or a combination of two or more thereof. In embodiments, the exogenous carboxyacyl-CoA synthesis enzyme product is methylmalonyl-CoA. In embodiments, the exogenous carboxyacyl-CoA synthesis enzyme product is malonyl-CoA. In embodiments, the exogenous carboxyacyl-CoA synthesis enzyme product is ethylmalonyl-CoA. In embodiments, the exogenous carboxyacyl-CoA synthesis enzyme product is hydroxymalonyl-CoA. In embodiments, the exogenous carboxyacyl-CoA synthesis enzyme product is methoxymalonyl-CoA. In embodiments, the exogenous carboxyacyl-CoA synthesis enzyme product is propionyl-CoA. In embodiments, the exogenous carboxyacyl-CoA synthesis enzyme product is butyryl-CoA. In embodiments, the exogenous carboxyacyl-CoA synthesis enzyme is product isobutyryl-CoA. In embodiments, the exogenous carboxyacyl-CoA synthesis enzyme product is hexanoyl-CoA. In embodiments, the exogenous carboxyacyl-CoA synthesis enzyme product is 2-methylbutyryl-CoA. In embodiments, the exogenous carboxyacyl-CoA synthesis enzyme product is 4-aminobutanoyl-CoA. In embodiments, the exogenous carboxyacyl-CoA synthesis enzyme product is acetyl-CoA. In embodiments, the exogenous carboxyacyl-CoA synthesis enzyme product is aminomalonyl-CoA. In embodiments, the exogenous carboxyacyl-CoA synthesis enzyme product is hydroxymalonyl-CoA. In embodiments, the exogenous carboxyacyl-CoA synthesis enzyme product is benzoyl-CoA. In embodiments, the exogenous carboxyacyl-CoA synthesis enzyme product is chloroethylmalonyl-CoA. In embodiments, the exogenous carboxyacyl-CoA synthesis enzyme product is a combination of two or more carboxyacyl-CoA synthesis enzymes provided herein.

The recombinant cyanobacterium provided herein comprising embodiments thereof may comprise an exogenous gene capable of expressing an exogenous carboxyacyl-CoA synthesis enzyme. In embodiments, the exogenous gene capable of expressing an exogenous carboxyacyl-CoA synthesis enzyme comprises: (i) matB; (ii) mutA and mutB; or (iii) accA2, pccB, and pccE. In embodiments, the exogenous gene capable of expressing an exogenous carboxyacyl-CoA synthesis enzyme comprises matB. In embodiments, the exogenous gene capable of expressing an exogenous carboxyacyl-CoA synthesis enzyme comprises mutA and mutB. In embodiments, the exogenous gene capable of expressing an exogenous carboxyacyl-CoA synthesis enzyme comprises mutA. In embodiments, the exogenous gene capable of expressing an exogenous carboxyacyl-CoA synthesis enzyme comprises mutB. In embodiments, the exogenous gene capable of expressing an exogenous carboxyacyl-CoA synthesis enzyme comprises accA2, pccB, and pccE. In embodiments, the exogenous gene capable of expressing an exogenous carboxyacyl-CoA synthesis enzyme comprises accA2. In embodiments, the exogenous gene capable of expressing an exogenous carboxyacyl-CoA synthesis enzyme comprises pccB. In embodiments, the exogenous gene capable of expressing an exogenous carboxyacyl-CoA synthesis enzyme comprises pccE.

In embodiments, the recombinant cyanobacterium provided herein further comprises an exogenous gene capable of expressing an enzyme that catalyzes stereochemical inversion around an asymmetric carbon atom. In embodiments, the exogenous gene capable of expressing an enzyme that catalyzes stereochemical inversion around an asymmetric carbon atom is epimerase.

In embodiments, the recombinant cyanobacterium provided herein further comprises an exogenous gene capable of expressing a polyketide synthase. In embodiments, the exogenous gene capable of expressing a polyketide synthase is a mas gene.

In embodiments, the recombinant cyanobacterium provided herein comprises one or more plasmids comprising a plurality of genes expressing a plurality of enzymes that work together to produce a carboxyacyl-CoA compound from a carboxyacyl-CoA precursor. In embodiments, the plurality of genes comprises: (i) matB and epimerase; (ii) mutA, mutB, and epimerase; or (iii) accA2, pccB, pccE, and acsA. In embodiments, the plurality of genes comprises matB and epimerase. In embodiments, the plurality of genes comprises matB. In embodiments, the plurality of genes comprises epimerase. In embodiments, the plurality of genes comprises mutA, mutB, and epimerase. In embodiments, the plurality of genes comprises mutA. In embodiments, the plurality of genes comprises mutB. In embodiments, the plurality of genes comprises accA2, pccB, pccE, and acsA. In embodiments, the plurality of genes comprises accA2. In embodiments, the plurality of genes comprises pccB. In embodiments, the plurality of genes comprises pccE. In embodiments, the plurality of genes comprises acsA. In embodiments, the plurality of genes further comprises PconII.

In embodiments, the one or more plasmids provided herein comprises a plurality of genes, wherein the plurality of genes comprise MatB. In embodiments, the MatB gene may be a codon optimized gene. In embodiments, the one or more plasmids including the MatB gene comprises or consists of the nucleic acid sequence of SEQ ID NO:37, or a nucleic acid sequence at least 70%, 75%, 80%, 85%, 90%, or 95% identical to SEQ ID NO:37. In embodiments, the one or more plasmids including the MatB gene comprises the nucleic acid sequence of SEQ ID NO: 37, or a nucleic acid sequence at least 70%, 75%, 80%, 85%, 90%, or 95% identical to SEQ ID NO:37. In embodiments, the one or more plasmids including the MatB gene consists of the nucleic acid sequence of SEQ ID NO: 37, or a nucleic acid sequence at least 70%, 75%, 80%, 85%, 90%, or 95% identical to SEQ ID NO:37. In embodiments, the MatB gene comprises or consists of the nucleic acid sequence of SEQ ID NO:37, or a nucleic acid sequence at least 70%, 75%, 80%, 85%, 90%, or 95% identical to SEQ ID NO:37. In embodiments, the MatB gene comprises the nucleic acid sequence of SEQ ID NO: 37, or a nucleic acid sequence at least 70%, 75%, 80%, 85%, 90%, or 95% identical to SEQ ID NO:37. In embodiments, the MatB gene consists of the nucleic acid sequence of SEQ ID NO: 37, or a nucleic acid sequence at least 70%, 75%, 80%, 85%, 90%, or 95% identical to SEQ ID NO:37.

In embodiments, the one or more plasmids provided herein comprises a plurality of genes, wherein the plurality of genes comprise MutA. In embodiments, the MutA gene may be a codon optimized gene. In embodiments, the one or more plasmids including the MutA gene comprises or consists of the nucleic acid sequence of SEQ ID NO:38, or a nucleic acid sequence at least 70%, 75%, 80%, 85%, 90%, or 95% identical to SEQ ID NO:38. In embodiments, the one or more plasmids including the MutA gene comprises the nucleic acid sequence of SEQ ID NO: 38, or a nucleic acid sequence at least 70%, 75%, 80%, 85%, 90%, or 95% identical to SEQ ID NO:38. In embodiments, the one or more plasmids including the MutA gene consists of the nucleic acid sequence of SEQ ID NO: 38, or a nucleic acid sequence at least 70%, 75%, 80%, 85%, 90%, or 95% identical to SEQ ID NO:38. In embodiments, the MutA gene comprises or consists of the nucleic acid sequence of SEQ ID NO:38, or a nucleic acid sequence at least 70%, 75%, 80%, 85%, 90%, or 95% identical to SEQ ID NO:38. In embodiments, the MutA gene comprises the nucleic acid sequence of SEQ ID NO: 38, or a nucleic acid sequence at least 70%, 75%, 80%, 85%, 90%, or 95% identical to SEQ ID NO:38. In embodiments, the MutA gene consists of the nucleic acid sequence of SEQ ID NO: 38, or a nucleic acid sequence at least 70%, 75%, 80%, 85%, 90%, or 95% identical to SEQ ID NO:38.

In embodiments, the one or more plasmids provided herein comprises a plurality of genes, wherein the plurality of genes comprise MutB. In embodiments, the MutB gene may be a codon optimized gene. In embodiments, the one or more plasmids including the MutB gene comprises or consists of the nucleic acid sequence of SEQ ID NO:39, or a nucleic acid sequence at least 70%, 75%, 80%, 85%, 90%, or 95% identical to SEQ ID NO:39. In embodiments, the one or more plasmids including the MutB gene comprises the nucleic acid sequence of SEQ ID NO:39, or a nucleic acid sequence at least 70%, 75%, 80%, 85%, 90%, or 95% identical to SEQ ID NO:39. In embodiments, the one or more plasmids including the MutB gene consists of the nucleic acid sequence of SEQ ID NO: 39, or a nucleic acid sequence at least 70%, 75%, 80%, 85%, 90%, or 95% identical to SEQ ID NO:39. In embodiments, the MutB gene comprises or consists of the nucleic acid sequence of SEQ ID NO:39, or a nucleic acid sequence at least 70%, 75%, 80%, 85%, 90%, or 95% identical to SEQ ID NO:39. In embodiments, the MutB gene comprises the nucleic acid sequence of SEQ ID NO:39, or a nucleic acid sequence at least 70%, 75%, 80%, 85%, 90%, or 95% identical to SEQ ID NO:39. In embodiments, the MutB gene consists of the nucleic acid sequence of SEQ ID NO: 39, or a nucleic acid sequence at least 70%, 75%, 80%, 85%, 90%, or 95% identical to SEQ ID NO:39.

In embodiments, the one or more plasmids provided herein comprises a plurality of genes, wherein the plurality of genes comprise epimerase. In embodiments, the epimerase gene may be a codon optimized gene. In embodiments, the one or more plasmids including the epimerase gene comprises or consists of the nucleic acid sequence of SEQ ID NO:40, or a nucleic acid sequence at least 70%, 75%, 80%, 85%, 90%, or 95% identical to SEQ ID NO:40. In embodiments, the one or more plasmids including the epimerase gene comprises the nucleic acid sequence of SEQ ID NO:40, or a nucleic acid sequence at least 70%, 75%, 80%, 85%, 90%, or 95% identical to SEQ ID NO:40. In embodiments, the one or more plasmids including the epimerase gene consists of the nucleic acid sequence of SEQ ID NO:40, or a nucleic acid sequence at least 70%, 75%, 80%, 85%, 90%, or 95% identical to SEQ ID NO:40. In embodiments, the epimerase gene comprises or consists of the nucleic acid sequence of SEQ ID NO:40, or a nucleic acid sequence at least 70%, 75%, 80%, 85%, 90%, or 95% identical to SEQ ID NO40. In embodiments, the epimerase gene comprises the nucleic acid sequence of SEQ ID NO40, or a nucleic acid sequence at least 70%, 75%, 80%, 85%, 90%, or 95% identical to SEQ ID NO:40. In embodiments, the epimerase gene consists of the nucleic acid sequence of SEQ ID NO40, or a nucleic acid sequence at least 70%, 75%, 80%, 85%, 90%, or 95% identical to SEQ ID NO40.

In embodiments, the recombinant cyanobacterium comprises one or more plasmids comprising a plurality of genes expressing a plurality of enzymes that work together to produce an exogenous Sfp-type PPTase that is capable of activing a polyketide synthase enzyme. In embodiments, the polyketide synthase encoding gene is a mas gene. In embodiments, the plurality of genes comprises sfp and T7 gene 1. In embodiments, the plurality of genes comprises sfp. In embodiments, the plurality of genes comprises T7 gene 1. In embodiments, the plurality of genes further comprise PconII.

The recombinant cyanobacterium provided herein comprising embodiments thereof may produce a carboxyacyl-CoA compound. In embodiments, the recombinant cyanobacterium comprises one or more plasmids comprising a plurality of genes expressing a plurality of enzymes that work together to produce a carboxyacyl-CoA compound from a carboxyacyl-CoA precursor. In embodiments, the plurality of genes comprises: (i) matB and epimerase; (ii) mutA, mutB, and epimerase; or (iii) accA2, pccB, pccE, and acsA. In embodiments, the plurality of genes comprises matB and epimerase. In embodiments, the plurality of genes comprises matB. In embodiments, the plurality of genes comprises epimerase. In embodiments, the plurality of genes comprises mutA, mutB, and epimerase. In embodiments, the plurality of genes comprises mutA. In embodiments, the plurality of genes comprises mutB. In embodiments, the plurality of genes comprises accA2, pccB, pccE, and acsA. In embodiments, the plurality of genes comprises accA2. In embodiments, the plurality of genes comprises pccB. In embodiments, the plurality of genes comprises pccE. In embodiments, the plurality of genes comprises acsA. In embodiments, the plurality of genes further comprises PconII.

The recombinant cyanobacterium provided herein comprising embodiments thereof may produce a polyketide. In embodiments, the recombinant cyanobacteria comprises one or more plasmids comprising a plurality of genes expressing a plurality of enzymes that work together to produce a polyketide. In embodiments, the plurality of genes expressing a plurality of enzymes that work together to produce a polyketide comprise mas, fadD28, and papA5. In embodiments, the plurality of genes expressing a plurality of enzymes that work together to produce a polyketide comprise mas. In embodiments, the plurality of genes expressing a plurality of enzymes that work together to produce a polyketide comprise fadD28. In embodiments, the plurality of genes expressing a plurality of enzymes that work together to produce a polyketide comprise papA5. In embodiments, the plurality of genes further comprise a T7 promoter DNA sequence recognized by T7 RNA.

In embodiments, the recombinant cyanobacterium provided herein is a cyanobacterium of the genus *Synechococcus*. In embodiments, the cyanobacterium of the genus *Synechococcus* is *Synechococcus elongatus*. In embodiments, the *Synechococcus elongatus* is *Synechococcus elongatus* PCC 7942. In embodiments, the *Synechococcus elongatus* is *Synechococcus elongatus* AMC2302

In an aspect, a process for producing a polyketide is provided, the process comprising adding a polyketide precursor to the cyanobacterium provided herein comprising embodiments thereof. In embodiments, the polyketide precursor comprises a carboxyacyl-CoA precursor and an alcohol. In embodiments, the polyketide precursor comprises: (i) propionate, succinate, or methylmalonate, and (ii) an alcohol. In embodiments, the polyketide precursor comprises propionate. In embodiments, the polyketide precursor comprises succinate. In embodiments, the polyketide precursor comprises methylmalonate. In embodiments, the polyketide precursor comprises an alcohol. In embodiments, the polyketide precursor comprises any one of the carboxyacyl-CoA precursors provided herein and an alcohol.

The process provided herein comprising embodiments thereof may produce a polyketide, wherein the polyketide may be a therapeutic or an energy source. In embodiments, the polyketide is an antibiotic, an anti-cancer compound, or a biofuel compound. In embodiments, the polyketide is halichondrin B, pladienolide B, erythromycin, mupirocin, rapamycin, tacrolimus, or epothilone B. In embodiments, the polyketide is halichondrin B. In embodiments, the polyketide is pladienolide B. In embodiments, the polyketide is erythromycin. In embodiments, the polyketide is mupirocin. In embodiments, the polyketide is rapamycin. In embodiments, the polyketide is tacrolimus. In embodiments, the polyketide is epothilone B.

Embodiments 1-33

Embodiment 1

A recombinant cyanobacterium comprising an exogenous gene capable of expressing a polyketide synthase.

Embodiment 2

The recombinant cyanobacterium of Embodiment 1, wherein the cyanobacterium is a cyanobacterium of the genus *Synechococcus*.

Embodiment 3

A recombinant cyanobacterium comprising an exogenous gene capable of expressing an exogenous Sfp-type phosphopantetheinyl transferase (PPTase).

Embodiment 4

The recombinant cyanobacterium of Embodiment 3, wherein the exogenous gene capable of expressing an exogenous Sfp-type PPTase is sfp.

Embodiment 5

The recombinant cyanobacterium of Embodiment 3, further comprising an exogenous gene capable of expressing an enzyme that catalyzes the formation of RNA from DNA in the 5'→3' direction.

Embodiment 6

The recombinant cyanobacterium of Embodiment 5, wherein the exogenous gene capable of expressing an enzyme that catalyzes the formation of RNA from DNA in the 5'→3' direction is T7 gene 1.

Embodiment 7

The recombinant cyanobacterium of Embodiment 3, further comprising an exogenous gene capable of expressing an exogenous carboxyacyl-CoA synthesis enzyme.

Embodiment 8

The recombinant cyanobacterium of Embodiment 7, wherein the compound produced by the exogenous carboxyacyl-CoA synthesis enzyme is methylmalonyl-CoA, malonyl-CoA, ethylmalonyl-CoA, hydroxymalonyl-CoA, methoxymalonyl, CoA, propionyl-CoA, butyryl-CoA, isobutyryl-CoA, hexanoyl-CoA, 2-methylbutyryl-CoA, 4-aminobutanoyl-CoA, acetyl-CoA, aminomalonyl-CoA, hydroxymalonyl-CoA, benzoyl-CoA, chloroethylmalonyl-CoA, or a combination of two or more thereof.

Embodiment 9

The recombinant cyanobacterium of Embodiment 7, wherein the exogenous gene capable of expressing an exogenous carboxyacyl-CoA synthesis enzyme comprises: (i) matB; (ii) mutA and mutB; or (iii) accA2, pccB, and pccE.

Embodiment 10

The recombinant cyanobacterium of Embodiment 3, further comprising an exogenous gene capable of expressing an enzyme that catalyzes stereochemical inversion around an asymmetric carbon atom.

Embodiment 11

The recombinant cyanobacterium of Embodiment 10, wherein the exogenous gene capable of expressing an enzyme that catalyzes stereochemical inversion around an asymmetric carbon atom is epimerase.

Embodiment 12

The recombinant cyanobacterium of Embodiment 3, further comprising an exogenous gene capable of expressing a polyketide synthase.

Embodiment 13

The recombinant cyanobacterium of Embodiment 12, wherein the exogenous gene capable of expressing a polyketide synthase is a mas gene.

Embodiment 14

The recombinant cyanobacterium of Embodiment 3, comprising one or more plasmids comprising a plurality of genes expressing a plurality of enzymes that work together to produce a carboxyacyl-CoA compound from a carboxyacyl-CoA precursor.

Embodiment 15

The recombinant cyanobacterium of Embodiment 14, wherein the plurality of genes comprises: (i) matB and epimerase; (ii) mutA, mutB, and epimerase; or (iii) accA2, pccB, pccE, and acsA.

Embodiment 16

The recombinant cyanobacterium of Embodiment 15, wherein the plurality of genes further comprise PconII.

Embodiment 17

The recombinant cyanobacterium of Embodiment 3, comprising one or more plasmids comprising a plurality of genes expressing a plurality of enzymes that work together to produce an exogenous Sfp-type PPTase that is capable of activing a polyketide synthase gene.

Embodiment 18

The recombinant cyanobacterium of Embodiment 17, wherein the polyketide synthase gene is a mas gene.

Embodiment 19

The recombinant cyanobacterium of Embodiment 17, wherein the plurality of genes comprises sfp and T7 gene 1.

Embodiment 20

The recombinant cyanobacterium of Embodiment 19, wherein the plurality of genes further comprise PconII.

Embodiment 21

The recombinant cyanobacterium of Embodiment 3, comprising one or more plasmids comprising a plurality of genes expressing a plurality of enzymes that work together to produce a carboxyacyl-CoA compound from a carboxyacyl-CoA precursor.

Embodiment 22

The recombinant cyanobacterium of Embodiment 21, wherein the plurality of genes comprises: (i) matB and epimerase; (ii) mutA, mutB, and epimerase; or (iii) accA2, pccB, pccE, and acsA.

Embodiment 23

The recombinant cyanobacterium of Embodiment 22, wherein the plurality of genes further comprise PconII.

Embodiment 24

The recombinant cyanobacterium of Embodiment 3, comprising one or more plasmids comprising a plurality of genes expressing a plurality of enzymes that work together to produce a polyketide.

Embodiment 25

The recombinant cyanobacterium of Embodiment 24, wherein the plurality of genes expressing a plurality of enzymes that work together to produce a polyketide comprise mas, fadD28, and papA5.

Embodiment 26

The recombinant cyanobacterium of Embodiment 25, wherein the plurality of genes further comprise a T7 promoter DNA sequence recognized by T7 RNA polymerase.

Embodiment 27

The recombinant cyanobacterium of Embodiment 3, wherein the cyanobacterium is a cyanobacterium of the genus *Synechococcus*.

Embodiment 28

The recombinant cyanobacterium of Embodiment 2 or 27, wherein the cyanobacterium of the genus *Synechococcus* is *Synechococcus elongatus*.

Embodiment 29

A process for producing a polyketide, the process comprising adding a polyketide precursor to the cyanobacterium of Embodiment 3.

Embodiment 30

The process of Embodiment 29, wherein the polyketide precursor comprises a carboxyacyl-CoA precursor and an alcohol.

Embodiment 31

The process of Embodiment 29, wherein the polyketide precursor comprises: (i) propionate, succinate, or methylmalonate, and (ii) an alcohol.

Embodiment 32

The process of Embodiment 29, wherein the polyketide is an antibiotic, an anti-cancer compound, or a biofuel compound.

Embodiment 33

The process of Embodiment 29, wherein the polyketide is halichondrin B, pladienolide B, erythromycin, mupirocin, rapamycin, tacrolimus, or epothilone B.

Embodiments P1-P9

Embodiment P1

A *Synechococcus* bacteria comprising a heterologous carboxylase complex.

Embodiment P2

The method of Embodiment 1 wherein said *Synechococcus* bacteria is *Synechococcus elongatus* PCC 7942.

Embodiment P3

The method of Embodiment 1 wherein said heterologous carboxylase complex is a *Streptomyces* carboxylase complex.

Embodiment P4

The method of Embodiment 1 wherein said *Streptomyces* carboxylase complex is acetyl-CoA carboxylase complex (ACC) or propionyl-CoA carboxylase complex (PCC).

Embodiment P5

A *Synechococcus* bacteria comprising a heterologous methylmalonyl-CoA mutase or a heterologous methylmalonyl-CoA epimerase.

Embodiment P6

The method of Embodiment 5 wherein said methylmalonyl-CoA mutase or methylmalonyl-CoA epimerase is a *Propionibacteria shermanii* methylmalonyl-CoA mutase or methylmalonyl-CoA epimerase.

Embodiment P7

The method of Embodiment 5 wherein said *Synechococcus* bacteria comprises said methylmalonyl-CoA mutase and said methylmalonyl-CoA epimerase.

Embodiment P8

The method of Embodiment 5 wherein said *Synechococcus* bacteria is *Synechococcus elongatus* PCC 7942.

Embodiment P9

A method of making (2S)-methylmalonyl-CoA using said *Synechococcus* bacteria of Embodiment 1 or 2.

EXAMPLE

Background to Examples

Increasing efforts are being made to develop a microbial bio-based transformation of inexpensive renewable feedstocks into specialty chemicals, valuable drugs and fuels. In this context, photosynthetic microorganisms signify an attractive alternative as they can convert $CO_2$ bypassing the need of, for example, plant biomass deconstruction. In particular, cyanobacteria are the only prokaryotes that perform plant-like oxygenic photosynthesis efficiently converting sunlight-derived energy and atmospheric carbon into biomass. Indeed, these microorganisms have higher photosynthesis and biomass production rates compared to plants and can convert up to 3-9% of the solar energy into biomass compared to ≤0.25-3% achieved by crops (Ducat et al. 2011). Furthermore, characterized standard genetic parts and devices, of the sort that are now available for cyanobacteria, make metabolic engineering of these microorganisms more predictable and allow construction and integration of larger metabolic systems (Taton et al. 2014). The unicellular cyanobacterium *Synechococcus elongatus* PCC 7942 represents a model strain for this purpose because of its genetic tractability and short life-cycle compared to other cyanobacterial species. *S. elongatus* PCC 7942 was developed as a photosynthetic biocatalyst for the synthesis of an array of industrial compounds such as isobutyraldehyde (Atsumi et al. 2009) and 2,3-butanediol (Oliver J W et al. 2013).

In this context, the genetic tractability and the favorable large-scale outdoor pond culture properties of cyanobacteria *Leptolyngbya* BL0902 and *Synechococcus elongatus* PCC 7942 make them attractive candidate hosts for production of polyketide-derived oleochemicals. However, since these cyanobacteria do not naturally produce polyketides, they do not contain or express many of the biosynthetic pathways necessary for polyketide biosynthesis. Therefore, one objective was moving a different set of genes into these hosts to provide these bacteria with the ability to produce methylmalonyl-CoA and malonyl-CoA derived compounds.

Cyanobacteria are a diverse set of species unified by a common theme: sunlight, energy, and $CO_2$ combined to produce an unrivaled array of useful products. The cyanobacteria strains described herein may be useful not only to produce methyl-branched waxes, but also could be used as a platform for the production of other polyketides.

Complex polyketides comprise a family of natural products that possess a wide variety of pharmacological or biological activities. Numerous polyketides and their semi-synthetic derivatives have been approved for clinical use in humans or animals, comprising antibiotics, antifungal agents, immunosuppressants, antiparasitic agents and insecticides, with annual sales exceeding $20B USD (Yuzawa et al., The Journal of Antibiotics (2016), 1-8). All these natural products share a common mechanism of biosynthesis and are produced by a class of enzymes called polyketide synthases (PKS). These enzymes can condense and reduce a small series of acyl-CoA precursors, the most common being acetyl-CoA, propionyl-CoA, malonyl-CoA and methylmalonyl-CoA, to build the polyketide backbone in a step-wise manner that resembles fatty acid biosynthesis.

Since the first example of a heterologous production of a polyketide molecule in *Escherichia coli* (Pfeifer, Science 2001), continuing achievements in understanding and manipulating polyketide biosynthesis, along with the availability of new genomic and genetic tools, has greatly facilitated the ability to reconstitute these multistep catalytic processes in new heterologous hosts (Kim et al. Natural product reports. 2016; 33(8):933-41).

In the present disclosure, inter alia, the inventors established the viability of *S. elongatus* PCC 7942 as a polyketide production platform. As a proof of concept, the inventors focused on the mycobacterial PKS mycocerosic acid (MAS) pathway, previously demonstrated in *E. coli* for the production of multimethyl-branched wax esters (MBE) (Menendez-Bravo et al 2014). For this effort and to allow a versatile, interchangeable and combinatorial construction of the desired cyanobacterial strains, three independent and interchangeable modules were designed and constructed. Each module comprised a set of enzymes to perform the specific functions needed for the heterologous production of polyketides in this host.

A biosynthetic pathway was developed that is based on an iterative PKS system in order to produce multi-methyl branched fatty acids (MBFA) and ester derivatives (MBE) (Menendez-Bravo et al. 2014). This system comprises a PKS called Mycocerosic acid synthase (MAS), an acyl-AMP ligase Faal28, and an acyltransferase called PapA5. MAS carries out the biosynthesis of the multi methyl-branched fatty acids by the iterative elongation of $C_{18\text{-}20}$ fatty acids starters with methylmalonyl-CoA extender units (Mathur & Kolattukudy 1992) (Trivedi et al. 2005). Faal28 activates fatty acids as acyl-adenylates which are the MAS "starting" substrates (medium- to long-chain fatty acids), and the PapA5 protein can directly transfer the MBFA from MAS protein to alcohols (Onwueme et al. 2004). This metabolic pathway was designed in an *E. coli* recombinant strain which has also been genetically adapted to produce the PKS substrate (2S)-methylmalonyl-CoA by expressing the *Streptomyces coelicolor* propionyl-CoA carboxylase (PCC) complex subunits AccA2 and PccB (Murli et al. 2003). Lipids produced by this system have greater steric hindrance than linear fatty acids and a higher chemical stability compared to polyunsaturated fatty acids, maintaining excellent low temperature properties (Hammond et al.

1995). These lipid compounds may be used in the biolubricants, pharmaceuticals and cosmetics industries.

Exemplary Studies

Design and development of modular pathways for the production of PKS-derived biochemicals in *S. elongatus*

Considering the advantages of using cyanobacteria as a platform for high-valued molecules production, and since *S. elongatus* PCC 7942 has shown to be an excellent model organism for genetic engineering, the inventors tested this strain as a suitable heterologous host for the biosynthesis of PKS-derived compounds. To this end, the recombinant strain was designed to: (i) produce the appropriate PKS carboxyacyl-CoA substrates (extender units); (ii) carry out the post-translational modification of the heterologous PKS ACP domain(s); and (iii) harbor a robust and preferably regulated expression system for the often large and polycistronic PKS gene clusters. Therefore, the inventors designed and constructed three independent interchangeable and combinable modules as shown in FIG. 1. Each module comprised a set of enzymes to perform the specific functions listed above. Module I is dedicated to the production of different carboxyacyl-CoAs used as PKS substrates through alternative routes. Module II comprises a T7 RNA polymerase (T7RNAP) for the robust and controlled expression of a PKS gene cluster driven by a T7 promoter, and a promiscuous phosphopantetheinyl transferase (PPTase) for the post-translational modification of the PKS. Finally, module III harbors the PKS gene cluster driven by a T7 promoter.

Figure 16:
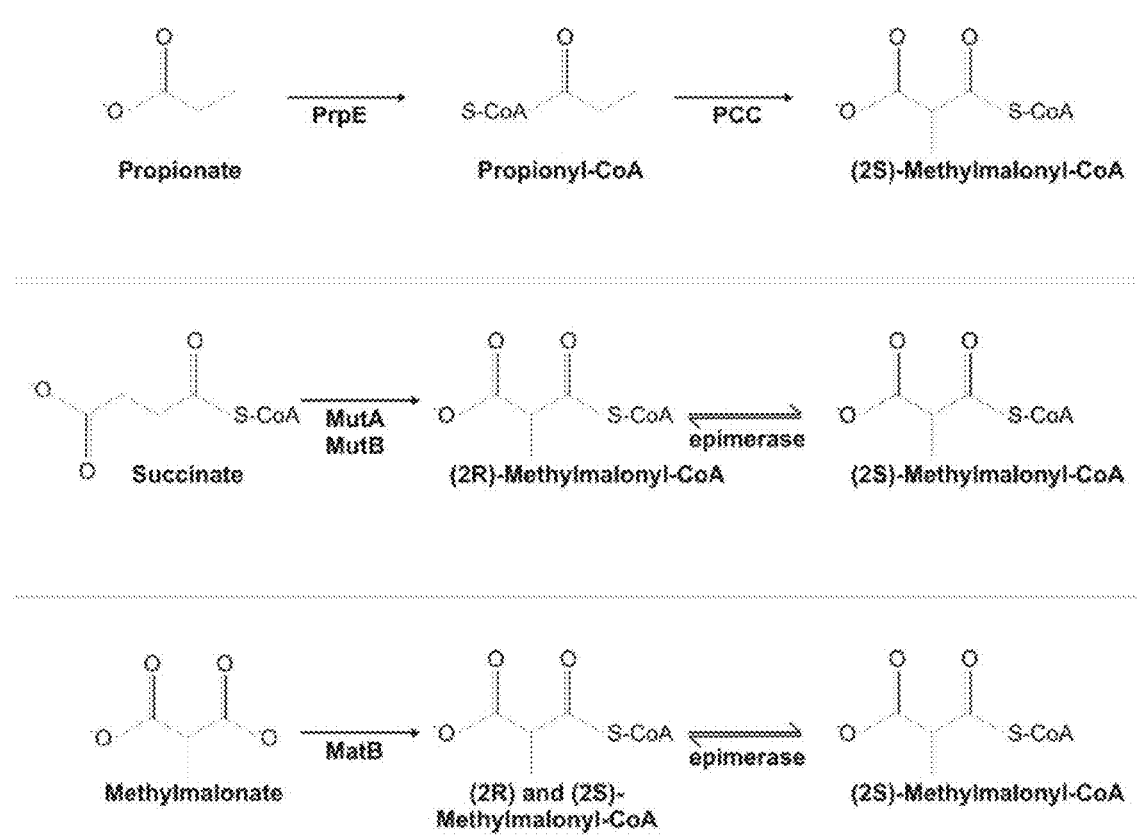
FIG. 16 shows three different (2S)-methylmalonyl-CoA biosynthetic pathways tested in Module I of the biosynthetic platform.

Considering that many industrially relevant polyketides use malonyl-CoA, methylmalonyl-CoA and/or ethylmalonyl-CoA as substrates, three different pathways capable of generating these carboxyacyl-CoAs were designed as Module I. The three biosynthetic pathways are illustrated in FIG. 16. The first pathway involves matB from *Streptomyces coelicolor* and the epimerase (epi) gene from *Propionibacterium shermanii*. MatB is an acyl-CoA synthetase (An JH & Kim Y S et al. 1998; Hughes & Keatinge-Clay 2011) with a relaxed substrate specificity that allows the in vitro synthesis of different PKS's extender units such as malonyl-CoA, methylmalonyl-CoA, ethylmalonyl-CoA, hydroxymalonyl-CoA and methoxymalonyl-CoA, from the corresponding carboxylic acid substrates (Hughes & Keatinge-Clay 2011). The broad substrate specificity of this enzyme would contribute to the versatility of the platform strain because it would enable the intracellular production of more than one PKS extender unit, depending on the exogenous supply of the carboxylic acid. Since PKSs recognize only the 2S isomer of the α-substituted carboxyacyl-CoAs and considering that MatB produces a racemic mixture of them, the epimerization of (2R)-α-substituted extender units formed by MatB would increase availability of the correct 2S isomer before they can be accepted by the PKS acyltransferase domains. In this sense, the inventors co-expressed the methylmalonyl-CoA epimerase (epi) from *P. shermanii* (Dayem et al. 2002) to shift the equilibrium of the reaction towards the correct 2S isomer and therefore to improve the production of the final polyketide. Hereafter this module will be named as module IA (FIG. 1).

The second pathway toward methylmalonyl-CoA production involves the sequential action of two enzymes, methylmalonyl-CoA mutase complex (mutAB) and methylmalonyl-CoA epimerase from *P. shermanii*, which convert succinyl-CoA to (2R)-methylmalonyl-CoA and then to (2S)-methylmalonyl-CoA. This biosynthetic route was designed as module IB (FIG. 1). Genome scale metabolic predictions together with data on gene essentiality (Broddrick et al 2016) showed the importance of a linear, noncyclic TCA pathway for *S. elongatus*, with no evidence of succinyl-CoA as intermediate. Since MutAB's substrate is succinyl-CoA, in this case a succinyl-CoA synthetase must be co-expressed.

The third pathway involves the *S. coelicolor* propionyl-CoA carboxylase (PCC) complex, which comprises the AccA2, PccB and PccE subunits. This enzyme complex has also been demonstrated to have a relaxed substrate specificity in vitro, being able to produce (2S)-methylmalonyl-CoA and (2S)-ethylmalonyl-CoA from their corresponding substrates, propionyl-CoA and butyryl-CoA, respectively. This module was named IC (FIG. 1).

Because the PCC substrate, propionyl-CoA, is not readily available in most bacteria, the PCC biosynthetic route requires an exogenous supply of propionate, which has to be further converted into propionyl-CoA. Inventors hypothesized that this step could be performed by a *S. elongatus* native acetyl-CoA synthetase/acetyl-CoA ligase (AcsA, SynPCC7942_1352) because its orthologous protein from *Synechococcus* sp. PCC 7002 showed in vitro CoA ligase activities towards various organic acids, comprising acetate and propionate (Matthew B. Begemann et al. 2013).

The genes encoding MatB, MutAB and the PCC complex were cloned in a cyanobacterial expression vector derived from *S. elongatus* pANS replicon (You Chen et al. 2016) and were expressed from a synthetic *E. coli* constitutive promoter, PconII (Table 1) (Elledge and Davis et al. 1989; Taton et al. 2014). The epi gene was also cloned downstream of PconII but in an integrative vector that recombines in the neutral site NS2 of the *S. elongatus* genome (Table 1) (Clerico et al 2007).

TABLE 1

Plasmids developed

| Plasmid | Description | Antibiotic resistance |
|---|---|---|
| pJR03 | pANS-aadAI-PconII-matB | Sp Sm |
| pJR04 | NS2TC-aphI-PconII-epimerase | Tc Km |
| pJR05 | pANS-aadAI-PconII-mutA-mutB | Sp Sm |
| pJR06 | pANS-aadAI-PconII-accA2-pccB-pccE | Sp Sm |
| pJR07 | NS1-nat1-pT7-papA5-fadD28-mas | Nt |
| pJR08 | NS3-aacC1-PconII-rswF-sfp-PconII-rswF-T7RNAP | Gm |
| pJR09 | NS3-aacC1-PconII-rswF-sfp-PconII6-rswB-T7RNAP | Gm |

Figure 17:
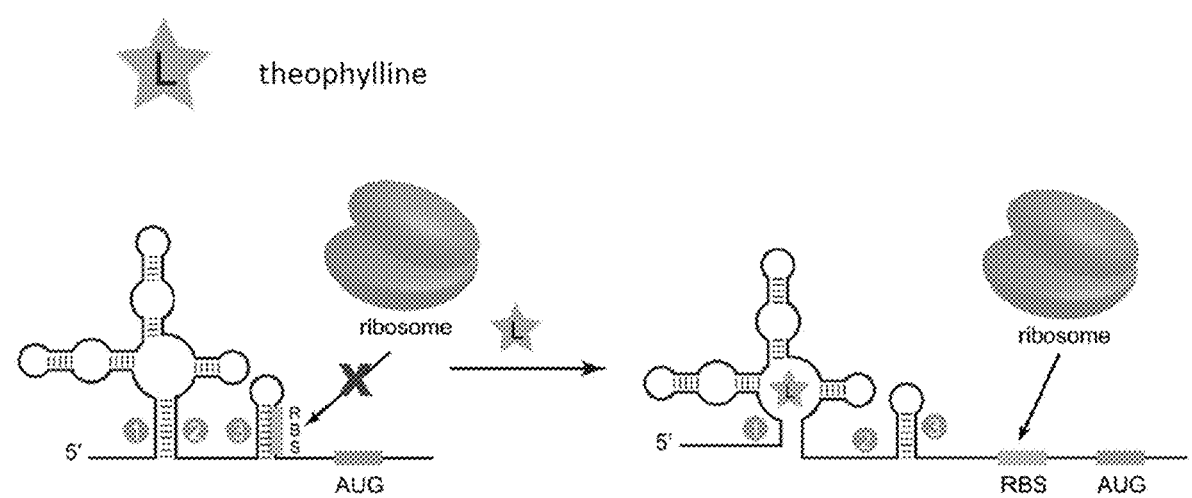
FIG. 17 is a schematic showing a theophylline inducible riboswitch regulation as used in Module II of the biosynthetic platform.

Module II was designed to enable the orthogonal expression of the PKS biosynthetic gene cluster and the post-translational modification of the acyl carrier protein domain (ACP) of the PKS. A variety of constitutive and inducible expression systems have been used in *S. elongatus*, but compared to most applications, the expression of PKS gene clusters presents additional challenges. PKSs are often arranged as large polycistronic transcriptional units. In addition, although low levels of expression may be essential in some cases, several studies suggested that the biosynthesis of polyketides and other bioactive secondary metabolites (at detectable levels) may require the use of strong promoters. Therefore, inventors hypothesized that a controlled T7 expression system would be well suited for the expression of PKS gene clusters and could be engineered in *S. elongatus*. Typically, the T7 RNA polymerase encoding gene is under the control of a derivative of the lac promoter which is tightly regulated by LacI (Dubendorff and Studier 1991). IPTG inducible promoter systems have been used in cyanobacteria, but in *S. elongatus* in particular, however, they usually exhibit high basal activity levels in the absence of inducer and poor induction ratios (Huang et al 2010; Ma et al 2014). In comparison, theophylline inducible riboswitches that control translation initiation appear to provide a much tighter control of gene expression with higher induction ratios (Ma et al 2014). Therefore, for a better control of the T7 RNA polymerase expression, the inventors constructed expression devices where the transcription of the T7 RNA polymerase was driven by two different variants of the conII promoter (Tieu et al in prep), while the translation of the T7 RNA polymerase was controlled by theophylline dependent riboswitches (see below), as illustrated in FIG. 17.

For the post-translational modification of ACP domains within PKSs, a 4'-phosphopantetheinyl transferase (PPTase) activity is essential to catalyze the addition of the 4'-phosphopantetheine (PPant) moiety onto this domain to generate its active holo form (Quadri et al. 1998, Beld et al. 2014). S. elongatus genome does not encode polyketide or non-ribosomal peptide clusters, although a Sfp-type PPTase was identified in its genome. Further characterization of this PPTase showed that it exhibits very low or no activity towards ACPs of different PKSs (Yang et al 2017). Therefore, as part of this module, inventors constructed a device where the promiscuous Sfp-PPTase from Bacillus subtilis (Quadri et al. 1998) was expressed from Pcon placed under the translational control of riboswitch F (FIG. 1).

Module III is specifically dedicated to the enzymes involved in the biosynthesis of a final product. Here, inventors focused on the production of multimethyl-branched wax esters (MBE) using the mycocerosic polyketide synthase-based biosynthetic pathway from Mycobacterium tuberculosis, which relies on the successful expression of FadD28, Mas and PapA5 (Menendez-Bravo et al 2014). The three coding sequences of these enzymes were cloned in an operon fashion downstream the T7 promoter ($P_{T7}$) (FIG. 1).

Development of inducible T7 expression systems controlled by theophylline riboswitches in S. elongatus.

To establish a functional and inducible T7RNAP based expression system for S. elongatus, devices were constructed where the transcription of the T7 RNA polymerase was driven by the conII promoter and its translation was controlled by either the theophylline dependent riboswitches B or F (Ma et al 2014). Both riboswitches had previously showed an elevated induction ratio when proved in a direct PconII-YFP construction; while riboswitch F enabled a higher level of expression after induction, riboswitch B provided a tighter control with a lower uninduced level of expression (Ma et al 2014). Thus, the potentiality of these regulatory devices when using a TRNAP expression system in S. elongatus was studied. Initially, the inventors constructed a reporter device in which the YFP reporter gene was driven by the $P_{T7}$ and the T7RNAP expression was left under the control of a PconII-riboswitch (B or F). Both the T7RNAP expression systems and the reporter PT7-YFP were independently integrated at NS1 and NS2 of S. elongatus chromosome (Clerico et al 2007). The experiment showed that the two strains analyzed, containing the PconII-T7 RNA pol and either the riboswitch B or F, had high levels of YFP (up to 5.3 YFP fluorescence) in the absence of the inducer and did not show a clear response to the addition of theophyline (data not shown). Therefore, and in order to reduce the background levels of the T7 RNA polymerase, and hence of YFP, a mutated version of the PconJ (Tieu et al., in prep) was analyzed to drive the T7RNAP expression. This targeted mutation in the −10 sequence of the $P_{conII}$ (indicated as PconII*) led to a significantly lower basal levels of YFP fluorescence in uninduced strains and to a clear dose dependent response of the YFP expression when theophyllin was added at different concentrations, either with riboswitch B or F.

Although highest levels of YFP expression were similar with the two riboswitches under study, lower concentrations of theophylline (1 mM instead of 2 mM) were needed for the riboswitch F to reach maximal fluorescence. On the other hand, riboswitch B showed a tighter control in the absence of the inducer. Having analyzed the different alternative devices developed, the original $P_{conII}$ and riboswitch F device were believed to produce the highest $P_{T7}$ activity while the mutated $P_{conII}$ and riboswitch B device were believed to enable a tighter control of the $P_{T7}$ activity and an optimal dose response of the system. Accordingly, these devices were placed in module IIA and IIB, respectively (FIG. 1).

Construction of S. elongatus recombinant strains and assessment of protein expression.

Figure 7A:
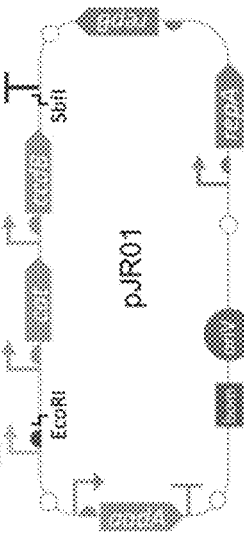
FIGS. 7A-7B show schematics of genes and vectors for each module of the cyanobacterial polyketide production platform.
Figure 7B:
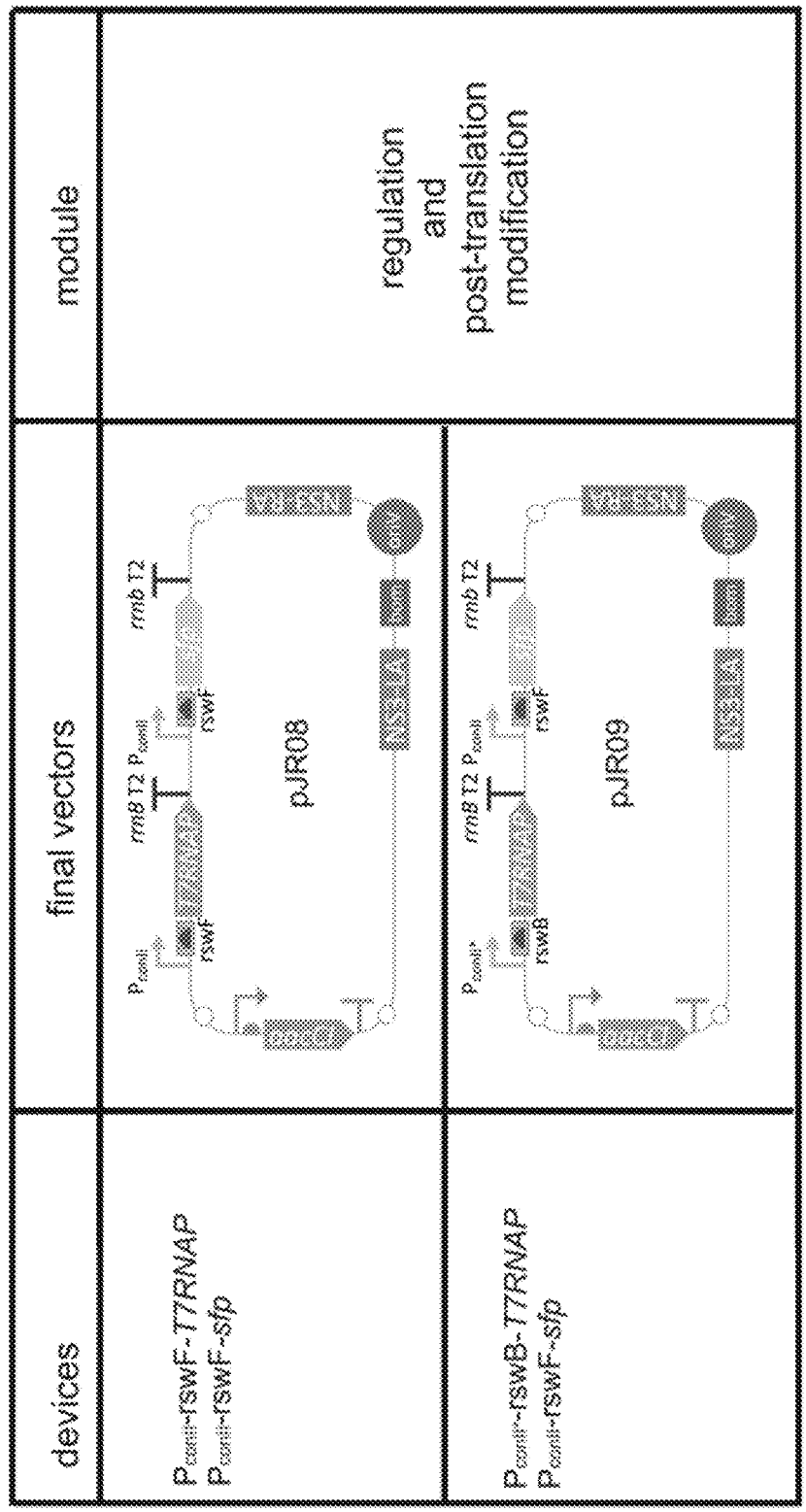

Using recently developed synthetic biology tools for cyanobacteria (Taton et al. 2014), the inventors built all functional modules in compatible vectors, as illustrated in FIGS. 7A-7B. As shown in FIG. 7A, the extender unit production module, two compatible shuttle vectors were constructed as destination vectors: pJR01, which contains a replicon for S. elongatus (comprising repA and repB from pANS), an E. coli origin of replication (oriV) and an origin of transfer (bom) from pBR322, a spectinomycin/streptomycin resistance (SpR+SmR) gene (aadA), and an expression device with the conII promoter ($P_{conII}$), a ribosomal binding site (RBS), a replaceable cloning cassette (cat-ccdB), and a transcription terminator sequence (rrnb T2). The cat-893 ccdB cloning cassette harbors a chloramphenicol resistance (CmR) marker (cat) and the ccdB toxic gene1, which is lethal to most E. coli cell lines, flanked with restriction sites. This cassette simplifies the cloning of desired DNA fragments (e.g. matB, mutA-mutB, 896 accA2-pccB-pccE) because it prevents the growth of cells transformed with undigested vector. pJR02, which contains homologous recombination sequences for chromosomal integration into S. elongatus neutral site 2 (NS2), an E. coli origin of replication and an origin of transfer, a kanamycin resistance (KmR) gene (aphI), and the expression device ($P_{conII}$-cat-ccdB) described for pJR01. This vector was constructed to express additional enzymes required for the production of extender units such as the epimerase encoding gene. For the polyketide production module, pCV0064 was used as backbone. This plasmid contains homologous recombination sequences for chromosomal integration into S. elongatus neutral site 1 (NS1), an E. coli origin of replication and the RK2 bom site, a nourseothricin resistance (NtR) gene (nat), previously codon optimized for S. elongatus, and a replaceable cloning cassette with the ccdB toxic gene flanked with restriction sites and terminator sequences. In this work, the PT7-papA5-fadD28-mas 908 reconstituted gene cluster was assembled in the pCV0064 backbone. As shown in FIG. 7B, for the regulation and post-translation modification module, two different plasmids carrying the T7RNAP and sfp genes were constructed, pJR08 and pJR09. Both plasmids share the same backbone, which contains homologous recombination sequences for chromosomal integration into S. elongatus neutral site 3 (NS3), an E. coli origin of replication and a bom site, and a gentamycin resistance (GmR) gene (aacCI). The expression of sfp is driven by $P_{conII}$ and its translation is controlled by the theophylline inducible riboswitch F in both plasmids. For pJR08, the T7RNAP is expressed from $P_{conII}$ and its translation controlled by the theophylline-inducible riboswitch F. For pJR09, the T7RNAP is expressed from the mutated $P_{conII}$ ($P_{conII}$*) and its translation controlled by the theophylline-inducible riboswitch B.

The recombinant cyanobacterial strains described in Table 2 were obtained by sequential transformation with the indicated recombinant vectors. Each of the final six recombinant strains constructed carried a different combination of modules I, II and III.

Functional Analysis of the Phosphopantetheinyl Transferase (PPTase) Activity in *S. Elongatus*

Figure 8A:
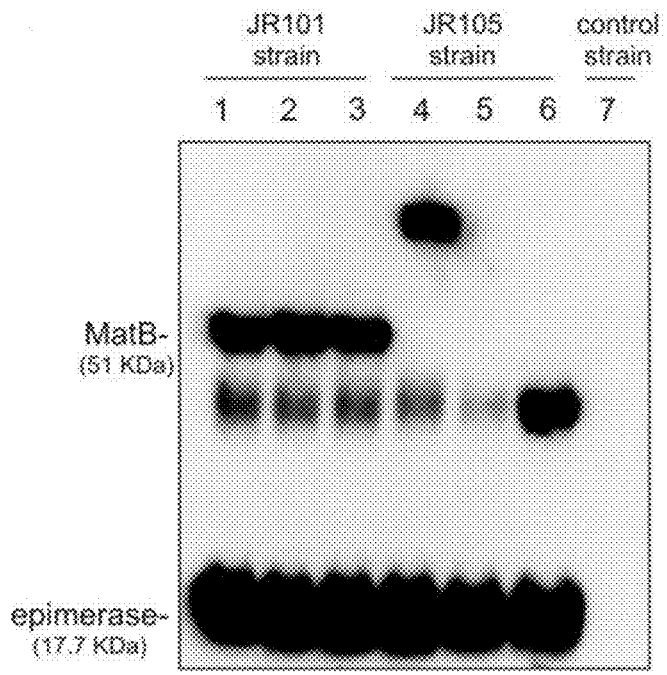
FIGS. 8A-8B show western-blot analysis of proteins expressed from module IA and IB.
Figure 8B:
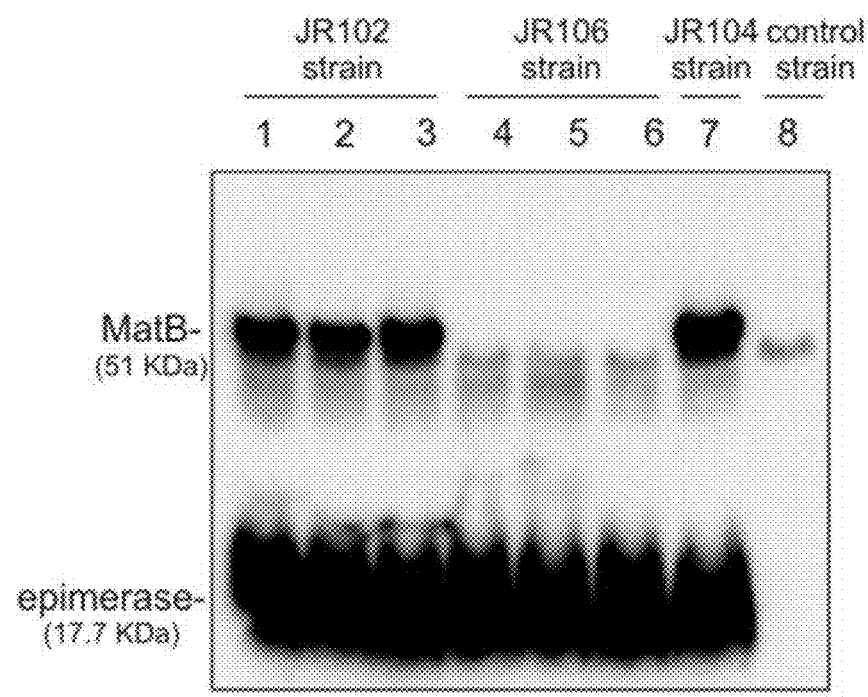
Figure 9:
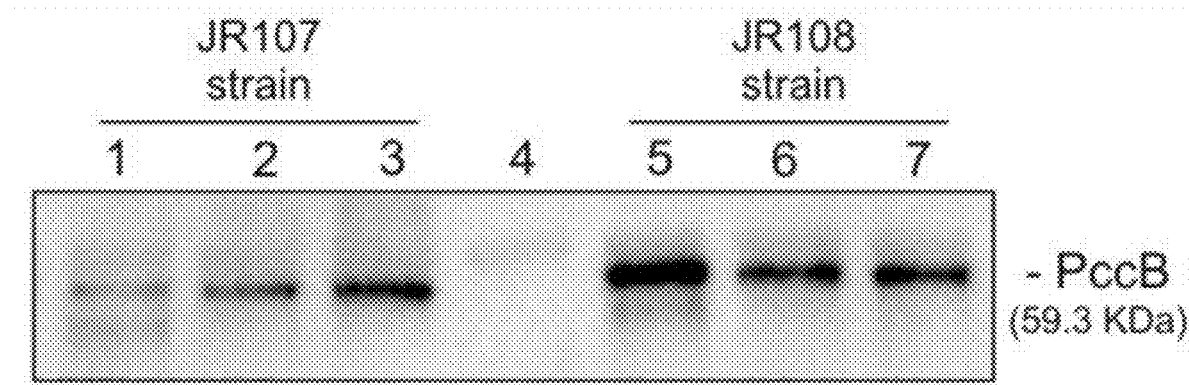
FIG. 9 shows western-blot analysis of the PccB subunit of the PCC complex expressed from module IC. Immunoblot of soluble protein extracts from three independent clones of the *S. elongatus* AMC2302 recombinant strains: JR107 (lanes 1, 2, 3) and JR108 (lanes 5, 6, 7), and the wild-type strain (lane 4). The expression of the PccB subunit of the PCC complex was detected with anti-PccB antibodies2.
Figure 10A:
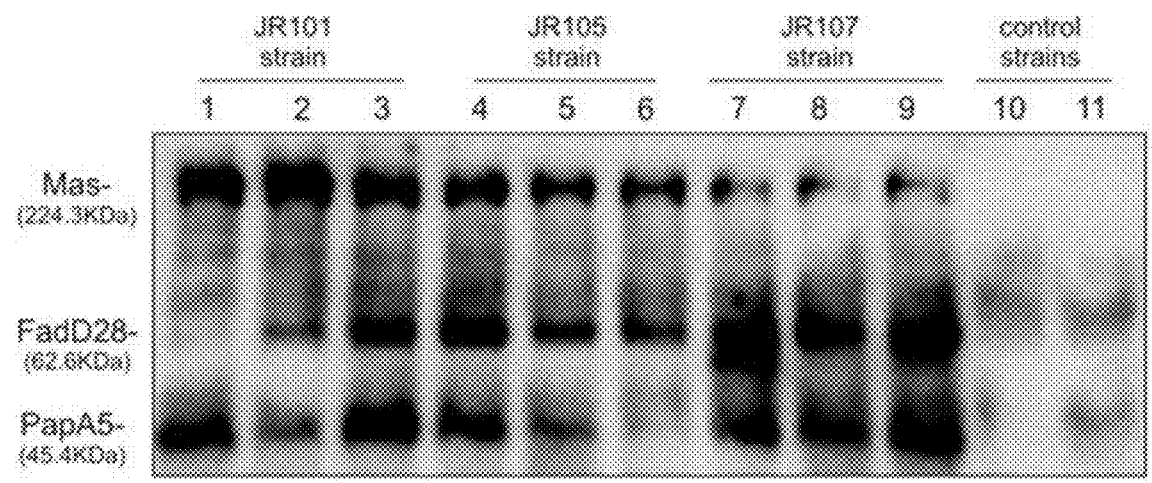
FIGS. 10A-10B show western-blot analysis of proteins expressed from module III.
Figure 10B:
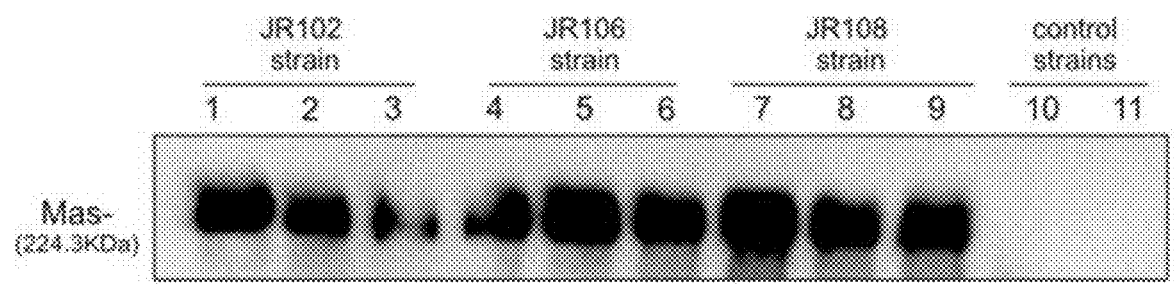

The heterologous proteins that were involved in the biosynthesis of methylmalonyl-CoA (Module I) comprising MatB, the MutA-MutB subunits and the epimerase were tagged for Western blot analyses. These assays indicated that MutA was not expressed properly in *S. elongatus* strains (FIGS. 8A-8B), consequently inventors did not pursue any further development of these strains. On the other hand, MatB and the epimerase were properly expressed with the expected molecular weights on the corresponding Western blots (FIGS. 8A-8B). Also the PccB subunit of the PCC complex was analyzed with a specific anti-PccB antibody and showed correct expression (FIG. 9). The three enzymes of the PKS pathway, namely PapA5, FadD28 and Mas, were also tagged and were detected as soluble proteins in the cyanobacterial strains by Western blot analyses (FIGS. 10A-10B). These results showed that *S. elongatus*, which does not have PKS genes in its genome, is capable of expressing a complex heterologous pathway comprising the Mas protein, a large multidomain PKS enzyme. In addition, the fact that the Mas pathway was expressed in these recombinant cyanobacterial strains also indicates that the riboswitch-regulated T7RNAP system constructed here is functional, and can successfully drive the expression of the genes cloned in module III.

Figure 2A:
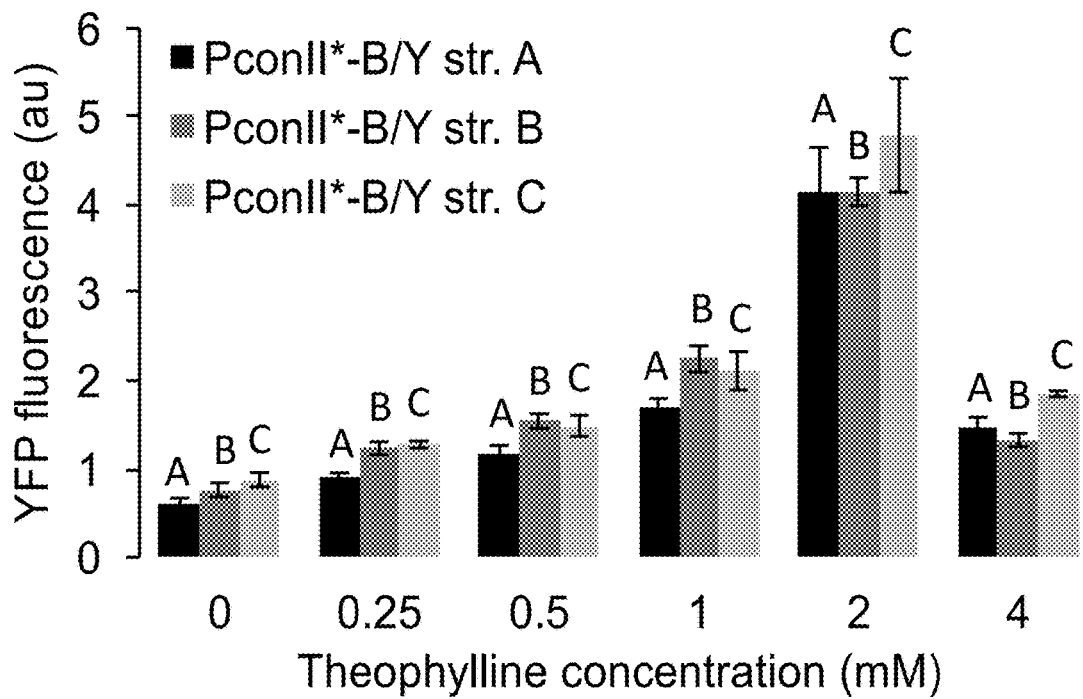
FIGS. 2A-2B show characterization of inducible T7 expression systems in *S. elongatus* at different theophylline concentrations. The expression of the T7RNAP was driven by a mutated PconII* and was translationally controlled by riboswitch B (FIG. 2A) or riboswitch F (FIG. 2B). YFP fluorescence served as an easily readable output. Three independent strains were analyzed for each construct and error bars indicate standard deviations of the replicates.
Figure 2B:
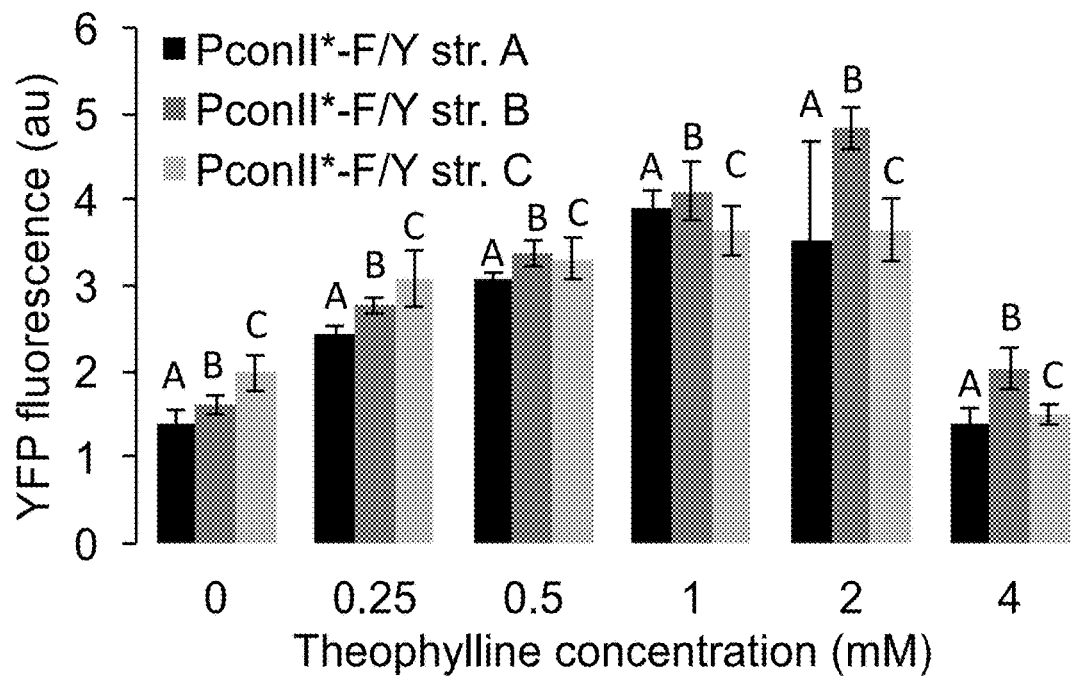
Figure 11:
FIG. 11 is an image of an SDS-PAGE gel showing the functional PPTase Sfp using an in vitro assay detecting *E. coli* ACP phosphopantetheinylation with fluorescently labeled CoA (TAMRA-CoA). Proteins were separated by SDS-PAGE and visualized by UV fluorescence. Lanes 1, 2, 3, 4, 5, 6, 7, 8, 9, 10, 11 were loaded with purified *E. coli* ACP plus TAMRA-CoA and soluble protein extracts from three independent clones of each of the *S. elongatus* recombinant strains: JR101 (lanes 1, 2, 3), JR103 (lane 4), JR107 (lanes 5, 6, 7), JR108 (lanes 8, 9, 10), and JR109 (without module II and III) (lane 11). Purified *E. coli* ACP plus TAMRA-CoA and with the soluble protein extract of the wild-type strain (lane 12) and with purified Sfp (lane 13) served as negative and positive controls, respectively.

To assay for Sfp expression and functional activity, the type II *E. coli* fatty acid synthase ACP (AcpP) was mixed with afluorescently labeled pantetheine analogue (TAMRA-CoA) (La Clair, et al. (2004) Chem Biol, 11:195-201). Protein extract from each recombinant cyanobacteria containing the heterologous Sfp enzyme or from *S. elongatus* WT strain AMC2302 were added to recombinant apo-AcpP in the presence of TAMRA-CoA. The detection of the ACP phosphopantetheinylation was carried out on SDS-PAGE; the reporter-labeled ACP was visualized by UV fluorescence (FIG. 2 and FIG. 11). As shown in FIG. 2, protein extracts from all the recombinant cyanobacteria strains constructed here allowed the conversion of *E. coli* ACP to its fluorescently labeled derivative. These results indicate that *S. elongatus* WT strain AMC2302 does not have a detectable PPTase activity and that Sfp is expressed in its active form in *S. elongatus* recombinant strains. These results reveal the relevance of having a promiscuous PPTase activity in the cyanobacterial polyketide production platform constructed. Considering that Sfp has a very relaxed specificity towards different (PKS) ACP domains, the fact that inventors showed that it is functional in *S. elongatus* recombinant strains protein extracts, and that inventors have shown Mas is a suitable substrate for Sfp (Ishikawa, et al. Journal of the American Chemical Society. 2011 Dec. 29; 134(2):769-72), the inventors were confident that Mas enzyme would be adequately phosphopantetheinylated in the recombinant strains here developed.

Production of Multi-Methyl-Branched Esters Derived from Methylmalonyl-CoA by *S. elongates*.

After the inventors confirmed the expression of the key proteins encoded by module I, II and III, these strains were further analyzed for the production of MBE. Bioconversion assays were performed on 4 different strains: MatB F pfm (modules IA+IIA+III), MatB B6 pfm (modules IA+IIB+III), PCC F pfm (modules IC+IIA+III), and PCC B6 pfm (modules IC+IB+III).

TABLE 2

*S. elongatus* strains

| Strain | Genotype | Antibiotic resistance |
| --- | --- | --- |
| AMC2302 | *S. elongatus* PCC7942 WT strain curated from the small pANS plasmid | |
| MatB F pfm | AMC2302; pANS-aadAI-PconII-matB; NS2TC::aphI-PconII-epimerase; NS1::nat1-pT7-papA5-fadD28-mas; NS3::aacC1-PconII-rswF-sfp-PconII-rswF-T7RNAP | Sp Sm Km Nt Gm |
| MatB B6 pfm | AMC2302; pANS-aadAI-PconII-matB; NS2TC::aphI-PconII-epimerase; NS1::nat1-pT7-papA5-fadD28-mas; NS3::aacC1-PconII-rswF-sfp-PconII6-rswB-T7RNAP | Sp Sm Km Nt Gm |
| MatB F | AMC2302; pANS-aadAI-PconII-matB; NS2TC::aphI-PconII-epimerase; NS3::aacC1-PconII-rswF-sfp-PconII-rswF-T7RNAP | Sp Sm Km Gm |
| MatB B6 | AMC2302; pANS-aadAI-PconII-matB; NS2TC::aphI-PconII-epimerase; NS3::aacC1-PconII-rswF-sfp-PconII6-rswB-T7RNAP | Sp Sm Km Gm |
| MutAB F pfm | AMC2302; pANS-aadAI-PconII-mutA-mutB; NS2TC::aphI-PconII-epimerase; NS1::nat1-pT7-papA5-fadD28-mas; NS3::aacC1-PconII-rswF-sfp-PconII-rswF-T7RNAP | Sp Sm Km Nt Gm |
| MutAB B6 pfm | AMC2302; pANS-aadAI-PconII-mutA-mutB; NS2TC::aphI-PconII-epimerase; NS1::nat1-pT7-papA5-fadD28-mas; NS3::aacC1-PconII-rswF-sfp-PconII6-rswB-T7RNAP | Sp Sm Km Nt Gm |
| PCC F pfm | AMC2302; pANS-aadAI-PconII-accA2-pccB-pccE; NS1::nat1-pT7-papA5-fadD28-mas; NS3::aacC1-PconII-rswF-sfp-PconII-rswF-T7RNAP | Sp Sm Nt Gm |
| PCC B6 pfm | AMC2302; pANS-aadAI-PconII-accA2-pccB-pccE; NS1::nat1-pT7-papA5-fadD28-mas; NS3::aacC1-PconII-rswF-sfp-PconII6-rswB-T7RNAP | Sp Sm Nt Gm |

Figure 12B:
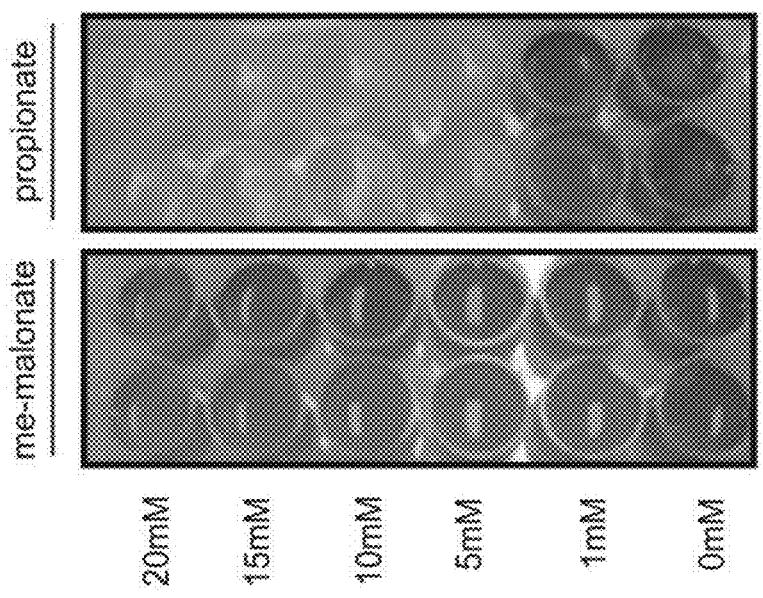
FIGS. 12A-12B show cell toxicity analysis to determine the optimal concentration of precursors.

While module I was constitutively expressed from Peonn (Elledge and Davis et al. 1989; Taton et al. 2014), the expression and activation of module III depended on the expression of the T7 RNAP and Sfp placed in downstream $P_{conII}$ and under the translational control of theophylline inducible riboswitches. The biosynthesis of methylmalonyl-CoA required methylmalonate (module IA) or propionate (module IC) as substrates, and the transesterification of the ACP-bound MBFA required an alcohol substrate (n-octanol) to produce MBE as the final product. Cell toxicity analysis with methylmalonate, propionate and n-octanol were carried out to determine the optimal concentration of these precursors. (FIG. 12).

The two strains containing module IA (MatB) for methylmalonyl-CoA biosynthesis, modules IIA or IIB for T7 RNAP and Sfp expression, and module III for the Mas and accessory enzyme expression were analyzed. In addition, strains without the module III and a wild type strain were comprised as negative controls. For the bioconversion assays the strains were induced with theophylline 2 mM and 24 h later supplemented with 10 mM methylmalonate, 0.25 mM n-octanol and labeled with 2 µCi $^{14}$C-acetate (58.9 mCi/mmol, PerkinElmer). After addition of the precursors the cultures were grown for 48 h, the in vivo synthesis of MBE was analyzed on total lipid extractions from each culture by TLC fractionation and autoradiography (FIGS. 3A-3B). Additional control bioconversion assays were carried out in the absence of either or both precursors, and labeled MBE synthesized by the E. coli strain RQ1 used as a standard (Menendez-Bravo et al. 2014).

Figure 3:
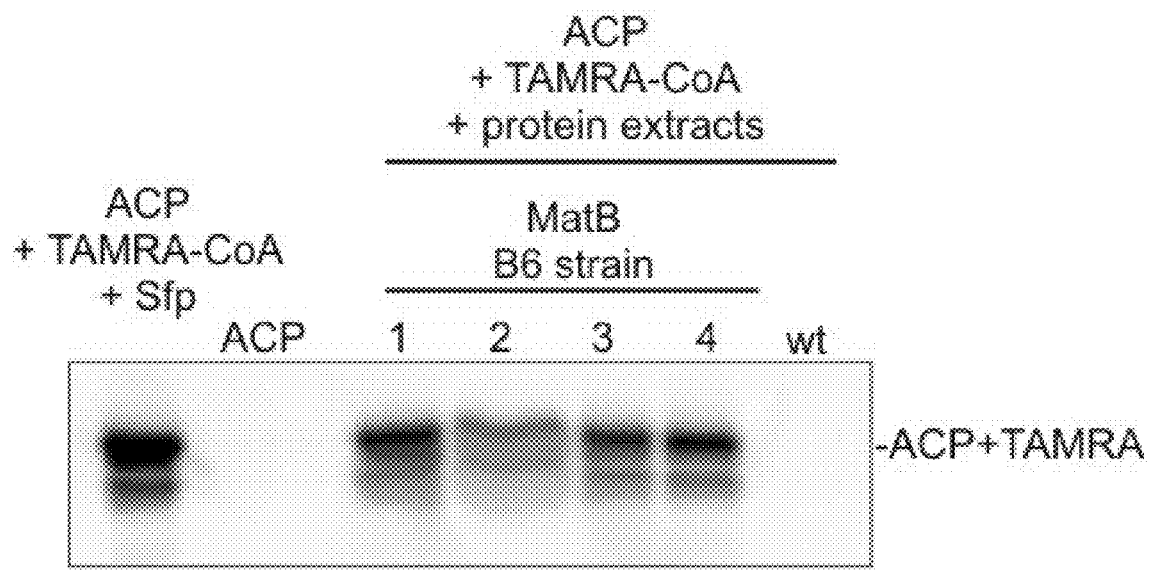
FIG. 3 shows PPTase in vitro assays. Sfp functional assay through fluorescent ACP labeling. Proteins were separated by SDS-PAGE and visualized by UV fluorescence. Lanes: 1, purified *E. coli* ACP plus TAMRA-CoA and purified Sfp (positive control); 2, purified *E. coli* ACP; 3, 4, 5, purified *E. coli* ACP plus TAMRA-CoA and total protein extracts from three biological replicates of MatB B6 pfm recombinant strains, respectively; 6, purified *E. coli* ACP plus TAMRA-CoA and protein extracts from MatB B6 recombinant strain; 7, purified *E. coli* ACP plus TAMRA-CoA and wild type strain protein extract (negative control).
Figure 13:
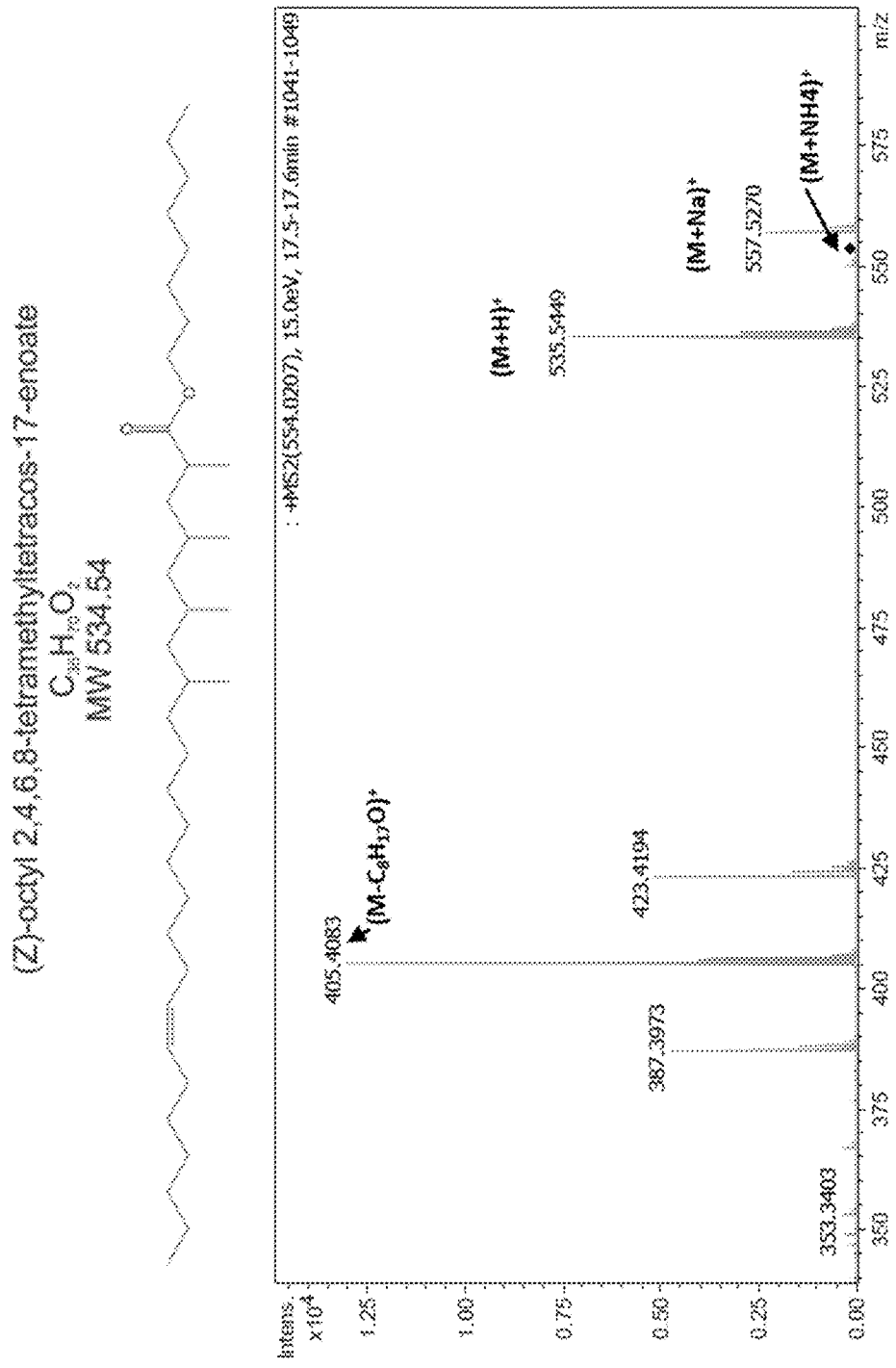
FIG. 13 shows LC-MS/MS MBE analysis. Analysis by LC-MS of total lipid extracts obtained from induced cultures of *S. elongatus* AMC2302 recombinant strains supplemented with n-octanol and methylmalonate. Mass spectra are in agreement with the chemical formula $C_{36}H_{70}O_2$, which corresponds to the MBE formed by condensation of n-octanol and the MBFA derived from four iterative MAS-catalyzed extension steps of palmitoleic acid (one of the most abundant fatty acid found in *S. elongatus*).

The results shown in FIG. 3 indicate that S. elongatus was successfully engineered to synthesize MBE. The production of MBE was detected when both precursors and the enzymes of the PKS pathway (module III) were present. To confirm the nature of the putative MBE compounds, analytical characterization of purified MBE was carried out by LC-MS/MS experiments as illustrated in FIG. 13. From this analysis, MBE synthesized by S. elongatus recombinant strains were at least formed by the condensation of the MBFA (methyl-branched fatty acid) derived from four iterative MAS-catalyzed extension steps of a C16:1 fatty acid as starter unit and the n-octanol as acceptor alcohol. Altogether, these results indicated that methylmalonyl-CoA was synthesized through MatB-epimerase pathway (module IA), using methylmalonate as precursor. These assays further confirmed that module II (A and B) produced functional T7 RNAP and PPTase, which enabled the expression and activation of module III enzymes. Finally, these results indicated that the basic mycoserosic acid (MA) biosynthesis system (FadD28-Mas-PapA5) previously reconstituted in E. coli and cloned as module III was properly expressed and functional in S. elongatus.

Figure 12A:
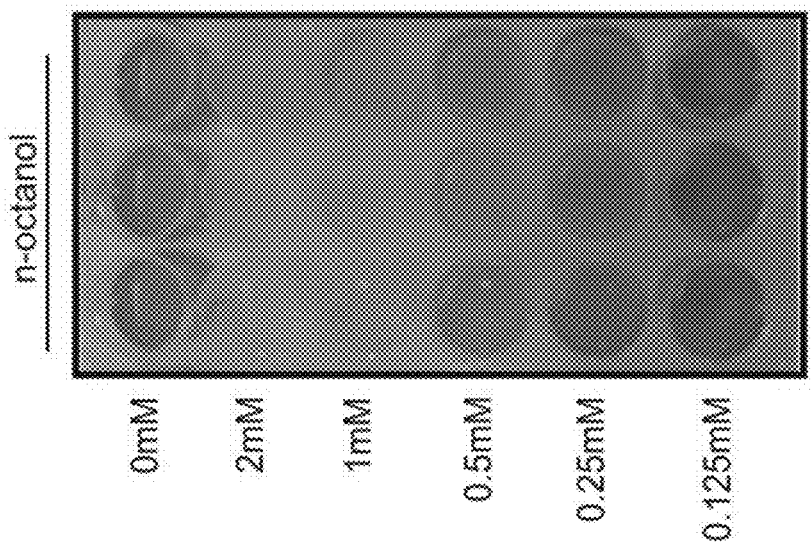

Next, module IC was tested for the biosynthesis of (2S)-methylmalonyl-CoA from propionate by the PCC pathway. This biosynthetic route was considered more challenging because it implied the expression of a complex of three enzymes (AccA2, PccB and PccE), it required an exogenous supply of propionate, which was previously reported as toxic for S. elongatus at low concentrations (Matthew B. Begemann et al. 2013) and propionate had to be converted into propionyl-CoA, which as mentioned earlier inventors hypothesized could be performed by a S. elongatus native acetyl-CoA synthetase/acetate-CoA ligase (AcsA, Syn-PCC7942_1352). Preliminary analyses indicated that at a final concentration of 1 mM, propionate was not toxic for S. elongatus (FIG. 12A). The bioconversion assays and MBE production analyses with PCC F pfm and PCC B6 pfm strains (as well as a wild type strain as negative control) were performed as described above but the cultures were adjusted to final concentrations of 1 mM propionate, 0.25 mM n-octanol, and the cells were labeled with 2 µCi $^{14}$C-acetate (58.9 mCi/mmol, PerkinElmer). The results shown in FIG. 4 indicated that module IC for methylmalonyl-CoA biosynthesis in cyanobacteria was functional and enabled MBE production.

Figure 4A:
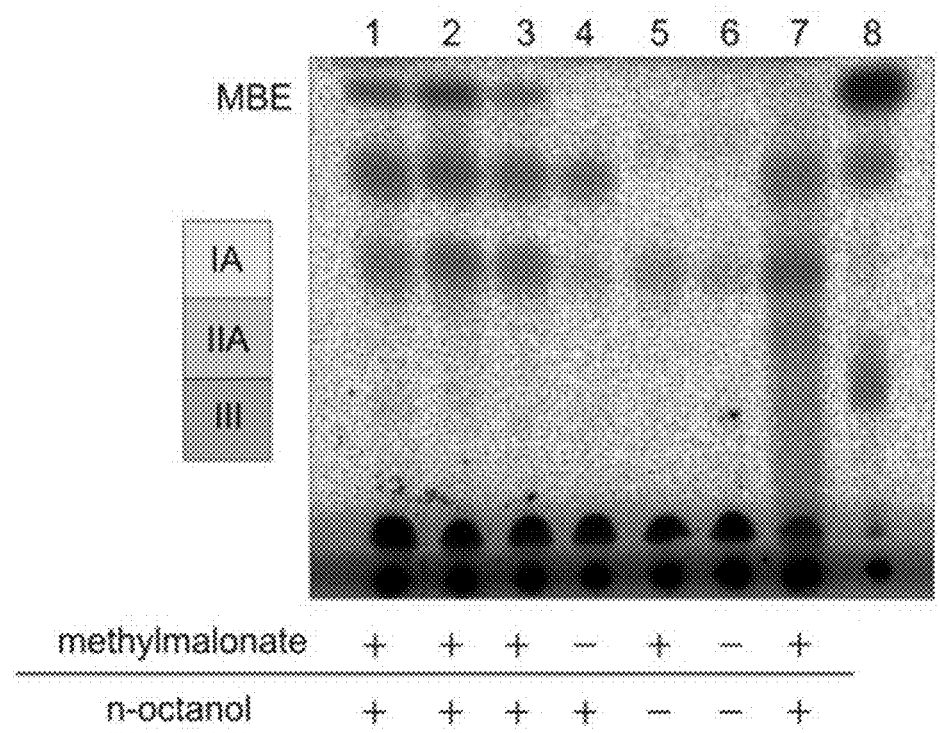
FIGS. 4A-4B show MBE biosynthesis by recombinant MatB F pfm and MatB B6 pfm cyanobacterial strains.
Figure 4B:
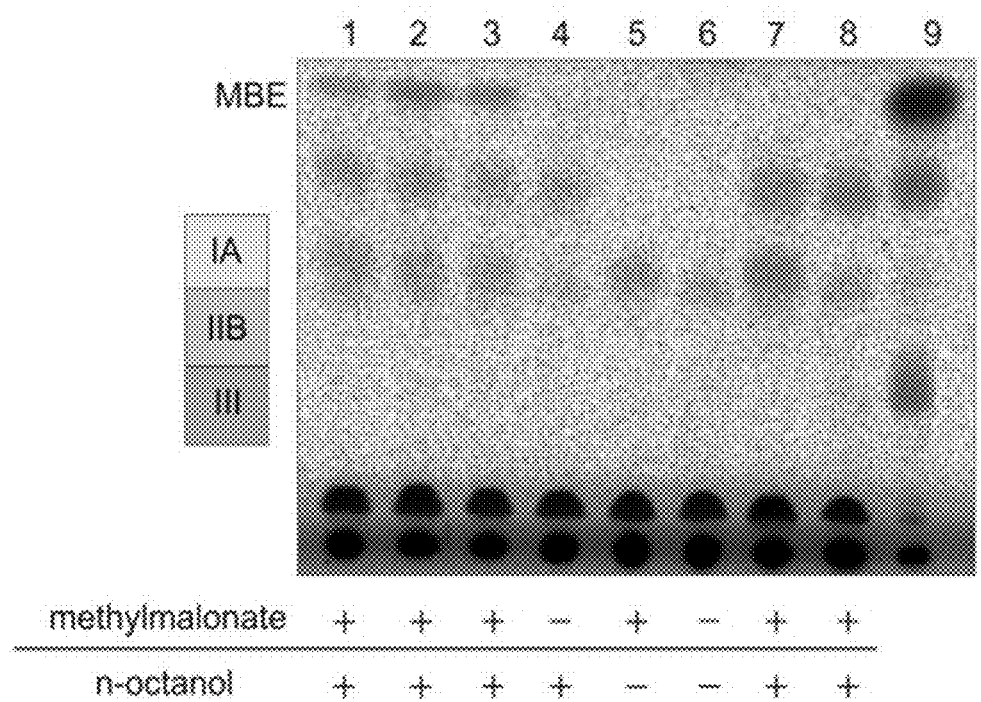
Figure 5:
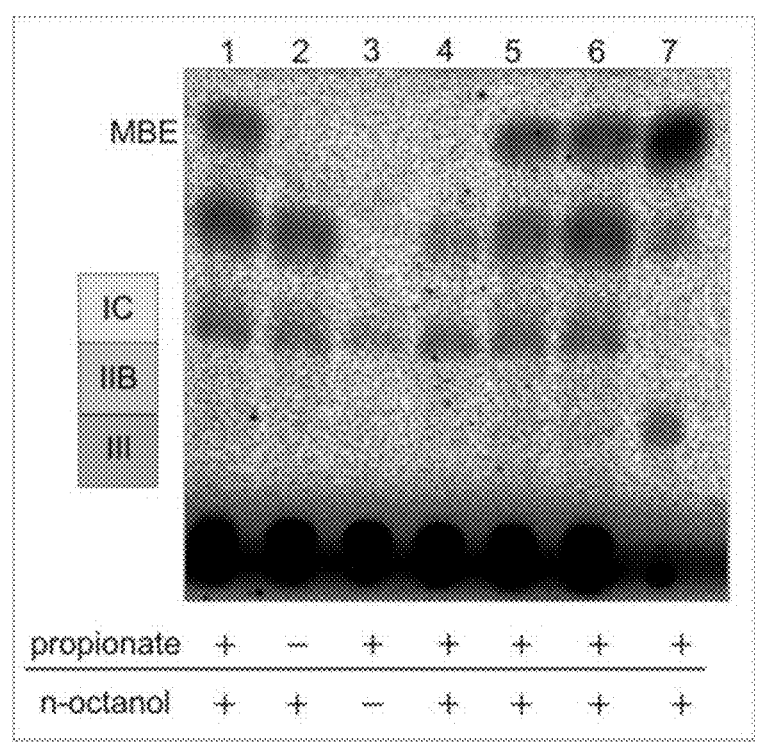
FIG. 5 shows MBE biosynthesis by recombinant PCC B6 pfm cyanobacterial strains. Radio-TLC analysis of total lipid fraction from *S. elongatus* recombinant strain PCC B6 pfm (lanes 1, 2, 3, 5, 6) strains, *S. elongatus* WT (lane 4) and *E. coli* RQ1 MBE producer used as a MBE standard (lane 7) after a bioconversion assay. The lipid fractions on lanes: 1, 5, and 6, were extracted from 3 cultures grown from 3 independent clones as biological replicates. The cultures used for lanes 1, 2 and 3 were grown from the same clone as for lane 1 but with different supply of n-octanol and propionate as indicated below each lane.
Figure 6A:
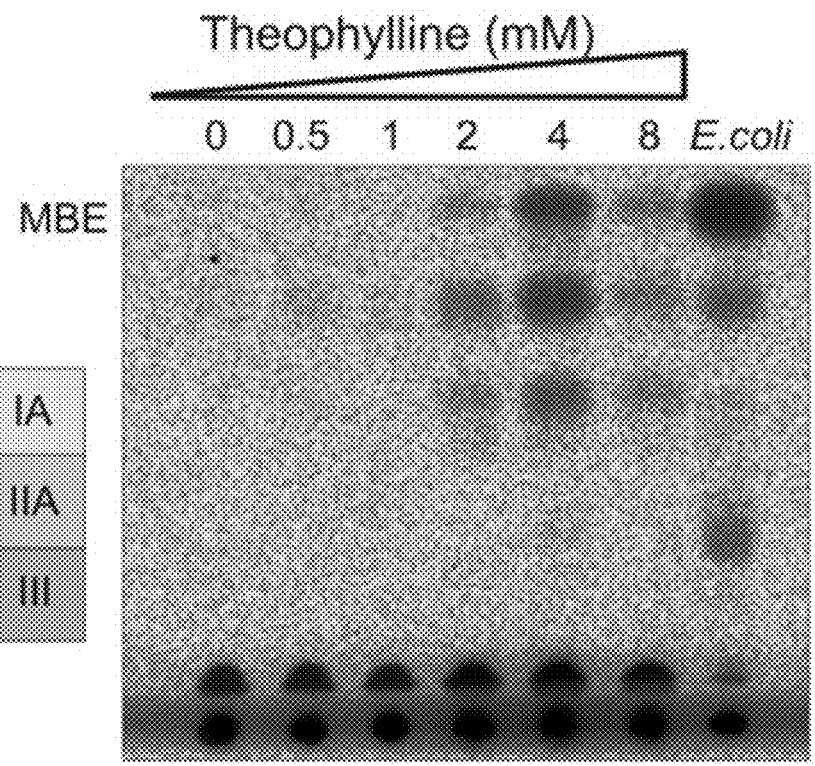
FIGS. 6A-6B show MBE biosynthesis by recombinant MatB F pfm and MatB B6 pfm cyanobacterial strains induced with different theophylline concentrations.
Figure 6B:
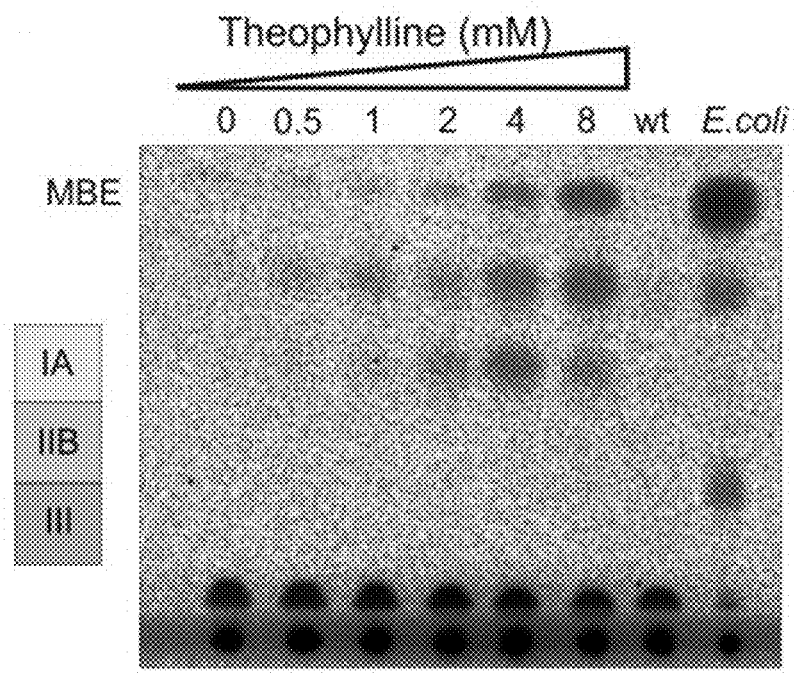

Overall, the analysis of TLCs shown in FIGS. 4A, 4B and 5 and LC-MS/MS experiments shown in FIG. 13 clearly demonstrate that strains MatB F pfm (modules IA+IIA+III), MatB B6 pfm (modules IA+IIB+III), PCC F pfm (modules IC+IIA+III), and PCC B6 pfm (modules IC+IB+III) succeeded to produce methylmalonyl-CoA PKS-derived MBE. These results demonstrated that methylmalonyl-CoA was synthesized in vivo through two different pathways and were available as a substrate for the multidomain Mas PKS enzyme.

Relationship Between Inducer Concentration and MBE Production.

In order to test the functionality of the two different T7 RNA polymerase based expression systems built as modules II A and B, and their impact on the production of MBE, bioconversion assays were conducted with strains MatB B6 pfm and MatB F pfm in the presence of different concentrations of theophylline (0, 0.5, 1, 2, 4 and 8 mM). The bioconversion assays and MBE production analyses show that both riboswitches respond to different concentrations of the inducer. However, module IIB had a better inducer-dependent control, since the levels of MBE produced appeared to be strictly dependent on the concentration of theophyllin. On the other hand, module IIA was less sensitive to lower doses of the inducer, however it reached high levels of MBE production with only 4 mM of theophylline, while higher concentrations (8 mM) become detrimental to cell viability.

Summary

Figure 14:
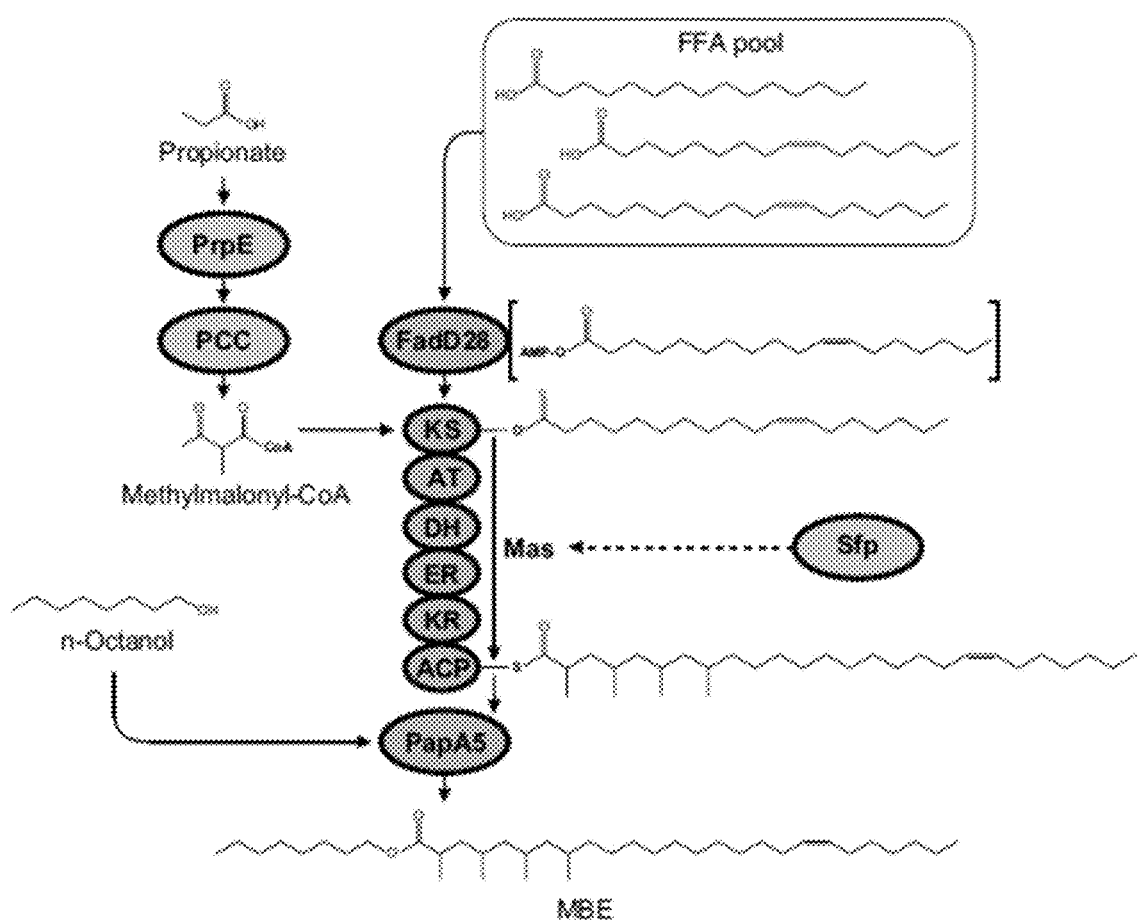
FIG. 14 is a schematic showing production of methyl-branched wax esters (MBE) using the biosynthetic pathway based on the mycocerosic acid synthase (MAS) PKS system.

This is the first time that a functional heterologous PKS system has been expressed in a photosynthetic microorganism. The biosynthetic pathway is illustrated in FIG. 14. Further, it is relevant that S. elongatus does produce its own PKS products, thus serving as a biosynthetically naïve host. Consequently, proof that this cyanobacterium is capable of expressing such complex enzymes systems, and considering the advantages of S. elongatus, comprising the ability to photosynthesize, short life cycle, and superior genetic manipulation capabilities makes it an excellent clean host for polyketide production. The methodologies developed here for production of precursors and expression of accessory proteins will serve as a platform for production of a wide variety of polyketide products. These comprises small molecules useful as medicinal natural products, biofuels, and polymer precursors. The development of a photosynthetic PKS producing host will prove valuable for low cost, high volume production of valuable small molecules, and inventors are currently evaluating culture scale-up on the +100 L level as proof of concept.

In summary, the modular-functional design of the strains here developed offers the unprecedented possibility of producing polyketide-molecules of industrial interest from a photosynthetic platform. On the basis of this platform, other methylmalonyl-CoA derived polyketides could be produced in a sustainable and profitable manner by changing the third module with the desired PKS. Further, other PKS classes that require malonyl-CoA, ethylmalonyl-CoA, and other CoA precursors should be accessible by this approach.

Materials and Methods
Plasmids Construction

The pJR01 vector was constructed from CYANO-VECTOR compatible devices isolated by restriction digests from pCVD002 (AADA), pCVD026 (ORIBOM), pCVD048 (PANS), and pCVD078 (PCONII-RBS-CAT-CCDB) following the instructions provided by the CYANO-VECTOR portal5. The pJR02 vector was constructed similarly from pCVD003 (APHI), pCVD023 (NS2TC), and pCVD078 (PCONII-RBS-CAT-CCDB). The pAM5204 vector was constructed similarly from pCVD001 (AACC1), pCVD023 (NS2TC), and pCVD074 (CCDB-RIBOJ-ORBS-YFP).

To construct plasmids pJR03 and pJR06, the pJR01 vector was digested with EcoRI/SbfI restriction enzymes to release the cat-ccdB cassette. Subsequently, assembly reactions were performed with the linearized pJR01 backbone and the codon optimized 8 matB synthetic gene for pJR03, or the aacA2-pccE-pccB DNA fragment obtained by PCR from pCC05 for pJR06.

To construct plasmid pJR04, the pJR02 vector was digested with EcoRI/SbfI to release the cat-ccdB cassette. Subsequently, an assembly reaction was performed with the linearized pJR02 backbone and the synthetic gene sequence coding for the P. shermanii epimerase.

To construct plasmid pJR05, the pJR01 vector was digested with EcoRI/SbfI to release the cat-ccdB cassette. Subsequently, the linearized pJR01 backbone was used to perform an assembly reaction with the mutA synthetic gene, which had been released from the pUC57 vector backbone by AarI. Then, the resulting vector was linearized with ScaI and the assembly reaction was performed with the mutB synthetic gene, which had been released from the pUC57 vector backbone by the AarI.

To construct plasmid pJR07, the pMB07 plasmid was digested with MluI/PsiI to release a DNA fragment corresponding to the PT7-papA5-fadD28-mas operon, which was assembled with a plasmid backbone containing the homologous recombination sequences for chromosomal integration into S. elongatus neutral site 1 (NS1), an E. coli origin of replication and a bom site (RK2BOM), and a nourseothricin resistance (NtR) gene (nat1_S7942). The plasmid backbone was PCR amplified using the pCV0064 vector as template with the pCV0064_F and pCV0064_R primers. These primers comprise adaptor sequences that overlapped with the PT7-papA5-fadD28-mas DNA fragment.

To construct plasmids pAM5468 and pAM5469, the pAM5050 and pAM5051 vectors 1020 were linearized with EcoRI. Subsequently, DNA fragments harboring the T7RNAP coding sequence were PCR-amplified from plasmid pAR1173 with the rswB_T7-pol-F and T7-RNApol_D2670R primers or the rswF_T7-pol-F and T7-RNApo_D2670R primers and then assembled with the linearized pAM5050 or pAM5051 vectors, respectively.

Plasmid pAM5470 and pAM5471 were obtained by QuikChange site-directed mutagenesis (Agilent) with CONII-11A1F and CONII-11A1R primers of plasmid. pAM5468 and pAM5469, respectively. The QuikChange PCRs followed the manufacturer's instructions. To construct plasmids pJR08 and pJR09, the pCV0053 vector was linearized and the ccdB gene released using SwaI. Subsequently the pCV0053 backbone was assembled with a device coding for the Sfp ($P_{conII}$-rswF-sfp) and either one of 2 devices coding for the T7RNAP ($P_{conII}$-rswF-T7RNAP and $P_{conII}$*-rswB-T7RNAP). The Sfp device was PCR-amplified with the sfp_F and sfp_R primers using plasmid pCV0095 as template. The $P_{conII}$-rswF-T7RNAP (pJR08) and $P_{conII}$*-rswB-T7RNAP (pJR09) devices were PCR-amplified with the T7RNAP_F and T7RNAP_R primers from plasmids pAM5469 and pAM5468, respectively.

To construct plasmid pAM5467, the pAM5204 vector was digested with AatII and SwaI to release the ccdB toxic gene. Subsequently, the T7 promoter was obtained by annealing the complementary oligonucleotides PT7-F and PT7-R and ligated into the pAM5204 backbone. For the annealing reaction both oligonucleotides were re-suspended in water at a concentration of 100 mM, then equal volumes (2 µl) of each oligonucleotide were mixed with 10× T4 DNA ligase buffer (5 µl) and water (43 µl) to obtain a final volume of 50 µl; final concentrations of each oligo were 4 mM and the T4 DNA ligase buffer was 1×. The reaction was then placed in a thermocycler at 95° C. for 3 min and then ramped down to 25° C. over 45 min.

Protein Extraction and Western Blot Analysis

Recombinant S. elongatus cell pellets were first stored at −80° C. Then thawed, resuspended in PBS (phosphate-buffered saline), and disrupted by vortexing with diameter 0.2-0.3 mm glass beads (Sigma), for 10 min at 30 s intervals at 2° C. After centrifugation, the supernatants were removed to new tubes. Protein concentration was determined by the BCA method using bovine serum albumin (BSA) as a standard. Soluble protein extracts were subjected to SDS-PAGE and transferred to nitrocellulose membranes. Immunoblots were separately incubated in the presence of the corresponding antibody: monoclonal anti-FLAG antibody (Sigma Aldrich), 6×-His Tag monoclonal antibody (Thermo Fisher) as described in their commercial protocols, or anti-PccB antibody as previously described 2. Each membrane was then incubated with the corresponding secondary antibody labeled with HRP. Protein expression was finally detected with enhanced chemiluminescence (Thermo Fisher).

Cell Toxicity Analysis

First, S. elongatus wild-type cells were pre-grown in order to have an exponential phase culture, then this culture was adjusted to an optical density at 750 nm (OD750) of 0.1 in 24-well plates and the precursor compounds were adjusted to their final concentrations. Methylmalonate (me-malonate) and propionate were adjusted to final concentrations of 0, 1, 5, 10, 15, and 20 mM. n-octanol was adjusted to final concentrations of 0.125, 0.25, 0.5, 1, 2, and 0 mM. After the addition of the precursors, the 24-well plates were incubated at 30° C. with continuous illumination of 150-mol photons m−2 s−1 for three days. The experiment was performed in duplicate or triplicate.

LC-MS/MS Analysis

Figure 15:
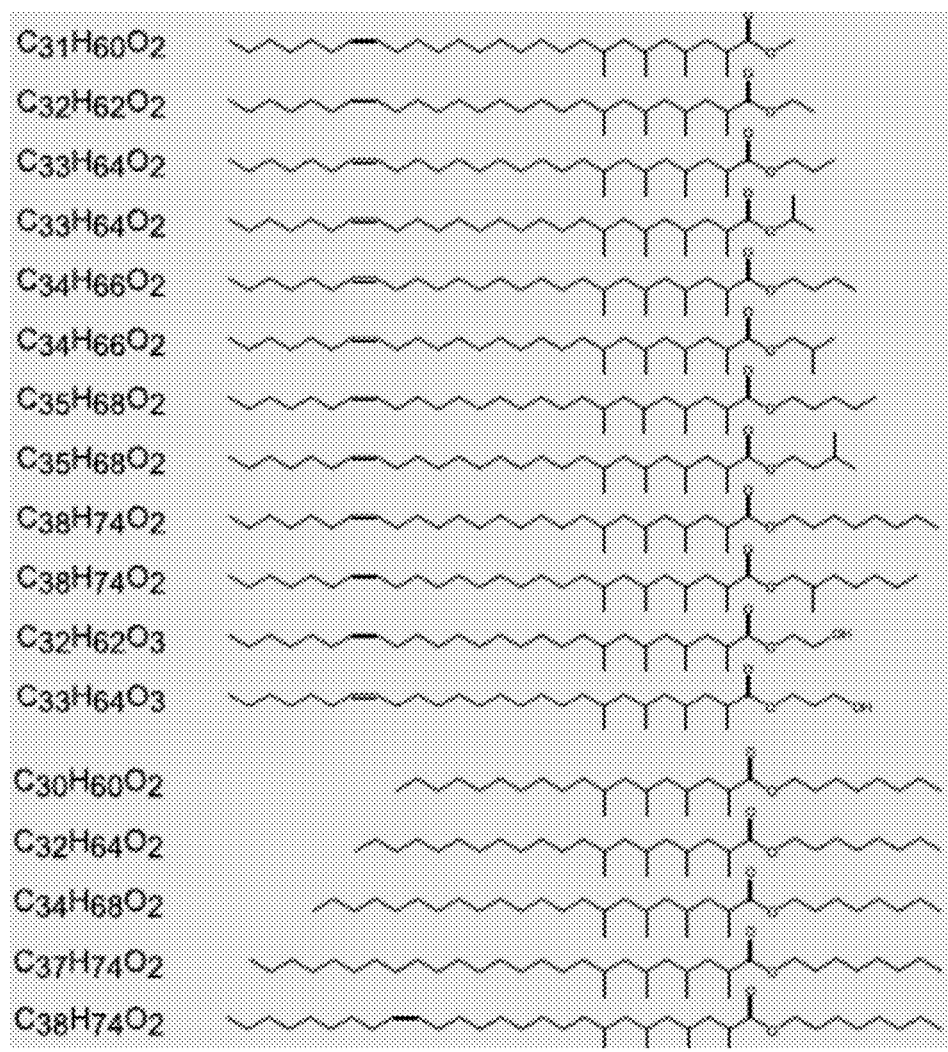
FIG. 15 shows chemical formulas and structures of representative MBE produced by the MAS PKS system.

Total lipid extracts from scraped TLC spots were dried under nitrogen, solubilized in methanol:chloroform (4:1 v/v), and separated on a ZORBAX Eclipse XDB-C8 column (3.0×50 mm, particle size=1.8 m; Agilent, USA) using a binary solvent system of water (Solvent A) and methanol (Solvent B). A linear gradient from 80% B to 100% B was applied between 0 and 25 minutes. Both solvents were supplemented with 5 mM ammonium acetate. The outlet of the liquid chromatography was connected to a micrOTOF mass spectrometer (Bruker Daltonik, Bremen, Germany) operating in the positive-ion mode and the data was acquired online in the mass range m/z 35-1000. MBE products were detected as ammonium, sodium, and proton adducts in the range of 12-18 min of the chromatography run. Chemical structures of the MBE synthesized were confirmed by MS/MS analysis applying collision energy of 15 eV and monitoring 1081 transitions of the corresponding molecular ions. Chemical formulas and structures of various MBE are shown in FIG. 15.

TABLE 3

Source and intermediate plasmids

| Plasmid | Description (plasmid descriptive name) |
|---|---|
| pJR01 | Replicative destination vector for *S. elongatus* with $P_{conII}$, RBS and the cat-ccdB cloning cassette; $Sp^R$, $Sm^R$, and $Cm^R$ (pANS-aadAI-$P_{conII}$-cat-ccdB). |
| pJR02 | Destination vector for chromosomal integration into *S. elongatus* NS2 with $P_{conII}$, RBS, and the cat-ccdB cloning cassette; $Km^R$ and $Tc^R$ (NS2TC-aphI-$P_{conII}$-cat-ccdB). |
| pMB07 | pET28 derivative plasmid containing papA5, fadD28, and mas; $Km^R$. |
| pCC05 | pET28a derivative plasmid containing accA2, pccE, and pccB genes; $Km^R$. |
| pCVD001 | Donor plasmid with a gentamycin resistance ($Gm^R$) device (aacC1); $Ap^R$, $Gm^R$. |
| pCVD002 | Donor plasmid with a spectinomycin and streptomycin resistance ($Sp^R + Sm^R$) device (aadA); $Ap^R$, $Sp^R$, and $Sm^R$. |
| pCVD003 | Donor plasmid with a kanamycin resistance ($Km^R$) device (aph1); $Ap^R$, $Km^R$. |
| pCVD010 | Donor plasmid with a nourseothricin resistance ($Nt^R$) device (nat_7942); $Ap^R$, $Nt^R$. |
| pCVD023 | Donor plasmid with a chromosomal integration device (S7942NS2TC) for *S. elongatus* NS2 that also comprises the pBR322 origin of replication and bom site, and a tetracycline resistance ($Tc^R$) gene; $Ap^R$, $Tc^R$. |
| pCVD026 | Donor plasmid with the pBR322 origin of replication and bom site (oribom); $Ap^R$. |
| pCVD048 | Donor plasmid with a replication device for *S. elongatus* (pANS), which comprises a part of *S. elongatus* small pANS plasmid; $Ap^R$. |
| pCVD044 | Donor plasmid with a device where the conII promoter drives the expression of yfp; $Ap^R$. |
| pCVD074 | Donor plasmid with a reporter device (ccdB-RiboJ-yfp) where the yfp is downstream of a ccdB cloning cassette, an insulator sequence derived from RiboJ and an RBS; $Ap^R$. |
| pCVD078 | pCVD044 where the yfp has been replaced with the ccdB toxic gene and a chloramphenicol resistance ($Cm^R$) gene to facilitate downstream cloning applications; $Ap^R$, $Cm^R$. |
| pCV0053 | Destination plasmid for chromosomal integration into *S. elongatus* NS3 with the ccdB cloning cassette; $Gm^R$ (S7942NS3-RK2BOM_aacC1_ccdB/SwaI). |
| pCV0064 | Destination vector for chromosomal integration into *S. elongatus* NS1 with the ccdB cloning cassette; $Nt^R$ (S7942NS1-RK2BOM_nat1_S7942_ccdB/SwaI). |
| pAM5050 | Destination vector for chromosomal integration into *S. elongatus* NS1 with $P_{conII}$, riboswitch B, and EcoRI restriction site for cloning; $Sp^R$, $Sm^R$ (NS1-aadA-$P_{conII}$-rswB). |
| pAM5051 | Destination vector for chromosomal integration into *S. elongatus* NS1 with $P_{conII}$, riboswitch F, and EcoRI restriction site for cloning; $Sp^R$, $Sm^R$ (NS1-aadA-$P_{conII}$-rswF). |
| pAR1173 | pBR322 plasmid carrying the T7RNAP gene |
| pAM5468 | pAM5050 with T7RNAP insert |
| pAM15469 | pAM5051 with T7RNAP insert |
| pAM5470 | pAM5050_rswB-T7RNAP with the-10 sequence of $P_{conII}$ changed to GCGTATTGT (from TCGTATAAT) |
| pAM5471 | pAM5051_rswF-T7RNAP with the-10 sequence of $P_{conII}$ changed to GCGTATTGT (from TCGTATAAT) |
| pAM5204 | Destination vector for chromosomal integration into *S. elongatus* NS2 with the ccdB-RiboJ-yfp reporter device; $Tc^R$, $Gm^R$ (NS2TC-aacC1-ccdB-riboJ-yfp). |
| pAM5467 | pAM5204 where ccdB and the insulator sequence (RiboJ) have been replaced by $P_{T7}$ to drive the expression of yfp; $Tc^R$, $Gm^R$ (NS2TC-aacC1-$P_{T7}$-yfp). |
| pCV0095 | S7942NS3-CAT7942-$P_{conII}$-rswF-sfp |

TABLE 4

Oligonucleotides: Oligonucleotides used for PCR amplification. Adaptors for Gibson Assembly are in lower case and specific target sequences are in upper case.

| Primer name | Oligonucleotide sequence | SEQ ID NO. |
|---|---|---|
| PCC operon_F | ctatttaaataaaggaggtcttaagatgCGCAAGGTGCTCATCGCC | 1 |
| PCC operon_R | ccatccgtcaggatggccttctcctgcaTTACAGGGGGATGTTGCCG | 2 |
| pCV0064_F | ccctatctcggtctattcttttgatttaAAATGAAGGAGCTCCCCGGCAG | 3 |
| pCV0064_R | agcggcggtgcacaatcttctcgcgcaaAAATCCCTGGGTTATTGGCCGAC | 4 |

TABLE 4-continued

Oligonucleotides: Oligonucleotides used for PCR amplification. Adaptors for Gibson Assembly are in lower case and specific target sequences are in upper case.

| Primer name | Oligonucleotide sequence | SEQ ID NO. |
| --- | --- | --- |
| T7RNAP_F | ggccaataacccagggatttAAGGTTTCGGTCTCCACGCATTC | 5 |
| T7RNAP_R | cggggagtaagttagtcggtGCTTCAAAAAGGCCATCCGTCAG | 6 |
| PT7-F | cTAATACGACTCACTATAGGGAGAattt | 7 |
| PT7-R | aaatTCTCCCTATAGTGAGTCGTATTAgacgt | 8 |
| rswB_T7-pol-F | CAGGGGGTATCAACAAGATGaacacgattaacatcgctaagaacg | 9 |
| rswF_T7-pol-F | GCTAAGGAGGCAACAAGATGaacacgattaacatcgctaagaacg | 10 |
| T7-RNApol_D2 670R | CCGAGGTCGAGACGGcTCATGagtcgtattgatttggcgttacgc | 11 |
| CONII-11A1F | GACAATTAATCATCGGCGCGTATTGTGGTACCGGTGATACC | 12 |
| CONII-11A1R | GGTATCACCGGTACCACAATACGCGCCGATGATTAATTGTC | 13 |
| sfp_F | accgactaacttactccccgGATCAACGTCTCATTTTCGCCAA | 14 |
| sfp_R | tgccggggagctccttcatttAGCTTCAAAAAGGCCATCCGTC | 15 |

TABLE 5

Sequence for promoter, RBS, and accession number for each gene of each module developed for the platform.

| Accession number | Gene | Promoter sequence | SEQ ID NO. | RBS and flanking sequences | SEQ ID NO. |
| --- | --- | --- | --- | --- | --- |
| CAB86109 | matB | PconII: ttgacaattaatcatcggctcgtataatggta | 16 | aaaggaggtcttaag | 24 |
| AY046899 | epimerase | PconII: ttgacaattaatcatcggctcgtataatggta | 17 | aaaggaggtcttaag | 25 |
| X14965 | mutA | PconII: ttgacaattaatcatcggctcgtataatggta | 18 | aaaggaggtcttaag | 26 |
| X14965 | mutB | downstream mutA gene in an operon fashion | X | gaagcggcggtagctaagactaaagg aggtaggaa | 27 |
| Q9EWV4 | accA2 | PconII: ttgacaattaatcatcggctcgtataatggta | 19 | aaaggaggtcttaag | 28 |
| Q9EWV8 | pccE | downstream accA2 gene in an operon fashion | X | ctttaagaaggagatat | 29 |
| Q9X4K7 | pccB | downstream pccE gene in an operon fashion | X | ctttaagaaggagatat | 30 |
| I6YAN2 | papA5 | pT7: taatacgactcactatagg | 20 | ttaactttaagaaggag | 31 |
| I6XFQ7 | fadD28 | downstream papA5 gene in an operon fashion | X | ttaactttaagaaggag | 32 |
| I6Y231 | mas | downstream fadD28 gene in an operon fashion | X | ttaactttaagaaggag | 33 |

TABLE 5-continued

Sequence for promoter, RBS, and accession number for each gene of each module developed for the platform.

| Accession number | Gene | Promoter sequence | SEQ ID NO. | RBS and flanking sequences | SEQ ID NO. |
|---|---|---|---|---|---|
| BG10176 | sfp | PconII: ttgacaattaatcatcggctcgtataatggta | 21 | ggtgataccagcatcgtcttgatgccctt ggcagcaccctgctaaggaggcaaca ag | 34 |
| C1KTT1 | T7RNAP in pJR08 | PconII: ttgacaattaatcatcggctcgtataatggta | 22 | ggtgataccagcatcgtcttgatgccctt ggcagcaccctgctaaggaggcaaca ag | 35 |
| C1KTT1 | T7RNAP in pJR09 | PconII: ttgacaattaatcatcggcgcgtattgtggt | 23 | ggtgataccagcatcgtcttgatgccctt ggcagcacccgctgcgcagggggtat caacaag | 36 |

Codon Optimized and Synthetic Gene Sequences:

*S. coelicolor* MatB: codon optimized sequence using COOL algorithm, GC adaptors for Gibson Assembly are in lower case and the FLAG-tag sequence is underlined. (SEQ ID NO:37)

tatttaaataaaggaggtcttaagATGGACTACAAGGATGACGATGACAA
GTCTAGTTTGTTTCCCGCCCTGTCACCCGCTCCAACTGGCGCACCGGCTG
ATCGCCCAGCCTTGCGCTTTGGTGAACGTAGTTTGACGTACGCTGAATTG
GCTGCGGCCGCAGGCGCCACCGCAGGCCGGATTGGTGGCGCTGGTCGCGT
AGCAGTTTGGGCCACCCCAGCTATGGAAACTGGCGTGGCCGTCGTCGCTG
CCTTGTTGGCAGGTGTGGCCGCCGTTCCCCTGAATCCAAAATCGGGTGAT
AAAGAATTAGCTCATATCTTAAGCGATAGTGCCCCTTCATTGGTTCTAGC
CCCCCCTGATGCCGAATTGCCTCCAGCTTTGGGCGCTTTAGAGCGTGTTG
ATGTGGATGTTCGTGCTCGCGGCGCAGTGCCAGAAGATGGTGCTGATGAT
GGCGATCCCGCTCTCGTTGTGTATACCAGTGGCACCACAGGACCTCCTAA
AGGTGCAGTCATCCCCCGTCGTGCTCTAGCTACCACTCTCGATGCCCTGG
CTGACGCATGGCAATGGACCGGTGAAGATGTTCTGGTGCAAGGTTTGCCG
TTGTTTCATGTGCATGGATTGGTGCTGGGCATTCTGGGCCCCCTGCGGCG
CGGCGGCAGCGTGCGCCACCTCGGCCGATTTAGCACCGAAGGCGCCGCTC
GCGAGCTCAACGACGGCGCCACCATGTTGTTCGGCGTCCCCACCATGTAC
CACCGCATTGCGGAGACCCTGCCGGCCGATCCTGAACTCGCCAAGGCGCT
GGCGGGCGCTCGCCTGCTGGTCAGCGGCAGCGCCGCCCTTCCGGTGCACG
ACCACGAGCGTATAGCTGCCGCGACGGGCCGCCGCGTCATTGAGCGCTAC
GGCATGACCGAAACGCTGATGAACACCTCCGTTCGGGCTGATGGCGAGCC
GCGCGCGGGCACGGTGGGCGTGCCCCTCCCCGGCGTGGAGCTGCGCCTCG
TGGAAGAGGATGGTACGCCGATCGCCGCCCTGGACGGCGAGAGCGTGGGC
GAGATTCAGGTCCGCGGACCCAACCTGTTTACCGAATACCTGAACCGTCC
CGATGCTACGGCCGCCGCTTTTACCGAGGACGGCTTTTTCCGCACGGGCG
ATATGGCTGTGCGCGATCCGGACGGTTACGTGCGGATTGTCGGCCGCAAA
GCGACCGATCTGATCAAATCGGGCGGTTACAAAATTGGCGCCGGTGAAAT -continued CGAAAACGCCCTACTGGAACATCCCGAAGTGCGAGAAGCTGCAGTAACAG
GCGAACCAGACCCCGATCTGGGTGAACGAATCGTGGCTTGGATTGTACCT
GCAGATCCCGCAGCACCGCCCGCCCTGGGAACATTGGCCGATCACGTTGC
TGCACGGCTCGCCCCCCACAAGCGACCGCGGGTTGTCCGCTATCTGGATG
CCGTTCCGCGCAACGACATGGGCAAAATCATGAAGCGCGCCCTGAATCGC
GACTAAAGTACTtgcaggagaaggccatcctgacggatgg

*Propionibacterium shermanii* MutA: The AarI restriction site is double underlined, GC adaptors for Gibson Assembly are in lower case, and the FLAG-tag sequence is underlined. (SEQ ID NO:38)

CACCTGCATGGTACCctatttaaataaaggaggtcttaagATGGACTACA
AGGATGACGATGACAAGAGCAGCACGGATCAGGGGACCAACCCCGCCGAC
ACTGACGACCTCACTCCCACCACACTCAGCCTGGCCGGGGATTTCCCCAA
GGCCACTGAGGAGCAGTGGGAGCGCGAAGTTGAGAAGGTACTCAACCGTG
GTCGTCCACCGGAGAAGCAGTTGACCTTCGCCGAGTGTCTGAAGCGCCTG
ACGGTTCACACCGTCGATGGCATCGACATCGTGCCGATGTACCGTCCGAA
GGACGCCCCGAAGAAGCTGGGTTACCCCGGCGTCGCACCTTTCACCCGCG
GCACCACGGTGCGCAACGGCGACATGGATGCCTGGGACGTGCGCGCCCTG
CACGAGGATCCCGACGAGAAGTTCACCCGCAAGGCGATCCTCGAAGGCCT
GGAGCGTGGCGTCACCTCCCTGTTGCTGCGCGTTGATCCCGACGCGATCG
CACCCGAGCACCTCGACGAGGTCCTCTCCGACGTCCTGCTGGAAATGACC
AAGGTGGAGGTCTTCAGCCGCTACGACCAGGGTGCCGCCGCCGAGGCCCT
GGTGAGCGTCTACGAGCGCTCCGACAAGCCGGCGAAGGACCTGGCCCTCA
ACCTGGGCCTGGATCCCATCGCGTTCGCAGCCCTGCAGGGCACCGAGCCG
GATCTGACCGTGCTCGGTGACTGGGTGCGCCGCCTGGCGAAGTTCTCGCC
GGACTCGCGCGCCGTCACGATCGACGCGAACATCTACCACAACGCCGGTG
CCGGCGACGTGGCAGAGCTCGCCTGGGCACTGGCCACCGGCGCGGAGTAC
GTGCGCGCCCTGGTCGAGCAGGGCTTCACCGCCACCGAGGCCTTCGACAC
GATCAACTTCCGTGTCACCGCCACCCACGACCAGTTCCTCACGATCGCCC

```
GTCTTCGCGCCCTGCGCGAGGCATGGGCCCGCATCGGCGAGGTCTTCGGC

GTGGACGAGGACAAGCGCGGCGCCCGCCAGAATGCGATCACCAGCTGGCG

TGAGCTCACGCGCGAAGACCCCTATGTCAACATCCTTCGCGGTTCGATTG

CCACCTTCTCCGCCTCCGTTGGTGGGGCCGAGTCGATCACGACGCTGCCC

TTCACCCAGGCCCTCGGCCTGCCGGAGGACGACTTCCCGCTGCGCATCGC

GCGCAACACGGGCATCGTGCTCGCCGAAGAGGTGAACATCGGCCGCGTCA

ACGACCCGGCCGGTGGCTCCTACTACGTCGAGTCGCTCACCCGCAGCCTG

GCCGACGCCGCCTGGAAGGAATTCCAGGAGGTCGAGAAGCTCGGTGGCAT

GTCGAAGGCCGTCATGACCGAGCACGTCACCAAGGTGCTCGACGCCTGCA

ATGCCGAGCGCGCCAAGCGCCTGGCCAACCGCAAGCAGCCGATCACCGCG

GTCAGCGAGTTCCCGATGATCGGGGCCCGCAGCATCGAGACCAAGCCGTT

CCCCGCCGCTCCGGCGCGCAAGGGCCTGGCCTGGCATCGCGACTCCGAGG

TGTTCGAGCAGCTGATGGATCGCTCCACCAGCGTCTCCGAGCGCCCCAAG

GTGTTCCTGGCCTGCTTGGGCACCCGTCGCGACTTCGGTGGCCGCGAGGG

CTTCTCGAGCCCGGTGTGGCACATCGCCGGCATCGACACCCCGCAGGTCG

AAGGCGGCACCACCGCCGAGATCGTCGAGGCATTCAAGAAGTCGGGCGCC

CAGGTGGCCGACCTCTGCTCGTCCGCCAAGGTCTACGCGCAGCAGGGACT

TGAGGTCGCCAAGGCACTCAAGGCCGCCGGCGCAAAGGCCCTGTACCTGT

CGGGCGCCTTCAAGGAGTTCGGTGATGACGCCGCCGAGGCCGAGAAGCTG

ATCGACGGACGCCTGTTTATGGGCATGGATGTCGTCGACACCCTGTCCTC

CACCCTTGATATCTTGGGAGTCGCGAAGTGAAGTACTtgcaggagaaggc cacctgacggatggCCTTTTTGCAGGTG
```

*Propionibacterium shermanii* MutB: The AarI restriction site is double underlined; the c-Myc-tag sequence is underlined. The synthetic RBS indicated with italic and bold font was designed and optimized according to its genetic context using an RBS calculator. The intergenic sequence between mutA and mutB is in italics and adaptors for Gibson Assembly are in lower case. (SEQ ID NO:39)

```
CACCTGCTCCACCCTtgatatcttgggagtcgcgaagtgaagtGAAGCGG

CGGTAGCTAAGACTAAAGGAGGTAGGAAATGGAACAAAAATTGATCTCGG

AAGAAGATTTGAGCACTCTGCCCCGTTTTGATTCAGTTGACCTCGGCAAT

GCCCCGGTTCCTGCTGATGCCGCACGACGCTTCGAGGAACTGGCCGCCAA

GGCCGGCACCGGAGAGGCGTGGGAGACGGCCGAGCAGATTCCGGTTGGCA

CCCTGTTCAACGAAGACGTCTACAAGGACATGGACTGGCTGGACACCTAC

GCAGGTATCCCGCCGTTCGTCCACGGCCCGTATGCAACCATGTACGCGTT

CCGTCCCTGGACGATTCGCCAGTACGCCGGTTTCTCCACGGCCAAGGAGT

CGAACGCCTTCTACCGCCGCAACCTTGCGGCCGGCCAGAAGGGCCTGTCG

GTTGCCTTCGACCTGCCCACCCACCGTGGCTACGACTCGGACAATCCCCG

CGTCGCCGGTGACGTCGGCATGGCCGGTGTGGCCATCGACTCCATCTATG

ACATGCGCGAGCTGTTCGCCGGCATTCCGCTGGACCAGATGAGCGTGTCC

ATGACCATGAACGGCGCCGTGCTGCCGATCCTGGCCCTCTATGTGGTGAC
```

```
CGCCGAGGAGCAGGGCGTCAAGCCCGAGCAGCTCGCCGGGACGATCCAGA

ACGACATCCTCAAGGAGTTCATGGTTCGTAACACCTACATCTACCCGCCG

CAGCCGAGTATGCGAATCATCTCTGAGATCTTCGCCTACACGAGTGCCAA

TATGCCGAAGTGGAATTCGATTTCCATTTCCGGCTACCACATGCAGGAAG

CCGGCGCCACGGCCGACATCGAGATGGCCTATACCCTGGCCGACGGTGTT

GACTACATCCGCGCCGGCGAGTCGGTGGGCCTCAATGTCGACCAGTTCGC

GCCGCGTCTGTCCTTCTTCTGGGGCATCGGCATGAACTTCTTCATGGAGG

TTGCCAAGCTGCGTGCCGCGCGCATGTTGTGGGCAAGCTGGTGCATCAG

TTCGGGCCGAAGAACCCGAAGTCGATGAGCCTGCGCACCCACTCGCAGAC

CTCCGGTTGGTCGCTGACCGCCCAGGACGTCTACAACAACGTCGTGCGTA

CCTGCATCGAGGCCATGGCCGCCACCCAGGGCCATACCCAGTCGCTGCAC

ACGAACTCGCTCGACGAGGCCATCGCCCTGCCGACCGATTTCAGCGCCCG

CATCGCCCGTAACACCCAGCTGTTCCTGCAGCAGGAATCGGGCACGACGC

GCGTGATCGACCCGTGGAGCGGCTCGGCATACGTCGAGGAGCTCACCTGG

GACCTGGCCCGCAAGGCATGGGTCACATCCAGGAGGTCGAGAAGGTCGG

CGGCATGGCCAAGGCCATCGAAAAGGGCATCCCCAAGATGCGCATCGAGG

AAGCCGCCGCCCGCACCCAGGCACGCATCGACTCCGGCCGCCAGCCGCTG

ATCGGCGTGAACAAGTACCGCCTGGAGCACGAGCCGCCGCTCGATGTGCT

CAAGGTGGACAACTCCACGGTGCTCGCCGAGCAGAAGGCCAAGCTGGTCA

AGCTGCGCGCCGAGCGCGATCCCGAGAAGGTCAAGGCCGCCCTCGACAAG

ATCACCTGGGCCGCCGGCAACCCCGACGACAAGGATCCGGATCGCAACCT

GCTGAAGCTGTGCATCGACGCTGGCCGCGCCATGGCGACGGTCGGCGAGA

TGAGCGACGCGCTCGAGAAGGTCTTCGGACGCTACACCGCCCAGATTCGC

ACCATCTCCGGTGTGTACTCGAAGGAAGTGAAGAACACGCCTGAGGTTGA

GGAAGCACGCGAGCTCGTTGAGGAATTCGAGCAGGCCGAGGGCCGTCGTC

CTCGCATCCTGCTGGCCAAGATGGGCCAGGACGGTCACGACCGTGGCCAG

AAGGTCATCGCCACCGCCTATGCCGACCTCGGTTTCGACGTCGACGTGGG

CCCGCTGTTCCAGACCCCGGAGGAGACCGCACGTCAGGCCGTCGAGGCCG

ATGTGCACGTGGTGGGCGTTTCGTCGCTCGCCGGCGGGCATCTGACGCTG

GTTCCGGCCCTGCGCAAGGAGCTGGACAAGCTCGGACGTCCCGACATCCT

CATCACCGTGGGCGGCGTGATCCCTGAGCAGGACTTCGACGAGCTGCGTA

AGGACGGCGCCGTGGAGATCTACACCCCCGGCACCGTCATTCCGGAGTCG

GCGATCTCGCTGGTCAAGAAACTGCGGGCTTCGCTCGATGCCTAGAGTAC

TtgcaggagaaggccatcctgacggatggCCTTTGCAGGTG
```

*Propionibacterium shermanii* epimerase: GC adaptors for Gibson Assembly are in lower case and the FLAG-tag sequence is underlined. (SEQ ID NO:40)

```
CtatttaaataaaggaggtcttaagATGGACTACAAGGATGACGATGACA

AGAGTAATGAGGATCTTTTCATCTGTATCGATCACGTGGCATATGCGTGC

CCCGACGCCGACGAGGCTTCCAAGTACTACCAGGAGACCTTCGGCTGGCA

TGAGCTCCACCGCGAGGAGAACCCGGAGCAGGGAGTCGTCGAGATCATGA
```

-continued

```
TGGCCCCGGCTGCGAAGCTGACCGAGCACATGACCCAGGTTCAGGTCATG

GCCCCGCTCAACGACGAGTCGACCGTTGCCAAGTGGCTTGCCAAGCACAA

TGGTCGCGCCGGACTGCACCACATGGCATGGCGTGTCGATGACATCGACG

CCGTCAGCGCCACCCTGCGCGAGCGCGGCGTGCAGCTGCTGTATGACGAG

CCCAAGCTCGGCACCGGCGGCAACCGCATCAACTTCATGCATCCCAAGTC

GGGCAAGGGCGTGCTCATCGAGCTCACCCAGTACCCGAAGAACTGAtgca ggagaaggccatcctgacggatgg
```

It is understood that the examples and embodiments described herein are for illustrative purposes only and that various modifications or changes in light thereof will be suggested to persons skilled in the art and are to be comprised within the spirit and purview of this application and scope of the appended claims. All publications, patents, and patent applications cited herein are hereby incorporated by reference in their entirety for all purposes.

REFERENCES

Yuzawa S, Keasling J D & Katz L Bio-based production of fuels and industrial chemicals by repurposing antibiotic-producing type I modular polyketide synthases: Opportunities and challenges. J. Antibiot. (Tokyo) 70, 378-385 (2017). [PubMed: 27847387]

Pfeifer B A & Khosla C. Biosynthesis of Polyketides in Heterologous Hosts. Microbiol. Mol. Biol. Rev 65, 106-118 (2001). [PubMed: 11238987]

Xue Q, Ashley G, Hutchinson C R & Santi D V A multiplasmid approach to preparing large libraries of polyketides. Proc. Natl. Acad. Sci. U.S.A 96, 11740-11745 (1999). [PubMed: 10518520]

Gokhale R S, Sankaranarayanan R & Mohanty D Versatility of polyketide synthases in generating metabolic diversity. Curr. Opin. Struct. Biol 17, 736-743 (2007). [PubMed: 17935970]

Dunn B J & Khosla C Engineering the acyltransferase substrate specificity of assembly line polyketide synthases. J. R. Soc. Interface 10, 20130297 (2013). [PubMed: 23720536]

Liu Q, Wu K, Cheng Y, Lu L, Xiao E, Zhang Y, Deng Z & Liu T Engineering an iterative polyketide pathway in Escherichia coli results in singleform alkene and alkane overproduction. Metab. Eng 28, 82-90 (2015). [PubMed: 25536488]

Cai W & Zhang W Engineering modular polyketide synthases for production of biofuels and industrial chemicals. Curr. Opin. Biotechnol 50, 32-38 (2018). [PubMed: 28946011]

Menendez-Bravo S, Comba S, Sabatini M, Arabolaza A& Gramajo H Expanding the chemical diversity of natural esters by engineering a polyketide-derived pathway into Escherichia coli. Metab. Eng 24, 97-106 (2014). [PubMed: 24831705]

Rodriguez E, Menzella H G Gramajo H Chapter 15 Heterologous Production of Polyketides in Bacteria. Methods in Enzymology 459, Elsevier Inc., 2009.

Kealey J T, Liu L, Santi D V, Betlach M C & Barr P J Production of a polyketide natural product in non-polyketide-producing prokaryotic and eukaryotic hosts. Proc. Natl. Acad. Sci. U.S.A. 95, 505-509 1998 [PubMed: 9435221]

Pfeifer B A, Admiraal S J, Gramajo H, Cane D E & Khosla C Biosynthesis of complex polyketides in a metabolically engineered strain of E. Coli. Science 291, 1790-1792 (2001). [PubMed: 11230695]

Menendez-Bravo S, Roulet J, Sabatini M, Comba S, Dunn R, Gramajo H & Arabolaza A High cell density production of multimethyl-branched long-chain esters in Escherichia coli and determination of their physicochemical properties. Biotechnol. Biofuels 9, 215 (2016). [PubMed: 27757170]

Smanski M J, Zhou H, Claesen J, Shen B Fischbach M & Voigt C A Synthetic biology to access and expand nature's chemical diversity. Nat Rev Microbiol 14, 135-149 (2016). [PubMed: 26876034]

Stevens D C, Hari T P A & Boddy C N The role of transcription in heterologous expression of polyketides in bacterial hosts. Nat. Prod. Rep 30, 1391-1411 (2013). [PubMed: 24061690]

Fujii I Heterologous expression systems for polyketide synthases. Nat. Prod. Rep 26, 155-169 (2009). [PubMed: 19177221]

Ducat D C, Way J C & Silver P A Engineering cyanobacteria to generate high-value products. Trends Biotechnol. 29, 95-103 (2011). [PubMed: 21211860]

Rubin B E, Wetmore K M, Price M N, Diamond S, Shultzaberger R K, Lowe L C, Curtin G, Arkin A P, Deutschbauer A & Golden S S The essential gene set of a photosynthetic organism. Proc. Natl. Acad. Sci. U.S.A 112, E6634-E6643 (2015). [PubMed: 26508635]

Diamond S, Jun D, Rubin B E & Golden S S The circadian oscillator in controls metabolite partitioning during diurnal growth. Proc. Natl. Acad. Sci. U.S.A 112, E1916-E1925 (2015). [PubMed: 25825710]

Vijayan V, Jain I H & O'Shea E K A high resolution map of a cyanobacterial transcriptome. Genome Biol. 12, R47 (2011). [PubMed: 21612627]

Broddrick J T, Rubin B E, Welkie D G, Dud N, Mihf N, Diamond S, Lee J J, Golden S S & Palsson B0 Unique attributes of cyanobacterial metabolism revealed by improved genome-scale metabolic modeling and essential gene analysis. Proc. Natl. Acad. Sci. U.S.A 113, E8344-E8353 (2016). [PubMed: 27911809]

Taton A, Unglaub F, Wright N E, Zeng W Y, Paz-Yepes J, Brahamsha B., Palenik B., Peterson T C, Haerizadeh F, Golden S S & Golden J W Broad-host-range vector system for synthetic biology and biotechnology in cyanobacteria. Nucleic Acids Res. 42, e136 (2014). [PubMed: 25074377]

Ma A T, Schmidt C M & Golden J W Regulation of gene expression in diverse cyanobacterial species by using theophylline-responsive riboswitches. Appl. Environ. Microbiol 80, 6704-6713 (2014). [PubMed: 25149516]

Ruffing A M Engineered cyanobacteria: Teaching an old bug new tricks. Bioeng. Bugs 2, 136-149 (2011). [PubMed: 21637004]

Atsumi S, Higashide W & Liao J C Direct photosynthetic recycling of carbon dioxide to isobutyraldehyde. Nat. Biotechnol 27, 1177-1180 (2009). [PubMed: 19915552]

Ducat D C, Avelar-Rivas J A, Way J C & Silvera P A Rerouting carbon flux to enhance photosynthetic productivity. Appl. Environ. Microbiol 78, 2660-2668 (2012). [PubMed: 22307292]

Videau P, Wells K N, Singh A J, Gerwick W H & Philmus B Assessment of Anabaena sp. strain PCC 7120 as a heterologous expression host for cyanobacterial natural products: production of lyngbyatoxin A. ACS Synth. Biol 5, 978-988 (2016). [PubMed: 27176641]

Knoot C J, Ungerer J L, Wangikar P P & Pakrasi H B Cyanobacteria: promising biocatalysts for sustainable chemical production. J. Biol. Chem jbc.R117.815886 (2017).

Golden S S & Sherman L A A hybrid plasmid is a stable cloning vector for the cyanobacterium *Anacystis nidulans* R2. J. Bacteriol 155, 966-972 (1983). [PubMed: 6309751]

Chen Y, Taton A, Go M, London R E, Pieper L M, Golden S S & Golden J W. Self-replicating shuttle vectors based on pANS, a small endogenous plasmid of the unicellular cyanobacterium *Synechococcus elongatus* PCC 7942. Microbiol. (United Kingdom) 162, 2029-2041 (2016).

Clerico E M, Ditty J L & Golden S S Specialized techniques for site-directed mutagenesis in cyanobacteria. Methods Mol. Biol362, 155-171 (2007). [PubMed: 17417008]

Rippka R, Deruelles J, Waterbury J B, Herdman M & Stanier R Y Generic assignments, strain histories and properties of pure cultures of cyanobacteria. Microbiology 111, 1-61 (1979).

Chin J X, Chung B K S & Lee D Y Codon Optimization OnLine (COOL): A web-based multi-objective optimization platform for synthetic gene design. Bioinformatics 30, 2210-2212 (2014). [PubMed: 24728853]

Bligh E G & Dyer W J A rapid method of total lipid extraction and purification. Can. J. Biochem. Physiol37, 911-917 (1959). [PubMed: 13671378]

Beld J, Sonnenschein E C, Vickery C R, Noel J P & Burkart M D The phosphopantetheinyl transferases: catalysis of a post-translational modification crucial for life. Nat. Prod. Rep 31, 61108 (2014). [PubMed: 24292120]

Chan Y A, Podevels A M, Kevany B M & Thomas M G Biosynthesis of polyketide synthase extender units. Nat. Prod. Rep 26, 90-114 (2009). [PubMed: 19374124]

Hughes A J & Keatinge-Clay A Enzymatic extender unit generation for in vitro polyketide synthase reactions: Structural and functional showcasing of *Streptomyces coelicolor* MatB. Chem. Biol 18, 165-176 2011 [PubMed: 21338915]

Dayem L C, Carney J R, Santi D V, Pfeifer B A, Khosla C & Kealey J T Metabolic engineering of a methylmalonyl-CoA mutase—epimerase pathway for complex polyketide biosynthesis in *Escherichia coli*. Biochemistry 41, 5193-5201 (2002). [PubMed: 11955068]

Diacovich L, Peirn S, Kurth D, Rodriguez E, Podesta F, Khosla C & Gramajo H Kinetic and structural analysis of a new group of acyl-CoA carboxylases found in *Streptomyces coelicolor* A3(2). J. Biol. Chem 277, 31228-31236 (2002). [PubMed: 12048195]

Begemann M B Begemann M B, Zess E K, Walters E M, Schmitt E F, Markley A L & Pfleger B F An organic acid based counter selection system for cyanobacteria. PLoS One 8, e76594 (2013). [PubMed: 24098537]

Van der Plas J, Oosterhoff-Teertstra R, Borrias M & Weisbeek P Identification of replication and stability functions in the complete nucleotide sequence of plasmid pUFI24 from the cyanobacterium *Synechococcus* sp. PCC 7942. Mol. Microbiol 6, 653-664 (1992). [PubMed: 1552863]

Elledge S J & Davis R W Position and density effects on repression by stationay and mobile DNA-binding proteins. Genes Dev 3, 185-197 (1989). [PubMed: 2523839]

Li R & Golden S S Enhancer activity of light-responsive regulatory elements in the untranslated leader regions of cyanobacterial psbA genes. Proc. Natl. Acad. Sci. U.S.A 90, 11678-11682 (1993). [PubMed: 8265608]

Wang B, Wang J & Meldrum D R Application of synthetic biology in cyanobacteria and algae. Front. Microbiol 3, 344 (2012). [PubMed: 23049529]

Kim W J, Lee S-M, Um Y, Sim S J & Woo H M Development of SyneBrick vectors as a synthetic biology platform for gene expression in *Synechococcus elongatus* PCC 7942. Front. Plant Sci 8, 293 (2017). [PubMed: 28303150]

Cao Y Q, Li Q, Xia P F, Wei U, Guo N, Li J W & Wang S G AraBAD based toolkit for gene expression and metabolic robustness improvement in *Synechococcus elongatus*. Sci. Rep 7, 18059 (2017). [PubMed: 29273782]

Taton A, Ma A T, Ota M, Golden S S & Golden J W NOT gate genetic circuits to control gene expression in cyanobacteria. ACS Synth. Biol 6, 2175-2182 (2017). [PubMed: 28803467]

Dubendorf J W & Studier F W Controlling basal expression in an inducible T7 expression system by blocking the target T7 promoter with lac repressor. J. Mol. Biol 219, 45-59 (1991). [PubMed: 1902522]

Huang H H, Camsund D, Lindblad P & Heidorn T Design and characterization of molecular tools for a synthetic biology approach towards developing cyanobacterial biotechnology. Nucleic Acids Res 38, 2577-2593 (2010). [PubMed: 20236988]

Quadri L E N, Weinreb P H, Lei M, Nakano M M, Zuber P & Walsh C T Characterization of Sfp, a *Bacillus subtilis* phosphopantetheinyl transferase for peptidyl carder protein domains in peptide synthetases. Biochemistry 37, 1585-1595 (1998). [PubMed: 9484229]

Shih P M, Wu D, Latifi A, Axen S D, Fewer D P, Talla E, Calteau A, Cai F, Tandeau de Marsac N, Rippka R, Herdman M, Sivonen K, Coursin T, Laurent T, Goodwin L, Nolan M, Davenport K W, Han C S, Rubin E M, Eisen J A, Woyke T, Gugger M & Kerfeld C A Improving the coverage of the cyanobacterial phylum using diversity-driven genome sequencing. Proc. Natl. Acad. Sci. U.S.A 110, 1053-1058 (2013). [PubMed: 23277585]

Calteau A, Fewer D P, Latifi A, Coursin T, Laurent T, Jokela J, Kerfeld C A, Sivonen K, Piel J & Gugger M Phylum-wide comparative genomics unravel the diversity of secondary metabolism in Cyanobacteria. BMC Genomics 15, 977 (2014). [PubMed: 25404466]

Yang G, Zhang Y, Lee N K, Cozad M A, Kearney S E, Luesch H & Ding Y Cyanobacterial Sfp-type phosphopantetheinyl transferases functionalize carrier proteins of diverse biosynthetic pathways. Sci. Rep 7, 11888 (2017). [PubMed: 28928426]

Trivedi O A, Arora P, Vats A, Ansari M Z, Tickoo R, Sridharan V, Mohanty D & Gokhale R S Dissecting the mechanism and assembly of a complex virulence mycobacterial lipid. Mol. Cell 17, 631-643 (2005). [PubMed: 15749014]

La Clair J J, Foley T L, Schegg T R, Regan C M & Burkart M D Manipulation of carrier proteins in antibiotic biosynthesis. Chem. Biol 11, 195-201 (2004). [PubMed: 15123281]

Ishikawa F, Haushalter R W & Burkart M D Dehydratase-specific probes for fatty acid and polyketide synthases. J. Am. Chem. Soc 134, 769-772 (2012). [PubMed: 22188524]

Cardinale S & Arkin A P Contextualizing context for synthetic biology—identifying causes of failure of synthetic biological systems. Biotechnol. J 7, 856-866 (2012). [PubMed: 22649052]

Temme K, Hill R, Segall-Shapiro T H, Moser F & Voigt C A Modular control of multiple pathways using engineered orthogonal T7 polymerases. Nucleic Acids Res 40, 8773-8781 (2012). [PubMed: 22743271]

Kehr J C, Picchi D G & Dittmann E Natural product biosyntheses in cyanobacteria: A treasure trove of unique enzymes. Beilstein J. Org. Chem 7, 1622-1635 (2011). [PubMed: 22238540]

Gomes E S, Schuch V & Lemos E G de M Biotechnology of polyketides: New breath of life for the novel antibiotic genetic pathways discovery through metagenomics. Brazilian J. Microbiol 44, 1007-1034 (2013).

Micallef M L, D'Agostino P M, Al-Sinawi B, Neilan B. a. & Moffitt M C Exploring cyanobacterial genomes for natural product biosynthesis pathways. Mar. Genomics 21, 1-12 (2015). [PubMed: 25482899]

Helfrich E J N, Reiter S & Piel J Recent advances in genome-based polyketide discovery. Curr. Opin. Biotechnol 29, 107-115 (2014). [PubMed: 24762576]

Bernard P., Gabant P., Bahassi E. M. & Couturier M. Positive-selection vectors using the F plasmid ccdB killer gene. *Gene* 148, 71-74 (1994).

Diacovich, L., Peirn, S., Kurth, D., Rodriguez, E., Podesti, F., Khosla, C. & Gramajo, H. Kinetic and structural analysis of a new group of Acyl-CoA carboxylases found in *Streptomyces coelicolor* A3(2). *J. Biol. Chem.* 277, 31228-31236 (2002).

Coates, R. C., Podell, S., Korobeynikov, A., Lapidus, A., Pevzner, P., Sherman, D. H., Allen, E. E., Gerwick, L. & Gerwick, W. H. Characterization of cyanobacterial hydrocarbon composition and distribution of biosynthetic pathways. *PLoS One* 9, e85140 (2014).

Menendez-Bravo, S., Comba, S., Sabatini, M., Arabolaza, A. & Gramajo, H.

Expanding the chemical diversity of natural esters by engineering a polyketide-derived pathway into *Escherichia coli. Metab. Eng.* 24, 97-106 (2014).

Taton, A., Unglaub, F., Wright, N. E., Zeng, W. Y., Paz-Yepes, J., Brahamsha, B., Palenik, B., Peterson, T. C, Haerizadeh, F., Golden, S. S. & Golden, J. W. Broad-host-range vector system for synthetic biology and biotechnology in cyanobacteria. *Nucleic Acids Res.* 42, e136 (2014).

Ma, A. T., Schmidt, C. M. & Golden, J. W. Regulation of gene expression in diverse cyanobacterial species by using theophylline-responsive riboswitches. *Appl. Environ. Microbiol.* 80, 6704-6713(2014).

Davanloo, P., Rosenberg, A. H., Dunn, J. J. & Studiert, F. W. Cloning andexpression of the gene for bacteriophage T7 RNA polymerase. *Proc. Natl. Acad. Sci. U.S.A* 81, 2035-2039 (1984).

Chin, J. X., Chung, B. K. S. & Lee, D. Y. Codon Optimization OnLine (COOL): A web-based multi-objective optimization platform for synthetic gene design. Bioinformatics 30, 2210-2212(2014).

Salis, H. M., Mirsky, E. a & Voigt, C. a. Automated design of synthetic ribosome binding sites to precisely control protein expression. *Nat Biotechnol.* 27, 946-950 (2010).

(Ingram et al. 2010), (Khosla et al. 1999), (Menendez-Bravo et al. 2014), (Murli et al. 2003), (Ducat et al. 2011), (Taton et al. 2014), (Atsumi et al. 2009), (Oliver J W et al. 2013), (Yuzawa et al., The Journal of Antibiotics 2016, 1-8), (Kim et al. Natural product reports. 2016; 33(8):933-41), (Mathur & Kolattukudy 1992), (Trivedi et al. 2005), (Onwueme et al. 2004), (Hammond et al. 1995), (March, Advanced Organic Chemistry, 3rd Ed., John Wiley & Sons, New York, 1985), (Hermanson, Bioconjugate Techniques, Academic Press, San Diego, 1996), (Feeney et al., Modification of Proteins; Advances in Chemistry Series, Vol. 198, American Chemical Society, Washington, D.C., 1982), (McCafferty et al., 1990 *Nature* 348:552), (Kostelny et al. 1992 *J Immunol.* 148:1547), (Pack and Pluckthun 1992 *Biochemistry* 31:1579), (Hollinger et al. 1993, *PNAS.* USA 90:6444), (Gruber et al. 1994 *J Immunol.* 152:5368), (Zhu et al. 1997 *Protein Sci.* 6:781), (Hu et al. 1996 *Cancer Res.* 56:3055), (Adams et al. 1993 *Cancer Res.* 53:4026), (McCartney, et al. 1995 *Protein Eng.* 8:301), (An J H & Kim Y S et al. 1998), (Hughes & Keatinge-Clay 2011), (Dayem et al. 2002), (Broddrick et al 2016), (Matthew B. Begemann et al. 2013), (You Chen et al. 2016), (Elledge and Davis et al. 1989), (Clerico et al 2007), (Dubendorff and Studier 1991), (Huang et al 2010), (Ma et al 2014), (Tieu et al in prep.), (Quadri et al. 1998), (Beld et al. 2014), (Yang et al 2017), (La Clair, et al. 2004 *Chem Biol* 11, 195-201), (Ishikawa, et al. Journal of the American Chemical Society. 2011 Dec. 29; 134(2): 769-72).

What is claimed is:

1. A recombinant cyanobacterium comprising:
   (a) an exogenous gene capable of expressing an exogenous Sfp-type phosphopantetheinyl transferase (PPTase);
   (b) one or more plasmids comprising a plurality of genes expressing a plurality of enzymes that work together to produce a carboxyacyl-CoA compound from a carboxyacyl-CoA precursor, wherein the plurality of genes comprise:
      (i) matB and epimerase;
      (ii) mutA, mutB, and epimerase; or
      (iii) accA2, pccB, pccE, and acsA; and
   (c) an exogenous gene capable of expressing an enzyme that catalyzes the formation of RNA from DNA in the 5'→3' direction.

2. The recombinant cyanobacterium of claim 1, wherein the exogenous gene capable of expressing an exogenous Sfp-type PPTase is sfp.

3. The recombinant cyanobacterium of claim 1, further comprising an exogenous gene capable of expressing an enzyme that catalyzes stereochemical inversion around an asymmetric carbon atom.

4. The recombinant cyanobacterium of claim 1, further comprising an exogenous gene capable of expressing a polyketide synthase.

5. The recombinant cyanobacterium of claim 4, wherein the exogenous gene capable of expressing a polyketide synthase is a mas gene.

6. A recombinant cyanobacterium comprising:
   (a) an exogenous gene capable of expressing an exogenous Sfp-type phosphopantetheinyl transferase (PPTase);
   (b) one or more plasmids comprising a plurality of genes expressing a plurality of enzymes that work together to produce a carboxyacyl-CoA compound from a carboxyacyl-CoA precursor, wherein the plurality of genes comprise:
      (i) matB and epimerase; or
      (ii) accA2, pccB, pccE, and acsA.

7. The recombinant cyanobacterium of claim 1, comprising one or more plasmids comprising a plurality of genes expressing a plurality of enzymes that work together to produce an exogenous Sfp-type PPTase that is capable of activating a polyketide synthase gene.

8. The recombinant cyanobacterium of claim 7, wherein the polyketide synthase gene is a mas gene.

9. The recombinant cyanobacterium of claim 7, wherein the plurality of genes comprises sfp and T7 gene 1.

10. The recombinant cyanobacterium of claim 1, comprising one or more plasmids comprising a plurality of genes expressing a plurality of enzymes that work together to produce a polyketide.

11. The recombinant cyanobacterium of claim 10, wherein the plurality of genes expressing a plurality of enzymes that work together to produce a polyketide comprise mas, fadD28, and papA5.

12. A recombinant cyanobacterium comprising:
   (a) an exogenous gene capable of expressing an exogenous Sfp-type phosphopantetheinyl transferase (PPTase); and
   (b) one or more plasmids comprising a plurality of genes expressing a plurality of enzymes that work together to produce a carboxyacyl-CoA compound from a carboxyacyl-CoA precursor, wherein the plurality of genes comprise:

(i) matB and epimerase;
(ii) mutA, mutB, and epimerase; or
(iii) accA2, pccB, pccE, and acsA;
wherein the cyanobacterium is of the genus Synechococcus.

13. The recombinant cyanobacterium of claim 12, wherein the cyanobacterium is *Synechococcus elongatus*.

14. The recombinant cyanobacterium of claim 1, wherein the exogenous gene capable of expressing an enzyme that catalyzes the formation of RNA from DNA in the 5'→3' direction is a T7 gene 1 that expresses T7 RNA polymerase and is translationally controlled by a riboswitch.

15. The recombinant cyanobacterium of claim 9, wherein the T7 gene 1 expresses T7 RNA polymerase and is translationally controlled by a riboswitch.

16. The recombinant cyanobacterium of claim 6, further comprising:
   (1) an exogenous gene capable of expressing an enzyme that catalyzes the formation of RNA from DNA in the 5'→3' direction;
   (2) an exogenous gene capable of expressing an enzyme that catalyzes stereochemical inversion around an asymmetric carbon atom;
   (3) an exogenous gene capable of expressing a polyketide synthase;
   (4) one or more plasmids comprising a plurality of genes expressing a plurality of enzymes that work together to produce an exogenous Sfp-type PPTase that is capable of activating a polyketide synthase gene;
   (5) one or more plasmids comprising a plurality of genes expressing a plurality of enzymes that work together to produce a polyketide; or
   (6) a combination of two or more of the foregoing.

17. The recombinant cyanobacterium of claim 12, further comprising:
   (1) an exogenous gene capable of expressing an enzyme that catalyzes the formation of RNA from DNA in the 5'→3' direction;
   (2) an exogenous gene capable of expressing an enzyme that catalyzes stereochemical inversion around an asymmetric carbon atom;
   (3) an exogenous gene capable of expressing a polyketide synthase;
   (4) one or more plasmids comprising a plurality of genes expressing a plurality of enzymes that work together to produce an exogenous Sfp-type PPTase that is capable of activating a polyketide synthase gene;
   (5) one or more plasmids comprising a plurality of genes expressing a plurality of enzymes that work together to produce a polyketide; or
   (6) a combination of two or more of the foregoing.

18. The recombinant cyanobacterium of claim 1, wherein the cyanobacterium is of the genus Synechococcus.

19. The recombinant cyanobacterium of claim 6, wherein the cyanobacterium is of the genus *Synechococcus*.

* * * * *

SEQUENCE LISTING

```
<160> NUMBER OF SEQ ID NOS: 40

<210> SEQ ID NO 1
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 1
ctatttaaat aaaggaggtc ttaagatgcg caaggtgctc atcgcc                    46

<210> SEQ ID NO 2
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 2
ccatccgtca ggatggcctt ctcctgcatt acaggggat gttgccg                    47
```

<210> SEQ ID NO 3
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 3
ccctatctcg gtctattctt ttgatttaaa atgaaggagc tccccggcag         50

<210> SEQ ID NO 4
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 4
agcggcggtg cacaatcttc tcgcgcaaaa atccctgggt tattggccga c        51

<210> SEQ ID NO 5
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 5
ggccaataac ccagggattt aaggtttcgg tctccacgca ttc              43

<210> SEQ ID NO 6
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 6
cggggagtaa gttagtcggt gcttcaaaaa ggccatccgt cag              43

<210> SEQ ID NO 7
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 7
ctaatacgac tcactatagg gagaattt                               28

<210> SEQ ID NO 8
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 8
aaattctccc tatagtgagt cgtattagac gt                          32

<210> SEQ ID NO 9
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 9 caggggtat caacaagatg aacacgatta acatcgctaa gaacg                45

<210> SEQ ID NO 10
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 10
gctaaggagg caacaagatg aacacgatta acatcgctaa gaacg                45

<210> SEQ ID NO 11
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 11
ccgaggtcga cacggctcat gagtcgtatt gatttggcgt tacgc                45

<210> SEQ ID NO 12
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 12
gacaattaat catcggcgcg tattgtggta ccggtgatac c                    41

<210> SEQ ID NO 13
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 13
ggtatcaccg gtaccacaat acgcgccgat gattaattgt c                    41

<210> SEQ ID NO 14
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 14
accgactaac ttactccccg gatcaacgtc tcattttcgc caa                  43

<210> SEQ ID NO 15
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 15
tgccggggag ctccttcatt tagcttcaaa aaggccatcc gtc                  43

<210> SEQ ID NO 16

-continued

```
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 16
ttgacaatta atcatcggct cgtataatgg ta                                    32

<210> SEQ ID NO 17
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 17
ttgacaatta atcatcggct cgtataatgg ta                                    32

<210> SEQ ID NO 18
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 18
ttgacaatta atcatcggct cgtataatgg ta                                    32

<210> SEQ ID NO 19
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 19
ttgacaatta atcatcggct cgtataatgg ta                                    32

<210> SEQ ID NO 20
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 20
taatacgact cactatagg                                                   19

<210> SEQ ID NO 21
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 21
ttgacaatta atcatcggct cgtataatgg ta                                    32

<210> SEQ ID NO 22
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 22
```
ttgacaatta atcatcggct cgtataatgg ta    32

<210> SEQ ID NO 23
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 23
ttgacaatta atcatcggcg cgtattgtgg t    31

<210> SEQ ID NO 24
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 24
aaaggaggtc ttaag    15

<210> SEQ ID NO 25
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 25
aaaggaggtc ttaag    15

<210> SEQ ID NO 26
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 26
aaaggaggtc ttaag    15

<210> SEQ ID NO 27
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 27
gaagcggcgg tagctaagac taaaggaggt aggaa    35

<210> SEQ ID NO 28
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 28
aaaggaggtc ttaag    15

<210> SEQ ID NO 29
<211> LENGTH: 17
<212> TYPE: DNA

```
<213> ORGANISM: Artificial Sequence
<220> FEATURE:
<223> OTHER INFORMATION: Synthetic polynucleotide

<400> SEQUENCE: 29
ctttaagaag gagatat                                               17

<210> SEQ ID NO 30
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 30
ctttaagaag gagatat                                               17

<210> SEQ ID NO 31
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 31
ttaactttaa gaaggag                                               17

<210> SEQ ID NO 32
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 32
ttaactttaa gaaggag                                               17

<210> SEQ ID NO 33
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 33
ttaactttaa gaaggag                                               17

<210> SEQ ID NO 34
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 34
ggtgatacca gcatcgtctt gatgcccttg gcagcaccct gctaaggagg caacaag    57

<210> SEQ ID NO 35
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 35
ggtgatacca gcatcgtctt gatgcccttg gcagcaccct gctaaggagg caacaag    57
```

<210> SEQ ID NO 36
<211> LENGTH: 62
<212> TYPE: DNA
<213> ORGANISM: Artificial Sequence
<220> FEATURE:
<223> OTHER INFORMATION: Synthetic polynucleotide

<400> SEQUENCE: 36

```
ggtgatacca gcatcgtctt gatgcccttg gcagcacccg ctgcgcaggg ggtatcaaca    60
ag                                                                  62
```

<210> SEQ ID NO 37
<211> LENGTH: 1540
<212> TYPE: DNA
<213> ORGANISM: Artificial Sequence
<220> FEATURE:
<223> OTHER INFORMATION: Synthetic polynucleotide

<400> SEQUENCE: 37

```
tatttaaata aaggaggtct taagatggac tacaaggatg acgatgacaa gtctagtttg      60
tttcccgccc tgtcacccgc tccaactggc gcaccggctg atcgcccagc cttgcgcttt    120
ggtgaacgta gtttgacgta cgctgaattg gctgcggccg caggcgccac cgcaggccgg    180
attggtggcg ctggtcgcgt agcagtttgg gccaccccag ctatggaaac tggcgtggcc    240
gtcgtcgctg ccttgttggc aggtgtggcc gccgttcccc tgaatccaaa atcgggtgat    300
aaagaattag ctcatatctt aagcgatagt gccccttcat tggttctagc cccccctgat    360
gccgaattgc ctccagcttt gggcgcttta gagcgtgttg atgtggatgt tcgtgctcgc    420
ggcgcagtgc cagaagatgg tgctgatgat ggcgatcccg ctctcgttgt gtataccagt    480
ggcaccacag gacctcctaa aggtgcagtc atccccgtc gtgctctagc taccactctc    540
gatgccctgg ctgacgcatg gcaatggacc ggtgaagatg ttctggtgca aggttttgccg    600
ttgtttcatg tgcatggatt ggtgctgggc attctgggcc cctgcggcg cggcggcagc    660
gtgcgccacc tcggccgatt tagcaccgaa ggcgccgctc gcgagctcaa cgacggcgcc    720
accatgttgt tcggcgtccc caccatgtac caccgcattg cggagaccct gccggccgat    780
cctgaactcg ccaaggcgct ggcgggcgct cgcctgctgg tcagcggcag cgccgccctt    840
ccggtgcacg accacgagcg tatagctgcc gcgacgggcc gccgcgtcat tgagcgctac    900
ggcatgaccg aaacgctgat gaacacctcc gttcgggctg atggcgagcc gcgcgcgggc    960
acggtgggcg tgcccctccc cggcgtggag ctgcgcctcg tggaagagga tggtacgccg   1020
atcgccgccc tggacggcga gagcgtgggc gagattcagg tccgcggacc caacctgttt   1080
accgaatacc tgaaccgtcc cgatgctacg gccgccgctt ttaccgagga cggcttttc   1140
cgcacgggcg atatggctgt gcgcgatccg gacggttacg tgcggattgt cggccgcaaa   1200
gcgaccgatc tgatcaaatc gggcggttac aaaattggcg ccggtgaaat cgaaaacgcc   1260
ctactggaac atcccgaagt gcgagaagct gcagtaacag gcgaaccaga ccccgatctg   1320
ggtgaacgaa tcgtggcttg gattgtacct gcagatcccg cagcaccgcc cgccctggga   1380
acattggccg atcacgttgc tgcacggctc gccccccaca agcgaccgcg ggttgtccgc   1440
tatctggatg ccgttccgcg caacgacatg ggcaaaatca tgaagcgcgc cctgaatcgc   1500
gactaaagta cttgcaggag aaggccatcc tgacggatgg                         1540
```

<210> SEQ ID NO 38

<211> LENGTH: 2030
<212> TYPE: DNA
<213> ORGANISM: Artificial Sequence
<220> FEATURE:
<223> OTHER INFORMATION: Synthetic polynucleotide

<400> SEQUENCE: 38

```
cacctgcatg gtaccctatt taaataaagg aggtcttaag atggactaca aggatgacga      60
tgacaagagc agcacggatc aggggaccaa ccccgccgac actgacgacc tcactcccac     120
cacactcagc ctggccgggg atttccccaa ggccactgag gagcagtggg agcgcgaagt     180
tgagaaggta ctcaaccgtg gtcgtccacc ggagaagcag ttgaccttcg ccgagtgtct     240
gaagcgcctg acggttcaca ccgtcgatgg catcgacatc gtgccgatgt accgtccgaa     300
ggacgccccg aagaagctgg gttaccccgg cgtcgcacct ttcacccgcg caccacggt      360
gcgcaacggc gacatggatg cctgggacgt gcgcgccctg cacgaggatc ccgacgagaa     420
gttcacccgc aaggcgatcc tcgaaggcct ggagcgtggc gtcacctccc tgttgctgcg     480
cgttgatccc gacgcgatcg cacccgagca cctcgacgag gtcctctccg acgtcctgct     540
ggaaatgacc aaggtggagg tcttcagccg ctacgaccag ggtgccgccg ccgaggccct     600
ggtgagcgtc tacgagcgct ccgacaagcc ggcgaaggac ctggccctca acctgggcct     660
ggatccatc gcgttcgcag ccctgcaggg caccgagccg gatctgaccg tgctcggtga      720
ctgggtgcgc gcctggcga agttctcgcc ggactcgcgc gccgtcacga tcgacgcgaa      780
catctaccac aacgccggtg ccggcgacgt ggcagagctc gcctgggcac tggccaccgg     840
cgcggagtac gtgcgcgccc tggtcgagca gggcttcacc gccaccgagg ccttcgacac     900
gatcaacttc cgtgtcaccg ccacccacga ccagttcctc acgatcgccc gtcttcgcgc     960
cctgcgcgag gcatgggccc gcatcggcga ggtcttcggc gtggacgagg acaagcgcgg    1020
cgcccgccag aatgcgatca ccagctggcg tgagctcacg cgcgaagacc cctatgtcaa    1080
catccttcgc ggttcgattg ccaccttctc cgcctccgtt ggtggggccg agtcgatcac    1140
gacgctgccc ttcacccagg ccctcggcct gccggaggac gacttccgc tgcgcatcgc     1200
gcgcaacacg ggcatcgtgc tcgccgaaga ggtgaacatc ggccgcgtca acgacccggc    1260
cggtggctcc tactacgtcg agtcgctcac ccgcagcctg gccgacgccg cctggaagga    1320
attccaggag gtcgagaagc tcggtggcat gtcgaaggcc gtcatgaccg agcacgtcac    1380
caaggtgctc gacgcctgca atgccgagcg cgccaagcgc ctggccaacc gcaagcagcc    1440
gatcaccgcg gtcagcgagt tcccgatgat cggggcccgc agcatcgaga ccaagccgtt    1500
ccccgccgct ccggcgcgca agggcctggc ctggcatcgc gactccgagg tgttcgagca    1560
gctgatggat cgctccacca gcgtctccga gcgcccaag gtgttcctgg cctgcttggg     1620
cacccgtcgc gacttcggtg gccgcgaggg cttctcgagc ccggtgtggc acatcgccgg    1680
catcgacacc ccgcaggtcg aaggcggcac caccgccgag atcgtcgagg cattcaagaa    1740
gtcgggcgcc caggtggccg acctctgctc gtccgccaag gtctacgcgc agcagggact    1800
tgaggtcgcc aaggcactca aggccgccgg cgcaaaggcc ctgtacctgt cgggcgcctt    1860
caaggagttc ggtgatgacg ccgccgaggc gagaagctg atcgacggac gcctgtttat    1920
gggcatggat gtcgtcgaca ccctgtcctc caccccttgat atcttgggag tcgcgaagtg    1980
aagtacttgc aggagaaggc catcctgacg gatggccttt ttggcaggtg                2030
```

<210> SEQ ID NO 39
<211> LENGTH: 2341

<212> TYPE: DNA
<213> ORGANISM: Artificial Sequence
<220> FEATURE:
<223> OTHER INFORMATION: Synthetic polynucleotide

<400> SEQUENCE: 39

| | | | | | |
|---|---|---|---|---|---|
| cacctgctcc | acccttgata | tcttgggagt | cgcgaagtga | agtgaagcgg | cggtagctaa | 60 |
| gactaaagga | ggtaggaaat | ggaacaaaaa | ttgatctcgg | aagaagattt | gagcactctg | 120 |
| ccccgttttg | attcagttga | cctcggcaat | gccccggttc | ctgctgatgc | cgcacgacgc | 180 |
| ttcgaggaac | tggccgccaa | ggccggcacc | ggagaggcgt | gggagacggc | cgagcagatt | 240 |
| ccggttggca | ccctgttcaa | cgaagacgtc | tacaaggaca | tggactggct | ggacacctac | 300 |
| gcaggtatcc | cgccgttcgt | ccacggcccg | tatgcaacca | tgtacgcgtt | ccgtccctgg | 360 |
| acgattcgcc | agtacgccgg | tttctccacg | gccaaggagt | cgaacgcctt | ctaccgccgc | 420 |
| aaccttgcgg | ccggccagaa | gggcctgtcg | gttgccttcg | acctgcccac | ccaccgtggc | 480 |
| tacgactcgg | acaatccccg | cgtcgccggt | gacgtcggca | tggccggtgt | ggccatcgac | 540 |
| tccatctatg | acatgcgcga | gctgttcgcc | ggcattccgc | tggaccagat | gagcgtgtcc | 600 |
| atgaccatga | acgcgccgt | gctgccgatc | ctggccctct | atgtggtgac | cgccgaggag | 660 |
| cagggcgtca | gcccgagca | gctcgccggg | acgatccaga | cgacatcct | caaggagttc | 720 |
| atggttcgta | acacctacat | ctacccgccg | cagccgagta | tgcgaatcat | ctctgagatc | 780 |
| ttcgcctaca | cgagtgccaa | tatgccgaag | tggaattcga | tttccatttc | cggctaccac | 840 |
| atgcaggaag | ccggcgccac | ggccgacatc | gagatggcct | ataccctggc | cgacggtgtt | 900 |
| gactacatcc | gcgccggcga | gtcggtgggc | ctcaatgtcg | accagttcgc | gccgcgtctg | 960 |
| tccttcttct | ggggcatcgg | catgaacttc | ttcatggagg | ttgccaagct | gcgtgccgcg | 1020 |
| cgcatgttgt | gggccaagct | ggtgcatcag | ttcgggccga | agaacccgaa | gtcgatgagc | 1080 |
| ctgcgcaccc | actcgcagac | ctccggttgg | tcgctgaccg | cccaggacgt | ctacaacaac | 1140 |
| gtcgtgcgta | cctgcatcga | ggccatggcc | gccacccagg | gccataccca | gtcgctgcac | 1200 |
| acgaactcgc | tcgacgaggc | catcgccctg | ccgaccgatt | tcagcgcccg | catcgcccgt | 1260 |
| aacacccagc | tgttcctgca | gcaggaatcg | ggcacgacgc | gcgtgatcga | cccgtggagc | 1320 |
| ggctcggcat | acgtcgagga | gctcacctgg | gacctggccc | gcaaggcatg | gggtcacatc | 1380 |
| caggaggtcg | agaaggtcgg | cggcatggcc | aaggccatcg | aaaagggcat | ccccaagatg | 1440 |
| cgcatcgagg | aagccgccgc | ccgcacccag | gcacgcatcg | actccggccg | ccagccgctg | 1500 |
| atcggcgtga | caagtaccg | cctggagcac | gagccgccgc | tcgatgtgct | caaggtggac | 1560 |
| aactccacgg | tgctcgccga | gcagaaggcc | aagctggtca | agctgcgcgc | cgagcgcgat | 1620 |
| cccgagaagg | tcaaggccgc | cctcgacaag | atcacctggg | ccgccggcaa | ccccgacgac | 1680 |
| aaggatccgg | atcgcaacct | gctgaagctg | tgcatcgacg | ctggccgcgc | catggcgacg | 1740 |
| gtcggcgaga | tgagcgacgc | gctcgagaag | gtcttcggac | gctacaccgc | ccagattcgc | 1800 |
| accatctccg | gtgtgtactc | gaaggaagtg | aagaacacgc | ctgaggttga | ggaagcacgc | 1860 |
| gagctcgttg | aggaattcga | gcaggccgag | ggccgtcgtc | ctcgcatcct | gctggccaag | 1920 |
| atgggccagg | acggtcacga | ccgtggccag | aaggtcatcg | ccaccgccta | tgccgacctc | 1980 |
| ggtttcgacg | tcgacgtggg | cccgctgttc | cagaccccgg | aggagaccgc | acgtcaggcc | 2040 |
| gtcgaggccg | atgtgcacgt | ggtgggcgtt | tcgtcgctcg | ccggcgggca | tctgacgctg | 2100 |
| gttccggccc | tgcgcaagga | gctggacaag | ctcggacgtc | ccgacatcct | catcaccgtg | 2160 |

```
ggcggcgtga tccctgagca ggacttcgac gagctgcgta aggacggcgc cgtggagatc    2220 tacaccccccg gcaccgtcat tccggagtcg gcgatctcgc tggtcaagaa actgcgggct    2280
tcgctcgatg cctagagtac ttgcaggaga aggccatcct gacggatggc ctttgcaggt    2340
g                                                                    2341

<210> SEQ ID NO 40
<211> LENGTH: 524
<212> TYPE: DNA
<213> ORGANISM: Artificial Sequence
<220> FEATURE:
<223> OTHER INFORMATION: Synthetic polynucleotide

<400> SEQUENCE: 40
ctatttaaat aaaggaggtc ttaagatgga ctacaaggat gacgatgaca agagtaatga     60
ggatcttttc atctgtatcg atcacgtggc atatgcgtgc cccgacgccg acgaggcttc    120
caagtactac caggagacct tcggctggca tgagctccac cgcgaggaga acccggagca    180
gggagtcgtc gagatcatga tggccccggc tgcgaagctg accgagcaca tgacccaggt    240
tcaggtcatg gccccgctca acgacgagtc gaccgttgcc aagtggcttg ccaagcacaa    300
tggtcgcgcc ggactgcacc acatggcatg gcgtgtcgat gacatcgacg ccgtcagcgc    360
caccctgcgc gagcgcggcg tgcagctgct gtatgacgag cccaagctcg gcaccggcgg    420
caaccgcatc aacttcatgc atcccaagtc gggcaagggc gtgctcatcg agctcaccca    480
gtacccgaag aactgatgca ggagaaggcc atcctgacgg atgg                     524
```